(12) United States Patent
Yellin et al.

(10) Patent No.: US 11,534,300 B2
(45) Date of Patent: Dec. 27, 2022

(54) STABILIZING AND ADJUSTING TOOL FOR CONTROLLING A MINIMALLY INVASIVE MITRAL / TRICUSPID VALVE REPAIR SYSTEM

(71) Applicant: VALCARE, INC.

(72) Inventors: Nadav Yellin, Aven Yehuda (IL); Yoav Rozen, Binyamina (IL); Samuel Shaolian, Newport Beach, CA (US); Shuki Porath, Haifa (IL); Troy Thronton, San Francisco, CA (US); Guy Shimel, Tel Aviv (IL)

(73) Assignee: VALCARE, INC., Herzelyia Pituach (IL)

( * ) Notice: Subject to any disclaimer, the term of this patent is extended or adjusted under 35 U.S.C. 154(b) by 185 days.

(21) Appl. No.: 16/702,338

(22) Filed: Dec. 3, 2019

(65) Prior Publication Data
US 2020/0170799 A1 Jun. 4, 2020

Related U.S. Application Data

(60) Provisional application No. 62/774,651, filed on Dec. 3, 2018.

(51) Int. Cl.
*A61F 2/24* (2006.01)

(52) U.S. Cl.
CPC .......... *A61F 2/2448* (2013.01); *A61F 2/2442* (2013.01); *A61F 2/2466* (2013.01); *A61F 2220/0016* (2013.01); *A61F 2220/0025* (2013.01); *A61F 2220/0033* (2013.01); *A61F 2220/0075* (2013.01)

(58) Field of Classification Search
None
See application file for complete search history.

(56) References Cited

U.S. PATENT DOCUMENTS

| | | | |
|---|---|---|---|
| 4,602,911 | A | 7/1986 | Ahmadi et al. |
| 5,236,440 | A | 8/1993 | Hlavacek |
| 5,306,296 | A | 4/1994 | Wright et al. |
| 5,695,518 | A | 12/1997 | Laerum |
| 5,716,370 | A | 2/1998 | Williamson, IV et al. |

(Continued)

FOREIGN PATENT DOCUMENTS

| | | |
|---|---|---|
| EP | 2600799 A2 | 6/2013 |
| EP | 2967700 A1 | 1/2016 |

(Continued)

OTHER PUBLICATIONS 13860442.6, Extended European Search Report, dated Aug. 11, 2016, 7 pages.

(Continued)

*Primary Examiner* — Leslie Lopez

(57) ABSTRACT

Disclosed herein are embodiments related to a method for performing a minimally invasive procedure, the method including delivering an annuloplasty ring in a linear shape using a delivery system. In some embodiments, the delivery of the annuloplasty ring may utilize a trans-septal approach or a trans-apical. In some embodiments, the delivery system may position the annuloplasty ring using a flexible stabilizing mechanism and/or activate one or more anchors to extend outward from the annuloplasty ring.

13 Claims, 92 Drawing Sheets

(56) References Cited

U.S. PATENT DOCUMENTS

| | | |
|---|---|---|
| 5,855,614 A | 1/1999 | Stevens et al. |
| 6,113,611 A | 9/2000 | Allen et al. |
| 6,231,602 B1 | 5/2001 | Carpentier et al. |
| 6,619,291 B2 | 9/2003 | Hlavka et al. |
| 6,629,534 B1 | 10/2003 | St. Goar et al. |
| 6,669,687 B1 | 12/2003 | Saadat |
| 6,689,048 B2 | 2/2004 | Vanden Hoek et al. |
| 6,726,704 B1 | 4/2004 | Loshakove et al. |
| 6,776,784 B2 | 8/2004 | Ginn |
| 6,790,229 B1 | 9/2004 | Berreklouw |
| 6,797,002 B2 | 9/2004 | Spence et al. |
| 6,805,711 B2 | 10/2004 | Quijano et al. |
| 6,893,459 B1 | 5/2005 | Macoviak |
| 7,101,395 B2 | 9/2006 | Tremulis et al. |
| 7,114,953 B1 | 10/2006 | Wagner |
| 7,175,660 B2 | 2/2007 | Cartledge et al. |
| 7,238,191 B2 | 7/2007 | Bachmann |
| 7,285,087 B2 | 10/2007 | Moaddeb et al. |
| 7,297,150 B2 | 11/2007 | Cartledge et al. |
| 7,569,072 B2 | 8/2009 | Berg et al. |
| 7,594,887 B2 | 9/2009 | Moaddeb et al. |
| 7,635,329 B2 | 12/2009 | Goldfarb et al. |
| 7,655,040 B2 | 2/2010 | Douk et al. |
| 7,717,954 B2 | 5/2010 | Solem et al. |
| 7,722,668 B2 | 5/2010 | Moaddeb et al. |
| 7,758,637 B2 | 7/2010 | Starksen et al. |
| 7,837,729 B2 | 11/2010 | Gordon et al. |
| 7,988,725 B2 | 8/2011 | Gross et al. |
| 8,163,014 B2 | 4/2012 | Lane et al. |
| 8,182,529 B2 | 5/2012 | Gordon et al. |
| 8,236,049 B2 | 8/2012 | Rowe et al. |
| 8,287,591 B2 | 10/2012 | Keidar et al. |
| 8,518,107 B2 | 8/2013 | Tsukashima et al. |
| 8,579,968 B1 * | 11/2013 | Shannon ............... A61F 2/2445 623/2.37 |
| 2002/0151961 A1 | 10/2002 | Lashinski et al. |
| 2002/0151970 A1 | 10/2002 | Garrison et al. |
| 2002/0188170 A1 | 12/2002 | Santamore et al. |
| 2002/0198526 A1 | 12/2002 | Shaolian et al. |
| 2003/0050693 A1 | 3/2003 | Quijano et al. |
| 2003/0078465 A1 | 4/2003 | Pai et al. |
| 2003/0078671 A1 | 4/2003 | Lesniak et al. |
| 2003/0191528 A1 | 10/2003 | Quijano et al. |
| 2003/0198605 A1 | 10/2003 | Montgomery |
| 2003/0199974 A1 | 10/2003 | Lee et al. |
| 2004/0044364 A1 | 3/2004 | DeVries et al. |
| 2004/0068276 A1 | 4/2004 | Golden et al. |
| 2004/0122514 A1 | 6/2004 | Fogarty et al. |
| 2004/0138744 A1 | 7/2004 | Lashinski et al. |
| 2004/0148021 A1 | 7/2004 | Cartledge et al. |
| 2004/0193191 A1 | 9/2004 | Starksen et al. |
| 2004/0243230 A1 | 12/2004 | Navia et al. |
| 2004/0249391 A1 | 12/2004 | Cummins |
| 2004/0260393 A1 | 12/2004 | Rahdert et al. |
| 2004/0260394 A1 | 12/2004 | Douk et al. |
| 2005/0020696 A1 | 1/2005 | Montgomery et al. |
| 2005/0033325 A1 | 2/2005 | May et al. |
| 2005/0065550 A1 | 3/2005 | Starksen et al. |
| 2005/0090846 A1 | 4/2005 | Pedersen et al. |
| 2005/0096740 A1 | 5/2005 | Langberg et al. |
| 2005/0113910 A1 | 5/2005 | Paniagua et al. |
| 2005/0137692 A1 | 6/2005 | Haug et al. |
| 2005/0137695 A1 | 6/2005 | Salahieh et al. |
| 2005/0203549 A1 | 9/2005 | Realyvasquez |
| 2005/0222678 A1 | 10/2005 | Lashinski et al. |
| 2005/0240200 A1 | 10/2005 | Bergheim |
| 2005/0267572 A1 | 12/2005 | Schoon et al. |
| 2005/0283190 A1 | 12/2005 | Huitema et al. |
| 2005/0288778 A1 | 12/2005 | Shaoulian et al. |
| 2005/0288781 A1 | 12/2005 | Moaddeb et al. |
| 2006/0009737 A1 | 1/2006 | Whiting et al. |
| 2006/0020327 A1 | 1/2006 | Lashinski et al. |
| 2006/0122633 A1 | 6/2006 | To et al. |
| 2006/0129025 A1 | 6/2006 | Levine et al. |
| 2006/0155165 A1 | 7/2006 | Vanden Hoek et al. |
| 2006/0161169 A1 | 7/2006 | Nieminen et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0195183 A1 | 8/2006 | Navia et al. |
| 2006/0241748 A1 | 10/2006 | Lee et al. |
| 2006/0282161 A1 | 12/2006 | Huynh et al. |
| 2007/0016287 A1 | 1/2007 | Cartledge et al. |
| 2007/0027533 A1 | 2/2007 | Douk |
| 2007/0038296 A1 | 2/2007 | Navia et al. |
| 2007/0051377 A1 | 3/2007 | Douk et al. |
| 2007/0067027 A1 | 3/2007 | Moaddeb et al. |
| 2007/0073098 A1 | 3/2007 | Lenker et al. |
| 2007/0080188 A1 | 4/2007 | Spence et al. |
| 2007/0093854 A1 | 4/2007 | Kayan |
| 2007/0118215 A1 | 5/2007 | Moaddeb |
| 2007/0128132 A1 | 6/2007 | Piergallini et al. |
| 2007/0135913 A1 | 6/2007 | Moaddeb et al. |
| 2007/0142907 A1 | 6/2007 | Moaddeb et al. |
| 2007/0213812 A1 | 9/2007 | Webler et al. |
| 2007/0233239 A1 | 10/2007 | Navia et al. |
| 2007/0239272 A1 | 10/2007 | Navia et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0250161 A1 | 10/2007 | Dolan |
| 2007/0293942 A1 | 12/2007 | Mirzaee |
| 2008/0177380 A1 | 7/2008 | Starksen et al. |
| 2008/0177381 A1 | 7/2008 | Navia et al. |
| 2008/0200980 A1 | 8/2008 | Robin et al. |
| 2008/0243220 A1 | 10/2008 | Barker |
| 2008/0262513 A1 | 10/2008 | Stabler et al. |
| 2008/0262609 A1 | 10/2008 | Gross et al. |
| 2008/0306586 A1 | 12/2008 | Cartledge et al. |
| 2009/0088838 A1 | 4/2009 | Shaolian et al. |
| 2009/0118747 A1 | 5/2009 | Bettuchi et al. |
| 2009/0125098 A1 | 5/2009 | Chuter |
| 2009/0149872 A1 | 6/2009 | Gross et al. |
| 2009/0216322 A1 | 8/2009 | Le et al. |
| 2009/0222083 A1 | 9/2009 | Nguyen et al. |
| 2009/0238778 A1 | 9/2009 | Mordas et al. |
| 2009/0299470 A1 | 12/2009 | Rao et al. |
| 2010/0010616 A1 | 1/2010 | Drews et al. |
| 2010/0030014 A1 | 2/2010 | Ferrazzi |
| 2010/0063586 A1 | 3/2010 | Hasenkam et al. |
| 2010/0121433 A1 | 5/2010 | Bolling et al. |
| 2010/0161047 A1 | 6/2010 | Cabiri |
| 2010/0185274 A1 | 7/2010 | Moaddeb et al. |
| 2010/0211166 A1 | 8/2010 | Miller et al. |
| 2010/0249920 A1 | 9/2010 | Bolling et al. |
| 2010/0266989 A1 | 10/2010 | Piergallini et al. |
| 2010/0280605 A1 | 11/2010 | Hammer et al. |
| 2010/0286767 A1 | 11/2010 | Zipory et al. |
| 2011/0022168 A1 | 1/2011 | Cartledge |
| 2011/0027753 A1 | 2/2011 | Maurat et al. |
| 2011/0034953 A1 | 2/2011 | Milo |
| 2011/0066231 A1 | 3/2011 | Cartledge et al. |
| 2011/0093062 A1 | 4/2011 | Cartledge et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0190879 A1 | 8/2011 | Bobo et al. |
| 2011/0208298 A1 | 8/2011 | Tuval et al. |
| 2011/0224785 A1 | 9/2011 | Hacohen |
| 2011/0257728 A1 | 10/2011 | Kuehn |
| 2011/0282361 A1 | 11/2011 | Miller et al. |
| 2011/0301698 A1 | 12/2011 | Miller et al. |
| 2011/0301699 A1 | 12/2011 | Saadat |
| 2012/0022557 A1 | 1/2012 | Cabiri et al. |
| 2012/0022644 A1 | 1/2012 | Reich et al. |
| 2012/0059458 A1 | 3/2012 | Buchbinder et al. |
| 2012/0095455 A1 | 4/2012 | Rodmond et al. |
| 2012/0123531 A1 | 5/2012 | Fsukashima et al. |
| 2012/0136436 A1 | 5/2012 | Cabiri et al. |
| 2012/0165930 A1 | 6/2012 | Gifford, III et al. |
| 2012/0245604 A1 | 9/2012 | Tegzes |
| 2012/0310330 A1 | 12/2012 | Buchbinder et al. |

(56) References Cited

U.S. PATENT DOCUMENTS

| | | |
|---|---|---|
| 2013/0087598 A1 | 4/2013 | Surti |
| 2013/0116780 A1 | 5/2013 | Miller et al. |
| 2013/0166022 A1 | 6/2013 | Conklin |
| 2013/0204361 A1 | 8/2013 | Adams et al. |
| 2013/0226289 A1* | 8/2013 | Shaolian .............. A61F 2/2466 623/2.11 |
| 2013/0226290 A1 | 8/2013 | Yellin et al. |
| 2013/0282114 A1 | 10/2013 | Schweich, Jr. et al. |
| 2013/0289718 A1 | 10/2013 | Fsukashima et al. |
| 2013/0289720 A1 | 10/2013 | Dobrilovic |
| 2013/0304197 A1 | 11/2013 | Buchbinder et al. |
| 2014/0005778 A1 | 1/2014 | Buchbinder et al. |
| 2014/0046433 A1 | 2/2014 | Kovalsky |
| 2014/0058505 A1 | 2/2014 | Bielefeld |
| 2014/0114407 A1 | 4/2014 | Rajamannan |
| 2015/0173897 A1 | 6/2015 | Raanani et al. |
| 2015/0351903 A1 | 12/2015 | Morriss et al. |
| 2016/0022419 A1 | 1/2016 | Yellin et al. |
| 2016/0038286 A1 | 2/2016 | Yellin et al. |
| 2016/0089235 A1 | 3/2016 | Yellin |
| 2016/0106420 A1 | 4/2016 | Foerster et al. |
| 2016/0120642 A1* | 5/2016 | Shaolian .............. A61F 2/2466 623/1.18 |
| 2016/0120645 A1 | 5/2016 | Alon |
| 2016/0331534 A1 | 11/2016 | Buchbinder et al. |
| 2017/0042670 A1 | 2/2017 | Shaolian et al. |
| 2017/0231763 A1 | 8/2017 | Yellin |
| 2018/0042723 A1 | 2/2018 | Yellin et al. |
| 2018/0161160 A1 | 6/2018 | Shaolian et al. |
| 2018/0161161 A1 | 6/2018 | Yellin et al. |
| 2019/0133765 A1 | 5/2019 | Yellin et al. |

FOREIGN PATENT DOCUMENTS

| | | |
|---|---|---|
| KR | 1020040095482 | 11/2004 |
| RU | 125062 | 2/2013 |
| WO | 199009153 A1 | 2/1990 |
| WO | 9009153 A1 | 8/1990 |
| WO | 03017874 A1 | 3/2003 |
| WO | 03047467 A1 | 6/2003 |
| WO | 2005046488 A2 | 5/2005 |
| WO | 2009052427 A1 | 4/2009 |
| WO | 2009120764 A2 | 10/2009 |
| WO | 2010004546 A1 | 1/2010 |
| WO | 2010085659 A1 | 7/2010 |
| WO | 2011011443 A2 | 1/2011 |
| WO | 2011097355 A2 | 8/2011 |
| WO | 2012004679 A2 | 1/2012 |
| WO | 2012019052 A2 | 2/2012 |
| WO | 2012063228 A1 | 5/2012 |
| WO | 2012095159 A2 | 7/2012 |
| WO | 2012106354 A1 | 8/2012 |
| WO | 2012167095 A2 | 12/2012 |
| WO | 2013095816 A1 | 6/2013 |
| WO | 2013128436 A1 | 9/2013 |
| WO | 2013130641 A1 | 9/2013 |
| WO | 2013175468 A2 | 11/2013 |
| WO | 2014089424 A1 | 6/2014 |
| WO | 2014145399 A1 | 9/2014 |
| WO | 2014189509 A1 | 11/2014 |
| WO | 2014190329 A1 | 11/2014 |
| WO | 2014210600 A2 | 12/2014 |
| WO | 2015132668 A1 | 9/2015 |
| WO | 2018035118 A1 | 2/2018 |

OTHER PUBLICATIONS 14801009.3, Extended European Search Report, dated Dec. 5, 2016, 8 pages.
19151726.7, Extended European Search Report dated Jul. 22, 2019, 9 pages.
PCT/US2018/022910, International Search Report and Written Opinion, dated May 23, 2018, 6 pages.
European Search Report in EP 17155803.4 dated Aug. 9, 2017.
International Search Report and Written Opinion for PCT/US2011/046659 dated Jun. 4, 2012.
International Search Report and Written Opinion for PCT/US2012/040481 dated Dec. 6, 2012.
International Search Report and Written Opinion for PCT/US2013/042275 dated Feb. 20, 2014.
International Search Report and Written Opinion for PCT/US2013/073552 dated Mar. 6, 2014.
International Search Report and Written Opinion for PCT/US2014/030163 dated Aug. 27, 2014.
International Search Report and Written Opinion for PCT/US2014/039454 dated Oct. 22, 2014.
International Search Report and Written Opinion for PCT/US2014/039545 dated Oct. 22, 2014.
International Search Report and Written Opinion for PCT/US2017/046933 dated Dec. 21, 2017.
International Search Report for PCT/US2013/028065 dated Jun. 27, 2013.
International Search Report for PCT/US2013/058102 dated Apr. 21, 2014.
International Search Report for PCT/US2014/044920 dated Dec. 24, 2014.
Lendlein et al., Biodegradable, Elastic Shape-Memory Polymers for Potential Biomedical Applications, Science, vol. 296 (May 31, 2002), pp. 1673-1676.
Supplemental European Search Report and Written Opinion for EP 12793292.9 dated Nov. 11, 2014.
Supplemental European Search Report and Written Opinion for EP 14762806.9 dated Jul. 29, 2016.
Supplementary Partial European Search Report for EP 13755441 dated Oct. 15, 2015.
International Search Report and Written Opinion for PCT2019/064289 dated Feb. 5, 2020.

* cited by examiner

STABILIZING AND ADJUSTING TOOL FOR CONTROLLING A MINIMALLY INVASIVE MITRAL / TRICUSPID VALVE REPAIR SYSTEM

This application claims the benefit of U.S. Provisional Application No. 62/774,651 filed Dec. 3, 2018, the contents of which is hereby incorporated by reference herein in its entirety.

BACKGROUND

The present disclosure is generally related to a device for minimally invasive treatment of human tricuspid valve regurgitation.

Tricuspid valve regurgitation is a condition evidenced by leakiness of the tricuspid valve, which is located between the upper and lower chambers of the right side of the heart. An individual exhibiting tricuspid valve regurgitation will have blood leak backwards through the tricuspid valve each time the right ventricle contracts. More particularly, when the right ventricle contracts to pump blood toward the lungs, some of the blood leaks backward into the right atrium. This increases the volume of blood in the atrium, which can cause the right atrium to enlarge. Enlargement of the right atrium can result in a change in the pressure in both the nearby heart chambers and adjacent blood vessels.

Functional tricuspid valve regurgitation is the most common type of valve pathology and is usually associated with mitral valve disease. Currently, the majority of patients with both mitral valve disease and tricuspid valve regurgitation receive surgical treatment for the mitral valve only. Tricuspid valve regurgitation is commonly not diagnosed or ignored. Asymptotic dilation of the tricuspid annulus may benefit from repair independent of regurgitation. Without treatment for tricuspid dilation, mitral valve disease can lead to biventricular failure and even death.

Thus, a device and method for a minimally invasive treatment of human tricuspid valve regurgitation is needed.

BRIEF DESCRIPTION OF THE DRAWINGS

Aspects, features, benefits and advantages of the embodiments described herein will be apparent with regard to the following description, appended claims, and accompanying drawings where:

DETAILED DESCRIPTION

Figure 1:
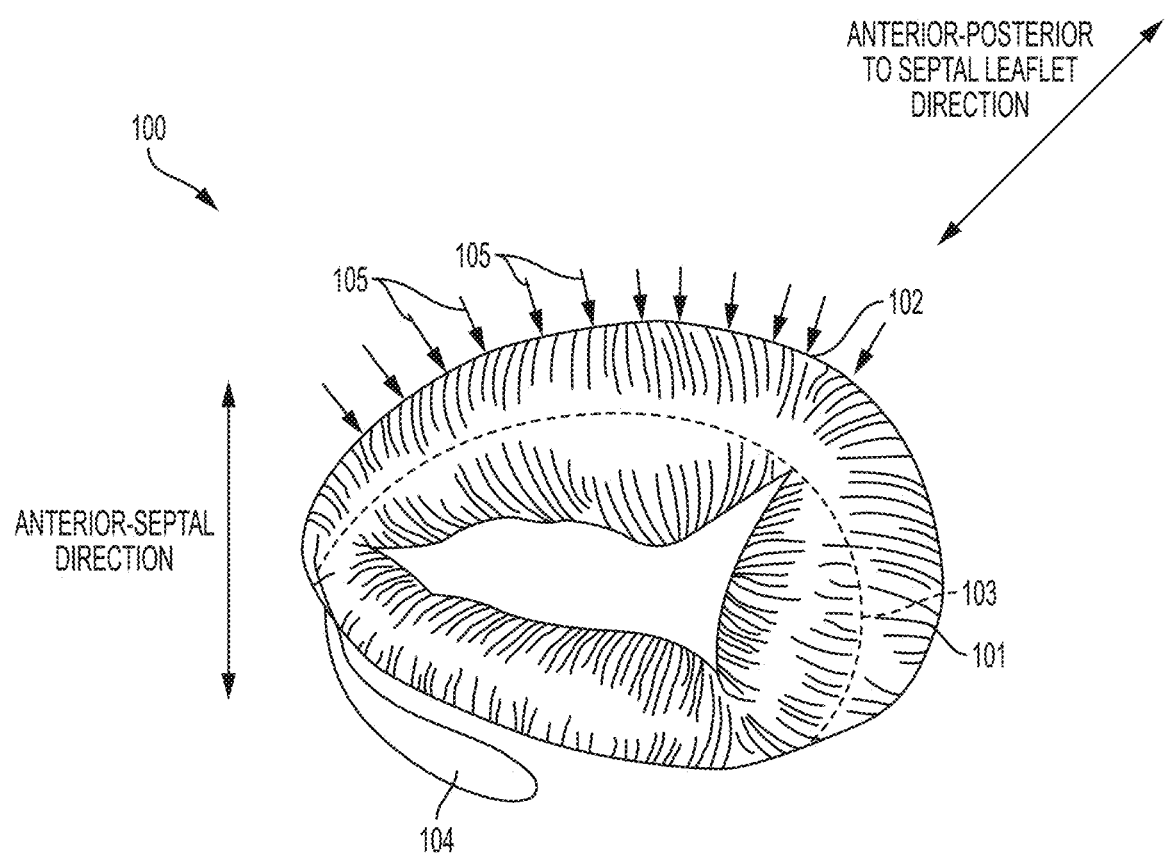
FIG. 1 depicts an illustrated tricuspid valve in normal and dilated conditions.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

As discussed herein, the existing treatment for tricuspid valve regurgitation is invasive and potentially dangerous. For example, current treatment may include repair methods such as DeVega Repair and utilization of annuloplasty rings or tricuspid rings that require open heart surgery. Open heart surgery may introduce several comorbidities in addition to any existing conditions. Thus, many patients who suffer from tricuspid valve regurgitation may not be appropriate candidates for open heart surgery, and would therefore greatly benefit from a new device and/or method for percutaneous or minimally invasive treatment of tricuspid valve regurgitation.

An implant and delivery system for introduction of a semi-rigid ring for treatment of tricuspid valve regurgitation includes a tricuspid annuloplasty ring comprising an outer hollow member with a plurality of segments. In a further embodiment, segments may be adjustable and may cooperate with one another in order to change the outer hollow member from an elongated insertion shaped geometry to an annular operable shaped geometry. The tricuspid annuloplasty ring may include one or more zones comprising internal anchor members located at least partially within the outer hollow member. In one non-limiting embodiment, the tricuspid annuloplasty ring may include up to four different anchor zones, which are further discussed herein. In an embodiment, the internal anchor members may be configured to emerge sequentially from windows (i.e., openings) along the hollow tube, thereby engaging the tissue of the tricuspid valve annulus under treatment, potentially in a predetermined sequence.

Disclosed herein are various embodiments related to minimally invasive or percutaneous trans-catheter delivery of a tricuspid ring. In addition, an embodiment may comprise methods for reducing or adjusting the dimension between the anterior and septal leaflets and/or reducing or adjusting the dimension between the anteroposterior commissure to septal leaflet, thereby minimizing or eliminating the issue of tricuspid valve regurgitation.

Accordingly, systems and methods are provided for introducing a tricuspid ring (e.g. while it is housed in a linear shape within the delivery system) in a trans-apical or trans-femoral approach. In an embodiment, the distal tip of the delivery system may be introduced above the tricuspid annulus. Once the tricuspid ring is introduced, the plane of the tricuspid ring may be rotated (e.g., automatically) to be parallel to the plane of the tricuspid annulus.

The tricuspid ring may then be snapped into a proper shape (e.g., a "D" shape) and introduced to the stabilization tool. The shape is possible because, as discussed herein, the tricuspid ring comprises an outer hollow member with a plurality of segments, wherein the segments may be adjustable and may cooperate with one another in order to change the outer hollow member from an annular operable shaped geometry to an elongated insertion shaped geometry and vice versa.

Once the tricuspid ring is properly controlled by the stabilization tool (e.g., as depicted in FIGS. 38-54), the properly shaped (e.g., "D" shaped) tricuspid ring may be inserted and guided to the desired location within the patient (e.g., the tricuspid valve). Once in the proper location, an embodiment may deploy a plurality of anchors. For example, an embodiment may deploy anchors associated with the septal zone, the posterior zone, or the first or second anterior zones.

In a further embodiment, the anchored tricuspid ring is anchored towards the septal leaflet, thereby reducing the height of the anterior-septal leaflets by approximately 15% to 20%. One or more second anterior zone anchors may also be deployed. In another embodiment, the design of the tricuspid ring may not include anchors in certain zones (e.g., the AV node zone). As discussed herein, this may be due to a particular zone being sensitive to external forces which could lead to adverse effects for the patient such as Arrhythmia, an irregular heart rhythm or heart failure.

Additionally or alternatively, the tricuspid ring (e.g., the septal zone and the posterior zone) may be dragged by the stabilizing tool to reduce the height of the anterior-septal leaflet height prior to the anchors in the first and second anterior zones being applied.

The illustrated example embodiments will be best understood by reference to the figures. The following description is intended only by way of example, and simply illustrates certain example embodiments.

Referring to FIG. 1, a perspective view of a tricuspid valve 100, as it relates to various embodiments discussed herein, is shown. As shown the tricuspid valve 100 may have an anterior-septal direction and an anterior-posterior to septal leaflet direction. Additionally, FIG. 1 illustrates an outline of a normal sized annulus 101, a dilated annulus 102, a desired shape of a tricuspid ring 103, and an Atrioventricular (AV) node 104. FIG. 1 further shows the annular reduction directions (i.e., the plurality of arrows 105) that may be required to reduce tricuspid valve regurgitation.

As would be understood by one skilled in the art, the AV node 104 is a part of the electrical conduction system of the heart that coordinates the top of the heart. The AV node 104 is an area of specialized tissue between the atria and the ventricles of the heart, specifically in the posteroinferior region of the interatrial septum near the opening of the coronary sinus, which conducts the normal electrical impulse from the atria to the ventricles. Puncturing or introducing any impulse into this node causes adverse effects such as Arrhythmia, irregular heart rhythm, and, in the worst case, heart failure. Therefore, in an embodiment, the design of a tricuspid ring may not include anchors in the segment of the ring that will be located adjacent to the AV node.

Figure 2:
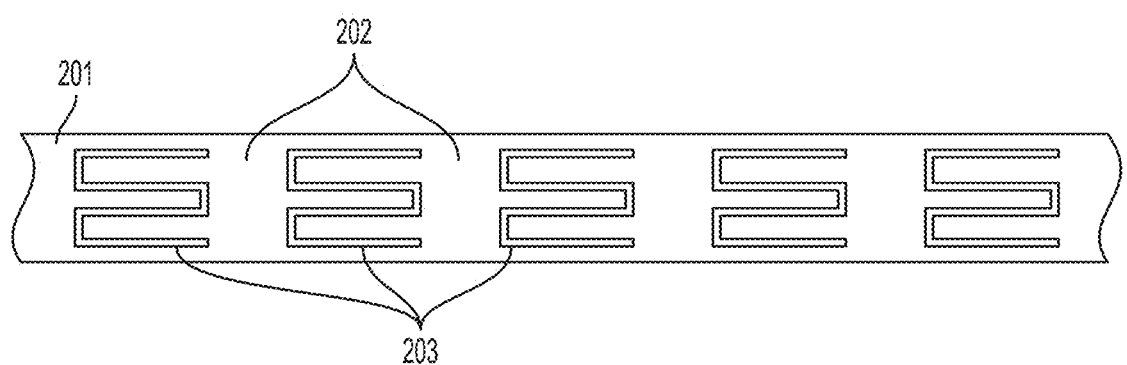
FIG. 2 depicts an illustrated pattern cut into a hollow tube, which is used to form a tricuspid ring.
Figure 3:
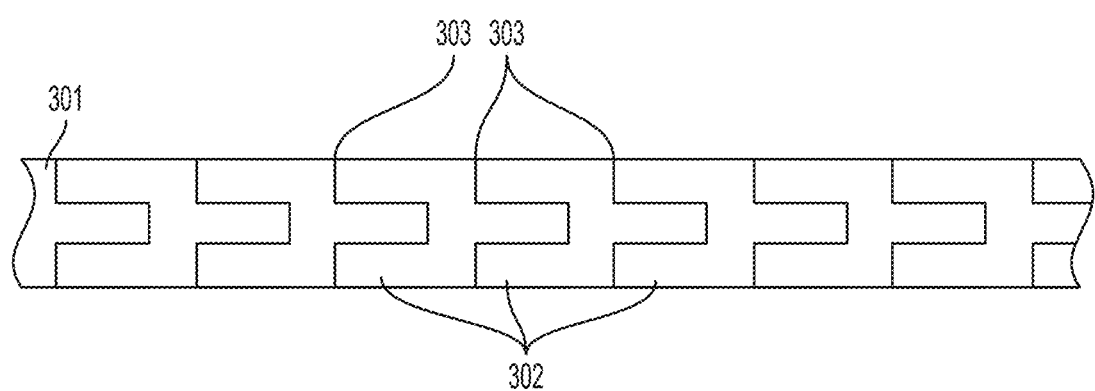
FIG. 3 depicts another illustrated pattern cut into a hollow tube, which is used to form a tricuspid ring.
Figure 4:
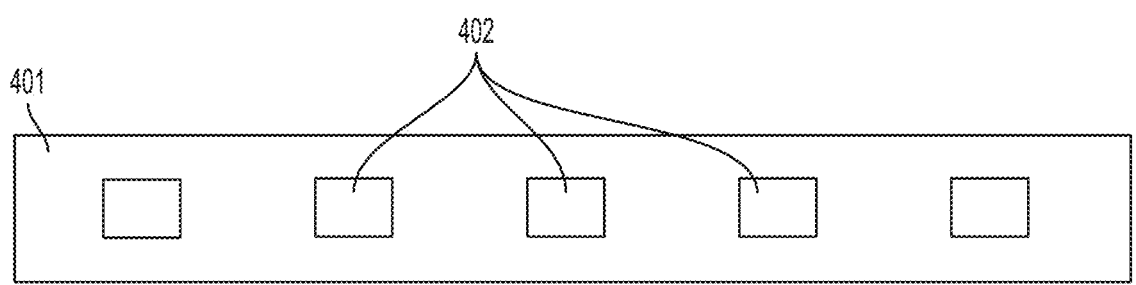
FIG. 4 depicts the back side of the hollow tube and the pattern of the cuts for anchor deployment windows.

In FIGS. 2 and 3, a perspective view of an illustrative embodiment may include a hollow tube 201/301, which may be made of various materials (e.g., a shape memory hypotube (nickel titanium (Ni—Ti) super elastic alloy)) cut to form a plurality of segments 202/302. In one embodiment, the cuts 203/303 in the hollow tube may allow for the tube to be used as an outer tube of a segmented tricuspid annuloplasty ring. Additionally, FIG. 4 shows an illustrative schematic diagram further detailing the cutting pattern used for laser processing (e.g., the cutting of windows 402 through which anchors (not shown) may be deployed) of the hypotube 401 as illustrated in FIGS. 2 and 3.

Figure 5:
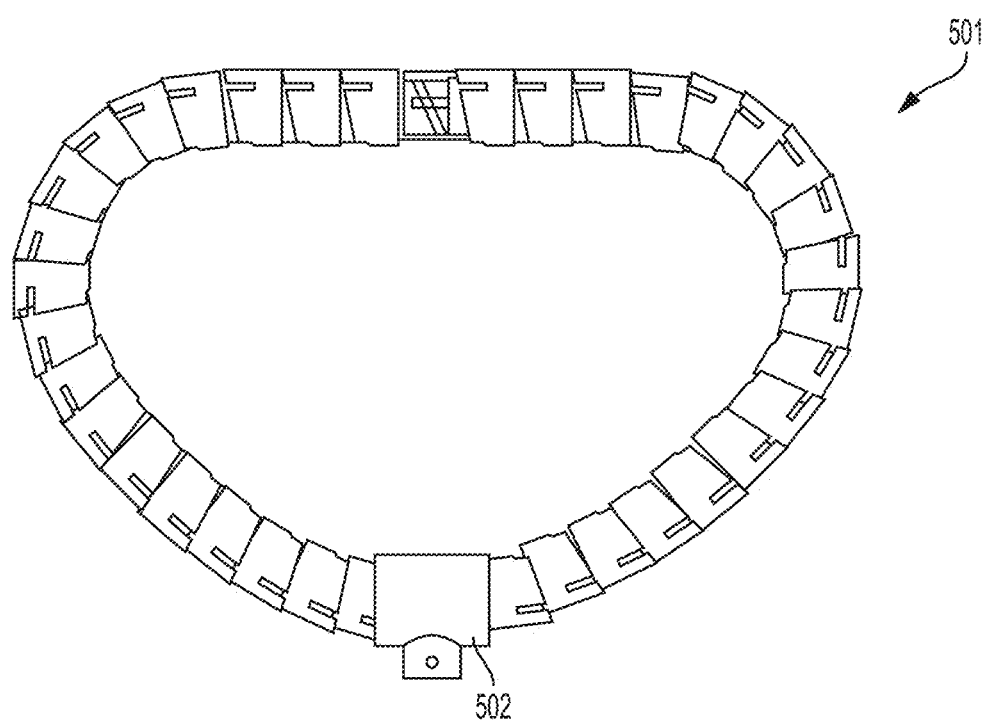
FIG. 5 depicts an illustrated shape of a tricuspid ring.

In an embodiment, as shown by the schematic diagram in FIG. 5, the shape of the memory hypotube 501, as discussed and shown in FIGS. 2 and 3, may have an operable geometry. For example, the hypotube may be annular and/or D-shaped (as shown in FIG. 5). Furthermore, an embodiment may, as shown, comprise a delivery system interface point 502.

Figure 6:
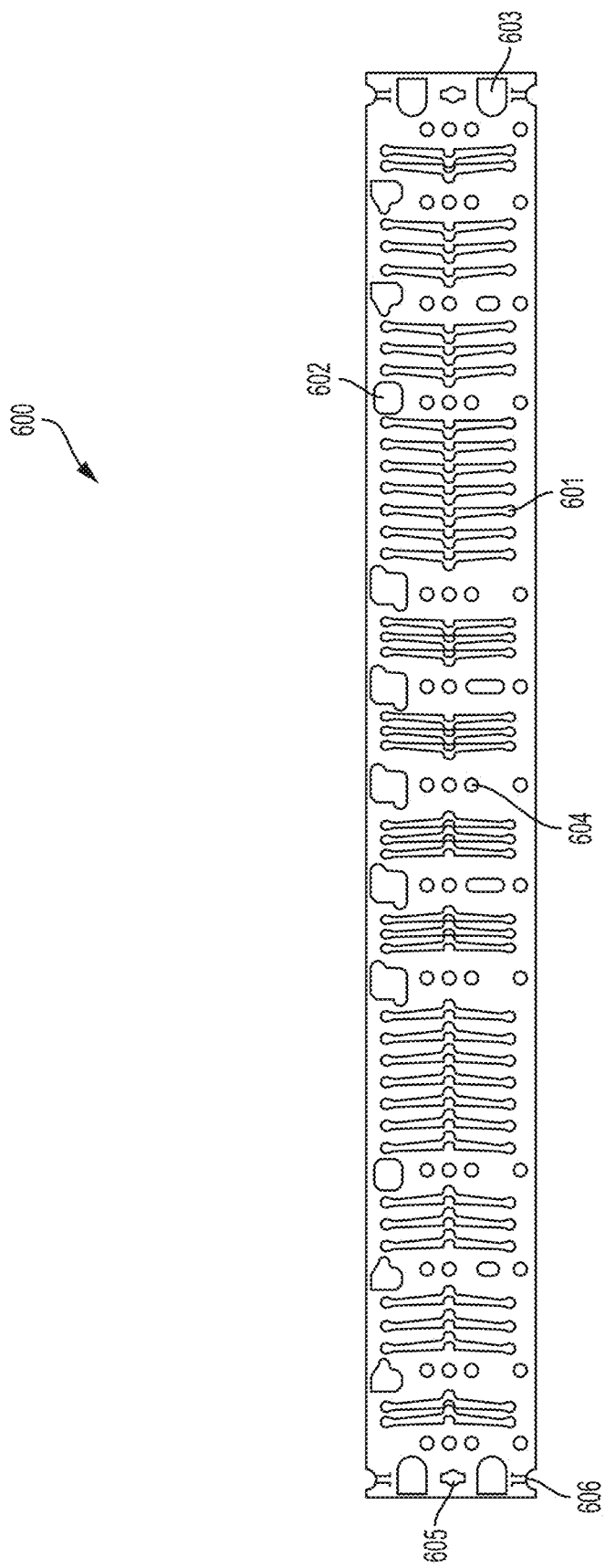
FIG. 6 depicts an illustrated schematic laser cut pattern.

Referring now to FIG. 6, a schematic laser cut pattern 600 for use in laser processing is shown. In one embodiment, the laser cut pattern 600 may integrate a plurality of segments (e.g., the windows for the anchors and the specific attachment holes for additional members. In one embodiment, one or more closing feature(s) may utilize the specific attachment holes in order to secure a connection and close the tricuspid ring. Thus, as shown in FIG. 6, an illustrative embodiment may include one or more laser cut patterns 600, one or more laser cut slots for flexibility 601, one or more windows for anchors 602, one or more windows for sutures 603, one or more holes for fabric attachment and fluorinated ethylene propylene (FEP) attachment 604, one or more holes for a suture pin 605, and one or more snap features for the suture pin 606.

Fluorinated ethylene propylene or FEP is a copolymer of hexafluoropropylene and tetrafluoroethylene FEP differs from polytetrafluoroethylene resins in that it is melt-processable using conventional injection molding and screw extrusion techniques. Moreover, FEP has a very low coefficient of friction and thus, in an embodiment, may make an exceptional material to serve as an anchor track and/or anchor the assemblies within the laser cut Ni—Ti rings. FEP provides various benefits over current methods, which require a significant pulling force to retrieve a metal end of a metal ring, particularly one that has a bend radius, after deployment from a catheter. In contrast, an embodiment may utilize an FEP tube that is laser cut and allows easy sliding of the anchor assembly within the laser cut Ni—Ti ring.

FEP is very similar in composition to the fluoropolymers PTFE (polytetrafluoroethylene) and PFA (perfluoroalkoxy polymer resin). FEP and PFA both share PTFE's useful properties of low friction and non-reactivity, but are more easily formable. FEP is softer than PTFE and melts at 260° C. It is also highly transparent and resistant to sunlight.

In some embodiments, at the fabric and FEP attachment points 604, a fabric maybe secured to cover the tube. The fabric may comprises multiple materials. In some embodiments, polyester is used to encourage tissue ingrowth.

Figure 7:
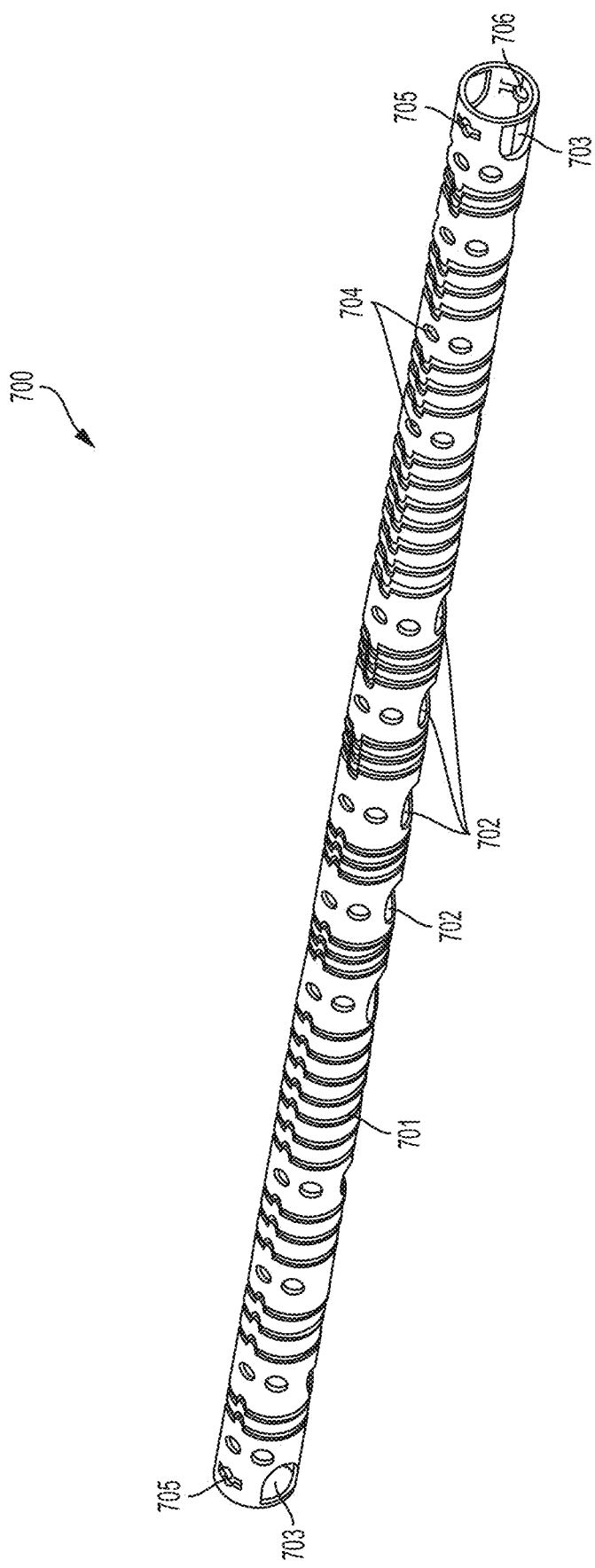
FIG. 7 depicts an illustrated schematic laser cut tube.

As shown in FIG. 7, a further embodiment may include a schematic laser cut tube 700. In one embodiment, the schematic laser cut tube 700 configuration may integrate a plurality of segments (e.g., the windows for the anchors and the specific attachment holes for additional members such as a closing feature(s) to close the tricuspid ring). Thus, as shown in FIG. 7, an illustrative embodiment may include one or more laser cut slots for flexibility 701, one or more windows for anchors 702, one or more windows for sutures 703, one or more holes for fabric and FEP attachment 704, one or more holes for a suture pin 705, and a snap feature for the suture pin 706.

Figure 8:
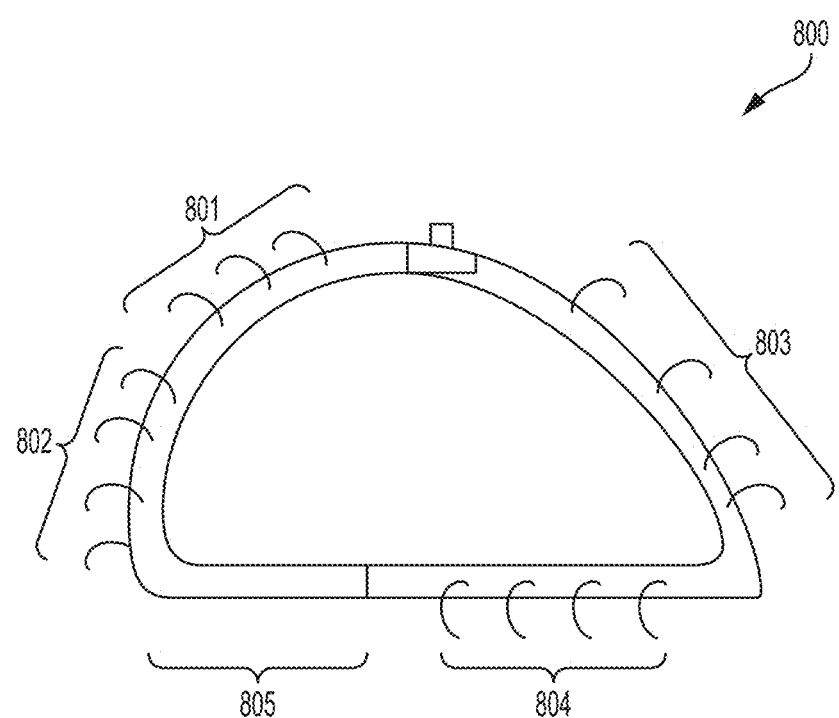
FIG. 8 depicts a perspective view of an illustrated tricuspid ring with the deployed anchors.

Referring now to FIG. 8, a perspective view of an illustrative embodiment is shown including a tricuspid annuloplasty ring 800 with four zones of internal anchors being deployed. Specifically, an embodiment may have a first anterior anchoring zone 801, a second anterior anchoring zone 802, a posterior anchoring zone 803, a septal anchoring zone 804, and an AV node zone 805. In some embodiments, the AV node zone may comprise no anchors.

Figure 9:
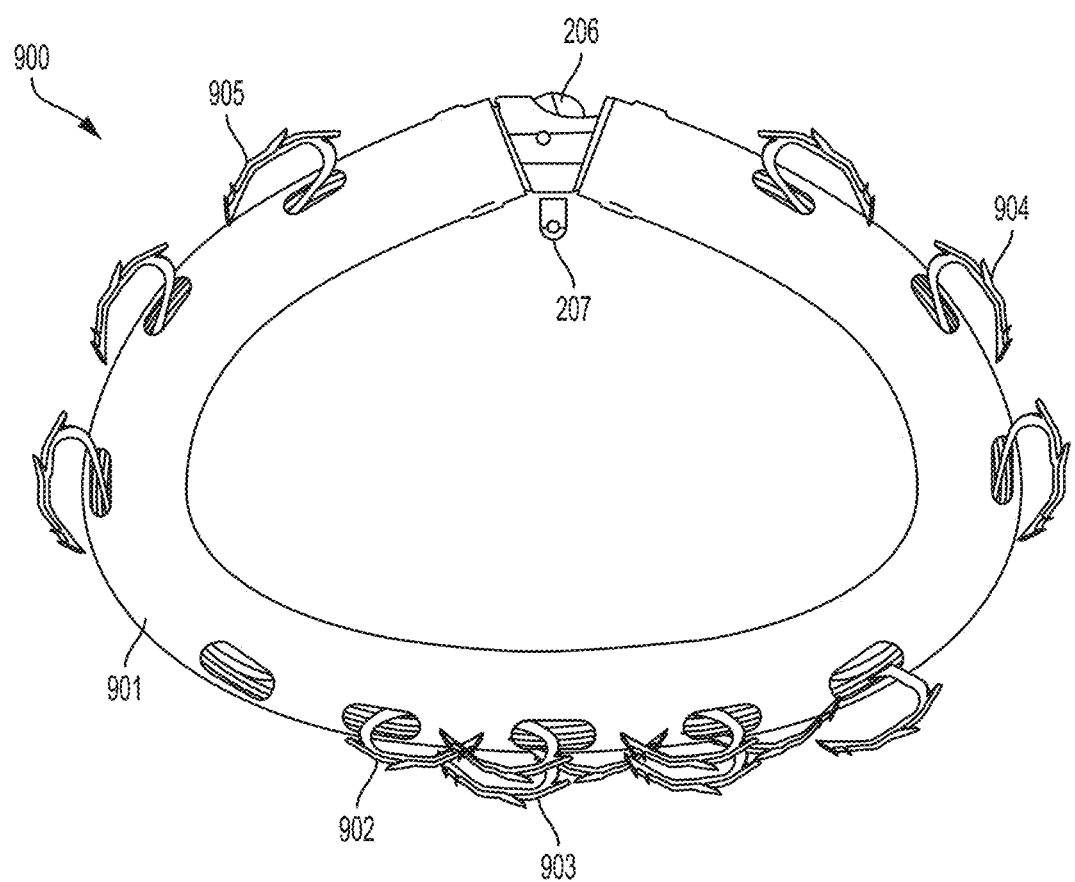
FIG. 9 depicts a perspective view of an illustrated tricuspid ring with zone distributions.

Additionally or alternatively, FIG. 9 illustrates alternative zone distributions in a tricuspid ring. In this configuration, the septal zones may overlap to form an improved attachment to the septal annulus. As shown in FIG. 9, an illustrative embodiment may include a tricuspid ring with four zones of anchors 900, an outer ring 901, a first septal zone 902, a second septal zone 903, a posterior zone 904, and an anterior zone 905, a snapping/closure mechanism 906, and a pivot pin attachment point 907, wherein the pivot pin attachment point attaches to a snapping mechanism of a delivery system.

Figure 10:
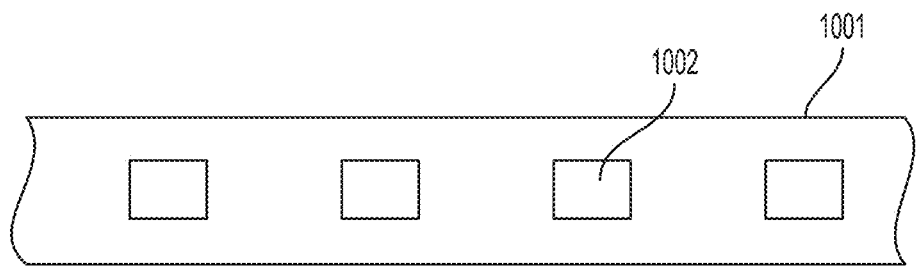
FIG. 10 depicts a perspective view of an illustrated laser cut fluorinated ethylene propylene (FEP) material.
Figure 11:
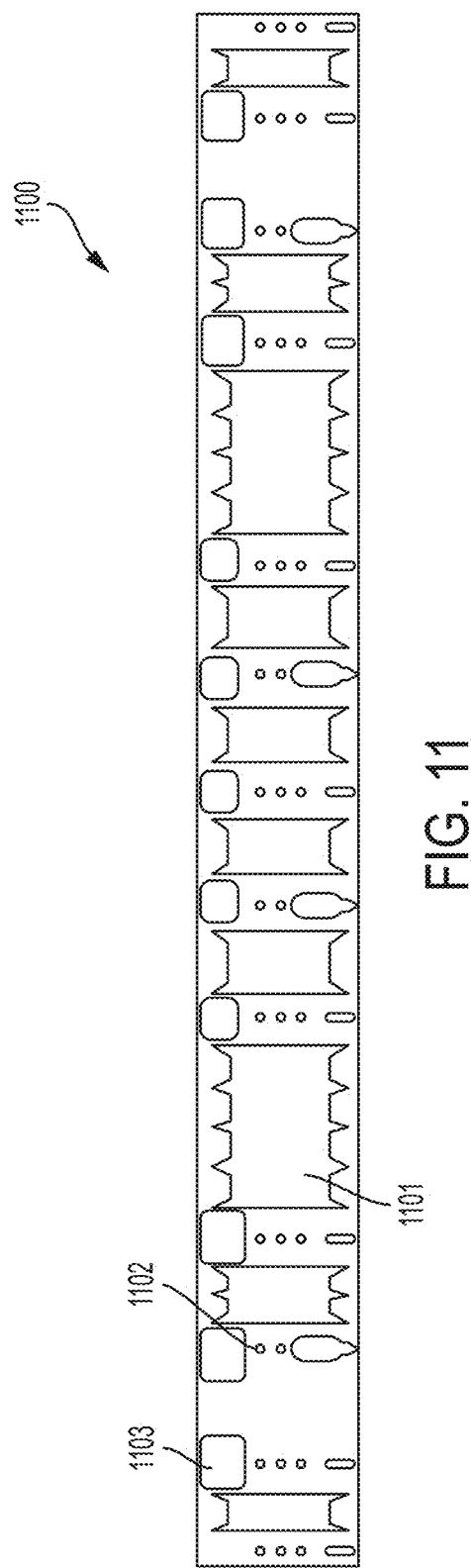
FIG. 11 depicts an illustrative laser cut pattern of a FEP tube.

Referring now to FIG. 10, a perspective view of a laser cut FEP 1001 that is used as a lining for the inside diameter of the hollow laser cut tube is shown. In one embodiment, the laser cut FEP may include laser cut anchor deployment windows 1002 that correspond to the laser cut windows on the hollow segmented tube (i.e., 700 shown in FIG. 7). Additionally, an embodiment may, as shown in FIG. 11, include a laser cut pattern 1100 for the FEP to enable it to properly line the inside diameter of the hollow laser cut tube. Moreover, as shown in FIG. 11, the laser cut pattern may include laser cut windows 1103 that correspond to laser cut windows on the hollow segmented tube, wherein both patterns allow for the flexibility of the FEP tube to bend along with the outer ring. As shown in FIG. 11, an illustrative embodiment may include a laser cut FEP 1100, a material release to allow flexibility 1101, one or more corresponding holes for sutures and coding of the FEP to the ring tube 1102, and one or more corresponding windows for the anchors 1103.

Figure 12:
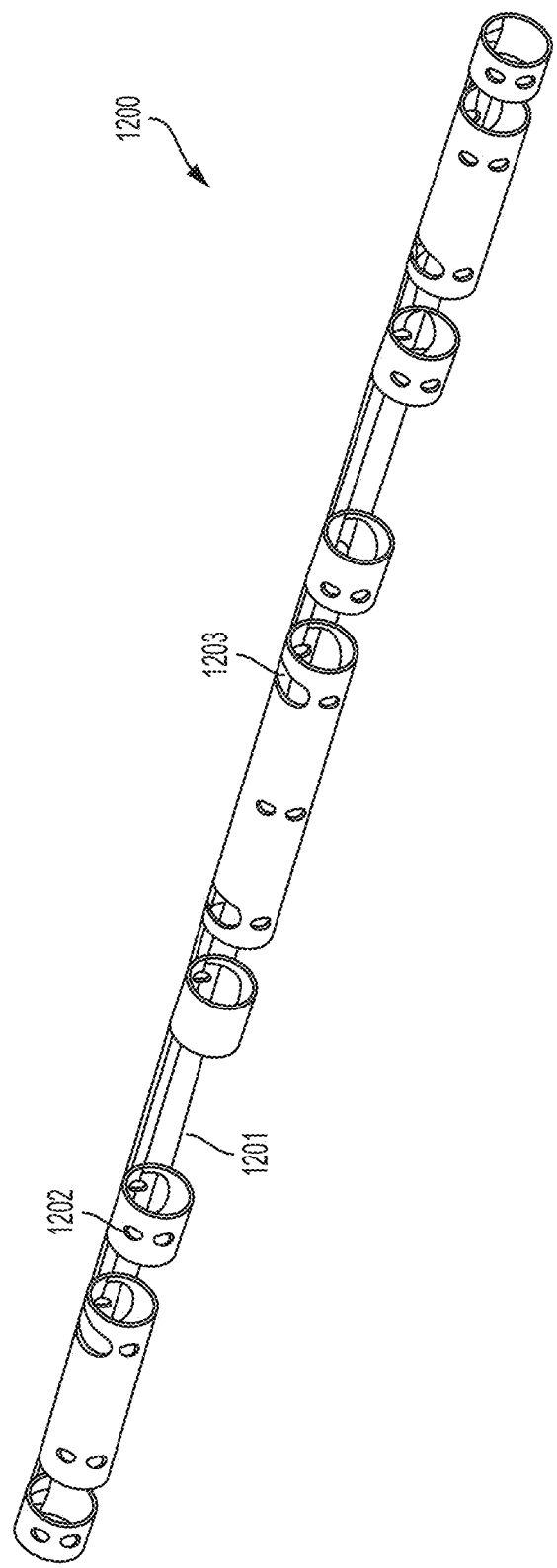
FIG. 12 depicts an illustrative laser cut FEP material in a tubular configuration.

FIG. 12 shows an alternate perspective view of an embodiment including a laser cut FEP in its tubular configuration 1200. As shown, the laser cut FEP 1200 may provide a lining for the inside diameter of the hollow laser cut tube, and include one or more laser cut windows that correspond to one or more laser cut windows 1203 on the hollow segmented tube, as discussed herein. A further embodiment may have a pattern that allows the FEP tube 1200 to be flexible and bend with the outer ring, such as that shown in FIG. 12. As shown in FIG. 12, an embodiment may include a laser cut FEP 1200, a material release to allow flexibility 1201, one or more corresponding holes for sutures and coding of the FEP to the tricuspid ring tube 1202, and one or more corresponding windows 1203 for the anchors.

Figure 13:
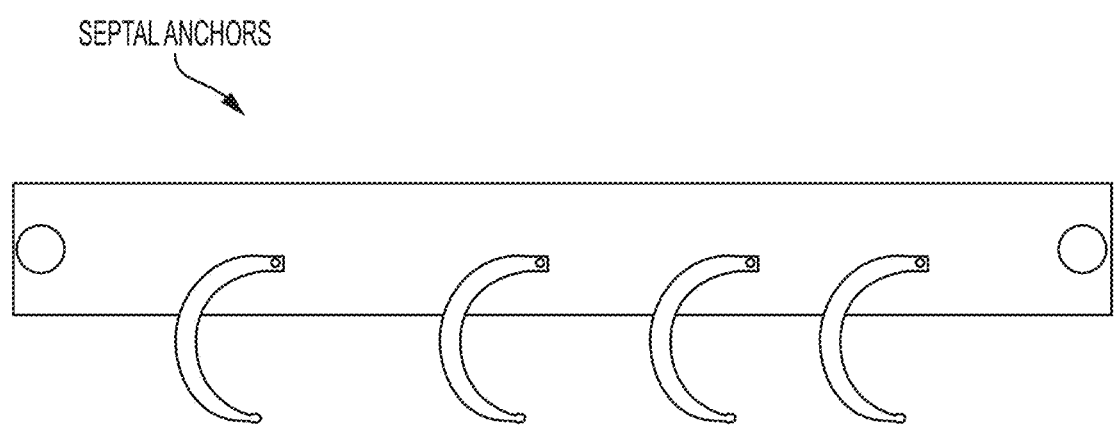
FIG. 13 depicts an illustrated geometric view of septal anchors.
Figure 14:
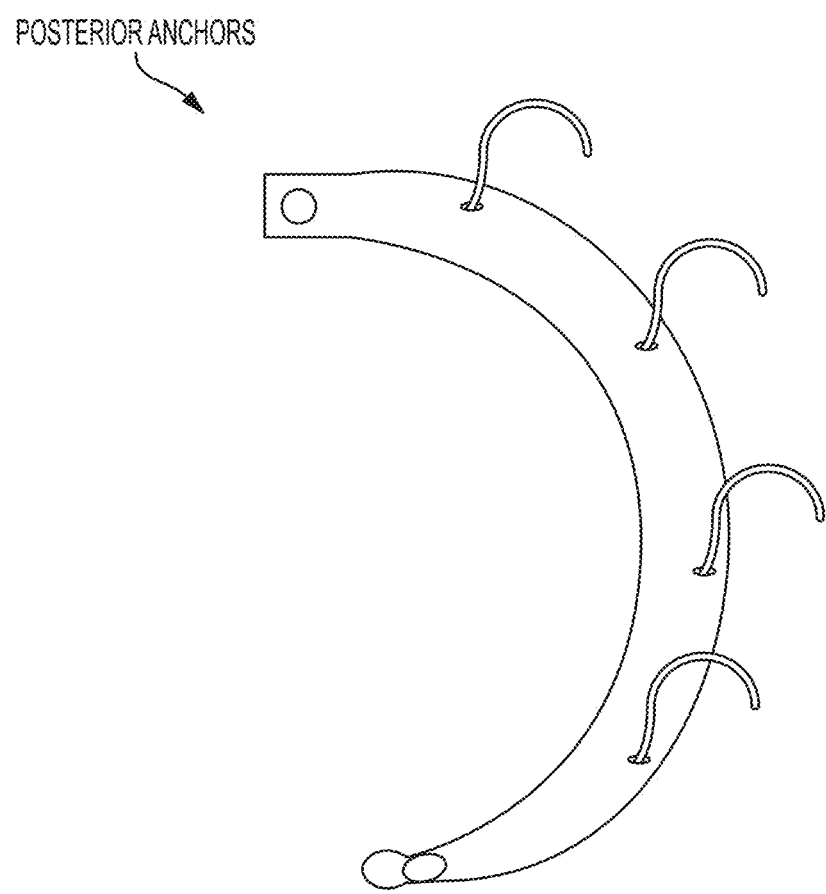
FIG. 14 depicts an illustrated geometric view of posterior anchors.
Figure 15:
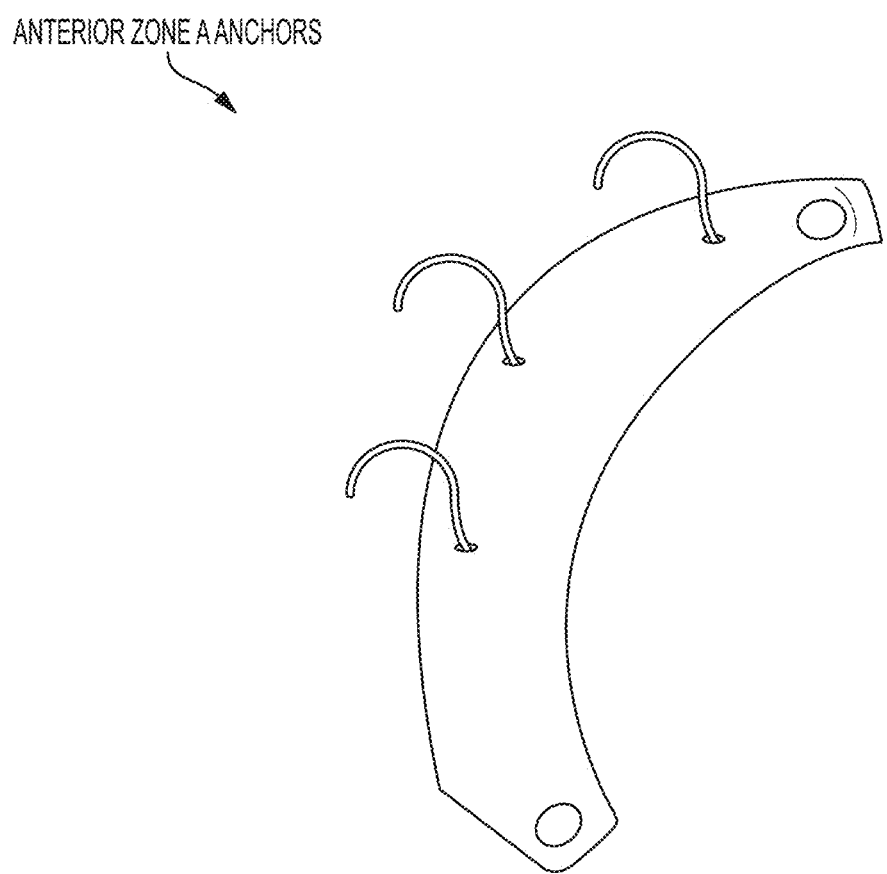
FIG. 15 depicts an illustrated geometric view of anterior anchors in zone A.
Figure 16:
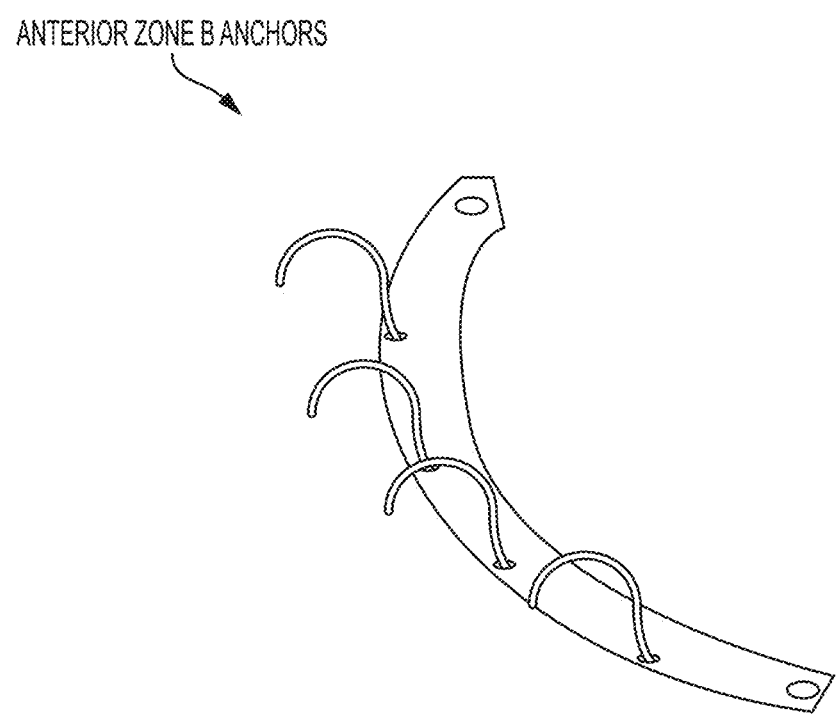
FIG. 16 depicts an illustrated geometric view of anterior anchors in zone B.

Referring to FIGS. 13-16, embodiments are shown that illustrate the geometry and view of four anchor rails. For example, FIG. 13 depicts the anchor rail for the septal zone of the tricuspid ring and FIG. 14 depicts the anchor rail for the posterior leaflet. FIGS. 15 and 16 depict two anchor rails which are each designed to anchor the tricuspid ring to the anterior section of the tricuspid valve (e.g., Zone A and Zone B of the anterior section).

Figure 17:
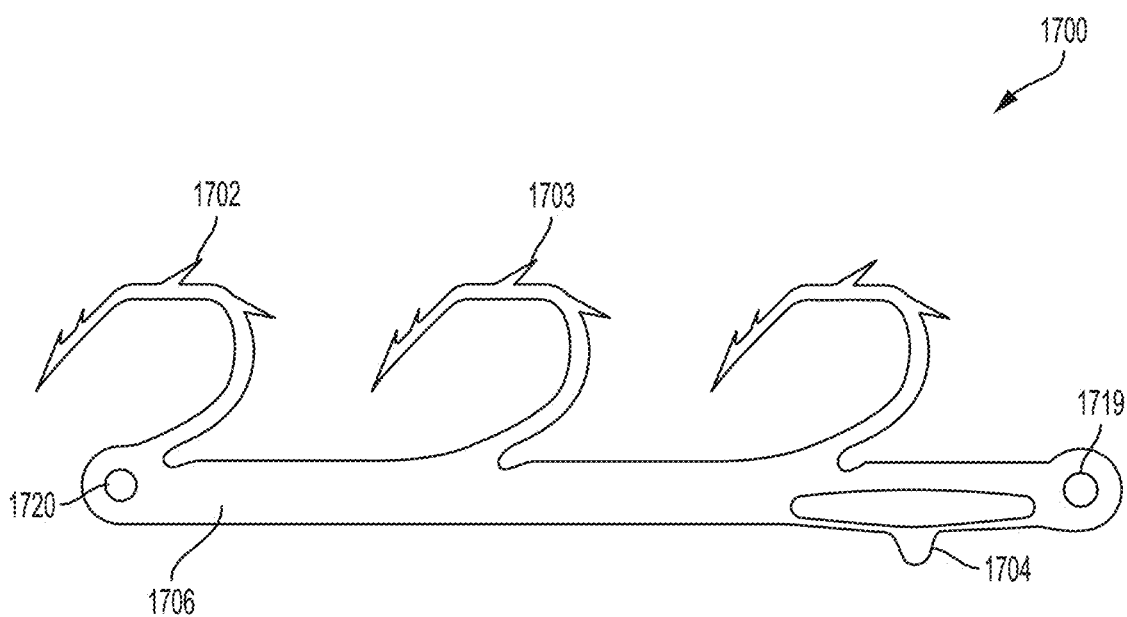
FIG. 17 depicts an illustrated laser cut pattern for a posterior and/or anterior zone.

A further embodiment, as illustrated in FIG. 17, may have an anchor system for a posterior/anterior zone. By way of non-limiting example, an illustrative embodiment, such as is shown in FIG. 17, may include an anchor zone 1700, a harpoon 1702, a harpoon barb 1703, an anchor stop (AS) feature 1704, an anchor zone rail 1706, an anchor zone deployment hole 1719, and a loading hole 1720.

As discussed herein, various embodiments may employ an anchor stop (e.g., 1704). The need for an anchor stop arises from the fact that the anchors may move after a tricuspid ring is deployed from the catheter (e.g., in linear shape) and takes on the "D" shape, as discussed herein. Specifically, the anchor assemblies that were held stationary when the ring was held in a linear position (e.g., the anchors held beneath and adjacent to the windows in the laser cut tube) may start moving and emitting prematurely from the windows because of the bend radius of the ring.

Thus, in order to combat premature deployment, which may render the ring useless and cause serious issues during the procedure, an embodiment utilizes the anchor stops to hold the anchors in place until the ring has reached its final location and deployment is appropriate. Once the assembly has reached its final location, the anchor stop may be overcome when an operator pulls a suture that is connected to the anchor assembly and forces the assembly and its stopper to slide, thus deploying the anchor systems, in the method discussed herein. Generally, an anchor stop is a bump geometrical feature, or step that prevents the anchor assembly from moving when the ring is deployed out of the delivery system; however, various embodiments and configurations are discussed herein and shown in the corresponding figures.

Figure 18:
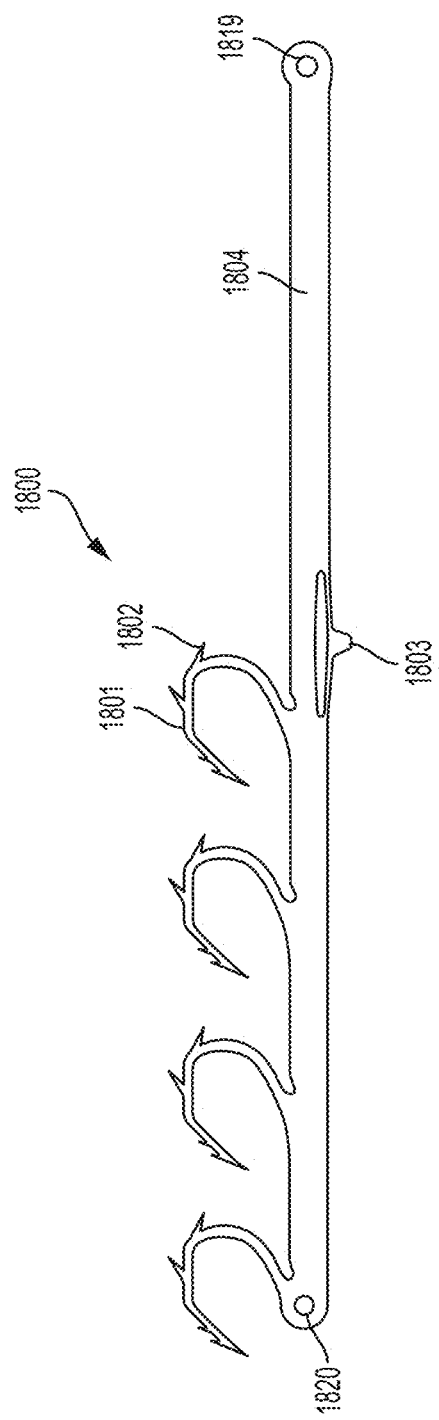
FIG. 18 depicts a laser cut pattern for a septal zone.
Figure 19:
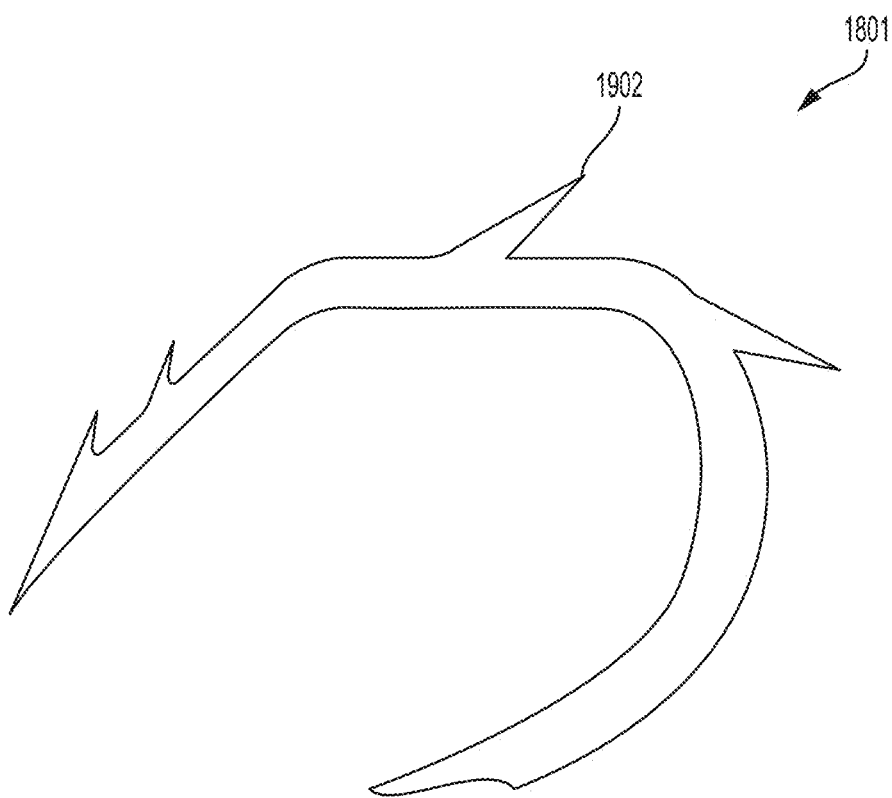
FIG. 19 depicts detail view of an illustrated harpoon.
Figure 20:
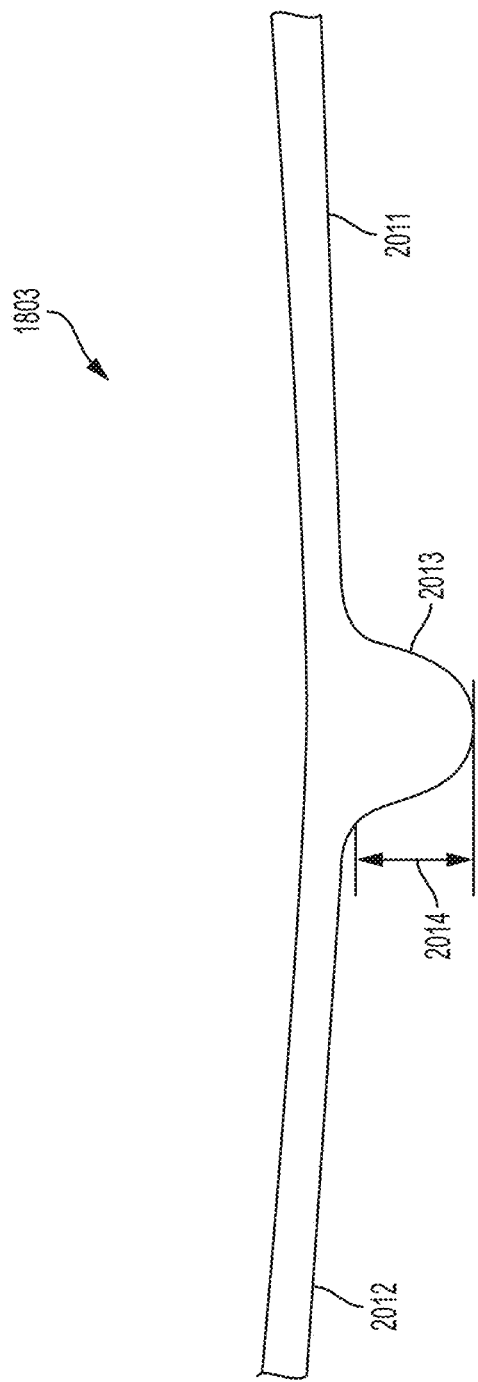
FIG. 20 depicts a detail view an illustrated anchor stop feature.

In another embodiment, illustrated in FIG. 18, a laser cut pattern may be used for a septal zone. As shown in FIG. 18, an embodiment may include an anchor zone 1800, a harpoon 1801, a harpoon barb 1802, an anchor stop (AS) feature 1803, an anchor zone rail 1804, an anchor zone deployment hole 1819, and a loading zone 1820. Additional detail regarding the harpoon 1801 is shown in FIG. 19. As illustrated by the embodiment in FIG. 19, the harpoon 1801 may have one or more harpoon barbs 1902. Additional detail regarding the anchor stop feature 1803 is shown in FIG. 20. As illustrated by the embodiment in FIG. 20, the anchor stop feature 1803 may include a first connecting strut 2011, a second connecting strut 2012, a deployment angle 2013, and an anchor stop feature height 2014.

Figure 21:
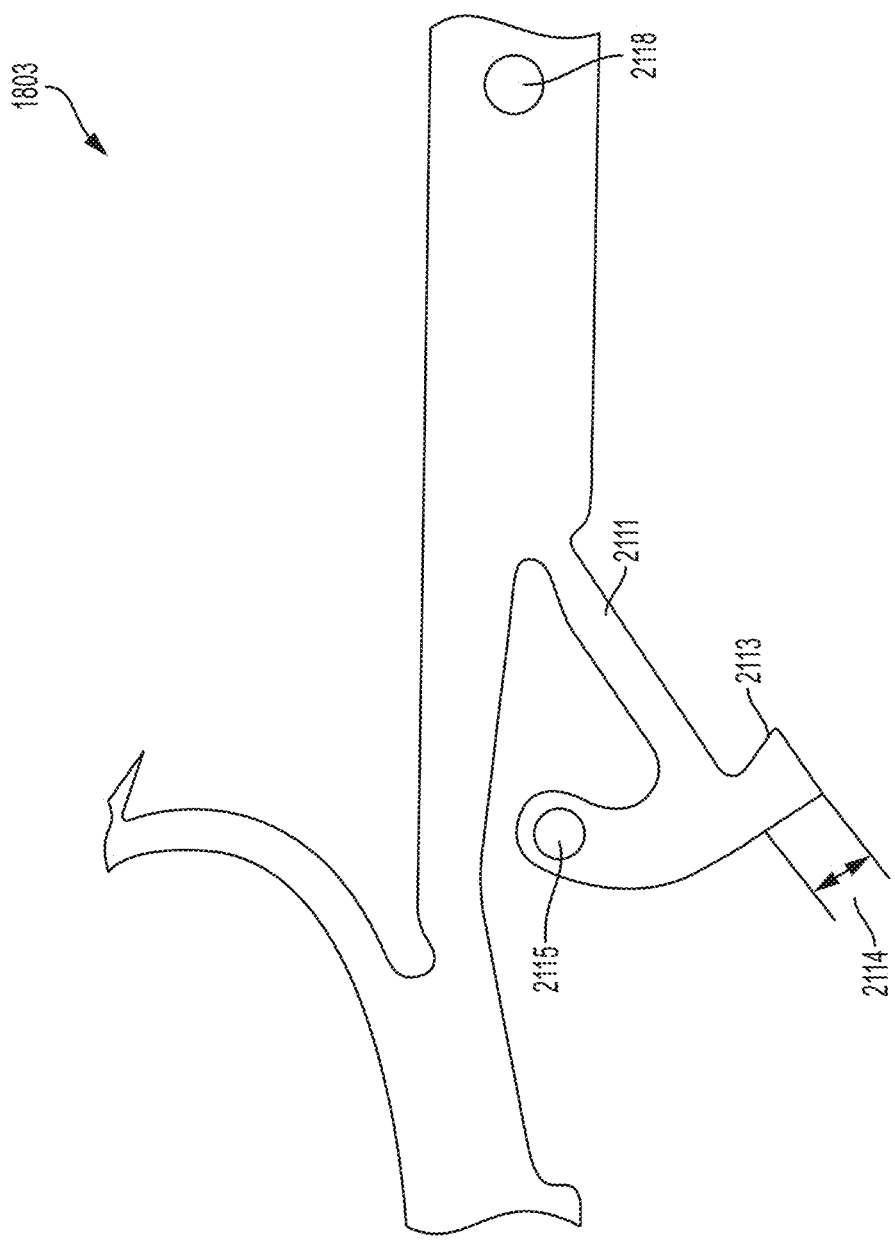
FIG. 21 depicts a detail view of another illustrated anchor stop feature

Additionally or alternatively, as shown in FIG. 21, an embodiment may include an anchor stop feature 1803 attached with one strut to an anchor zone having a negative deployment angle 2113. In a further embodiment, the anchor stop feature 1803 may include one or more deployment holes 2115. Thus, as illustrated in FIG. 21, an embodiment may include a typical anchor stop feature 1803, a first connecting strut 2111, a deployment angle 2113, an anchor stop feature height 2114, an anchor stop deployment hole 2115, and an anchor zone suture routing hole 2118.

Figure 22:
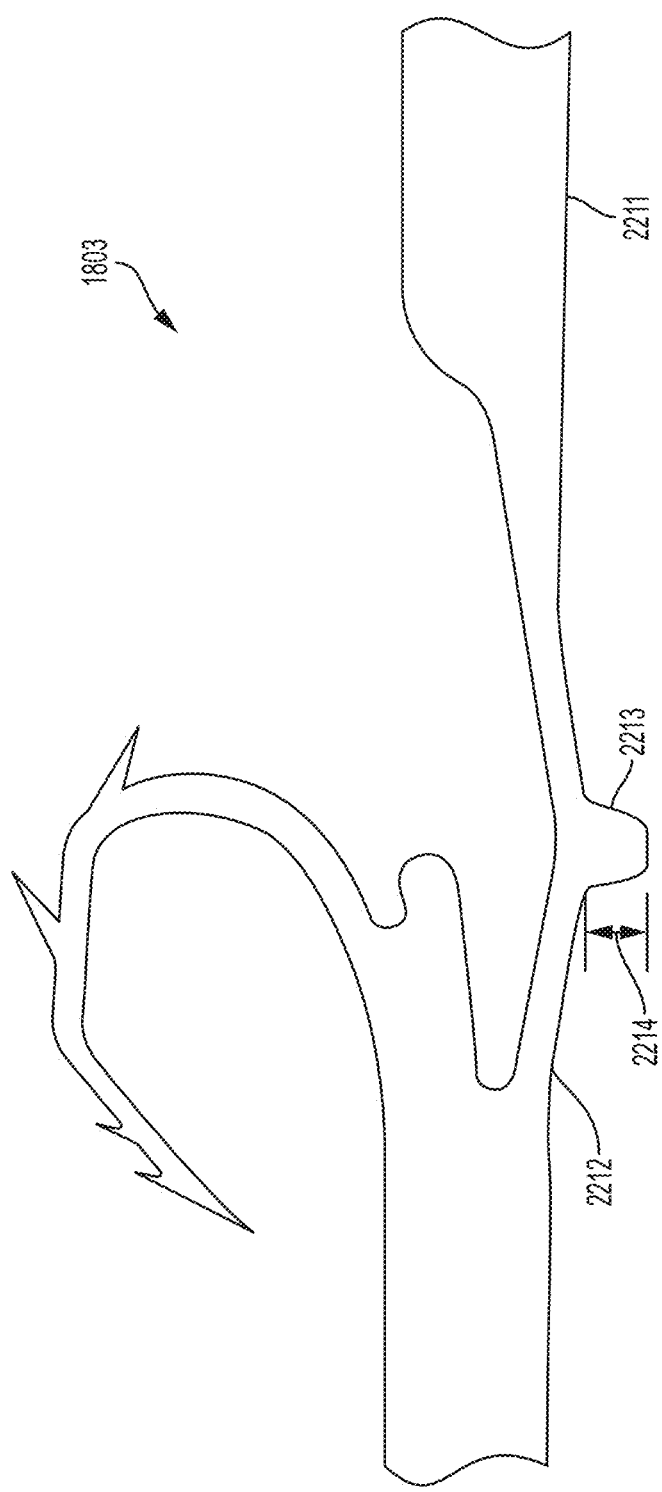
FIG. 22 depicts a detail view of another illustrated anchor stop feature.
Figure 23:
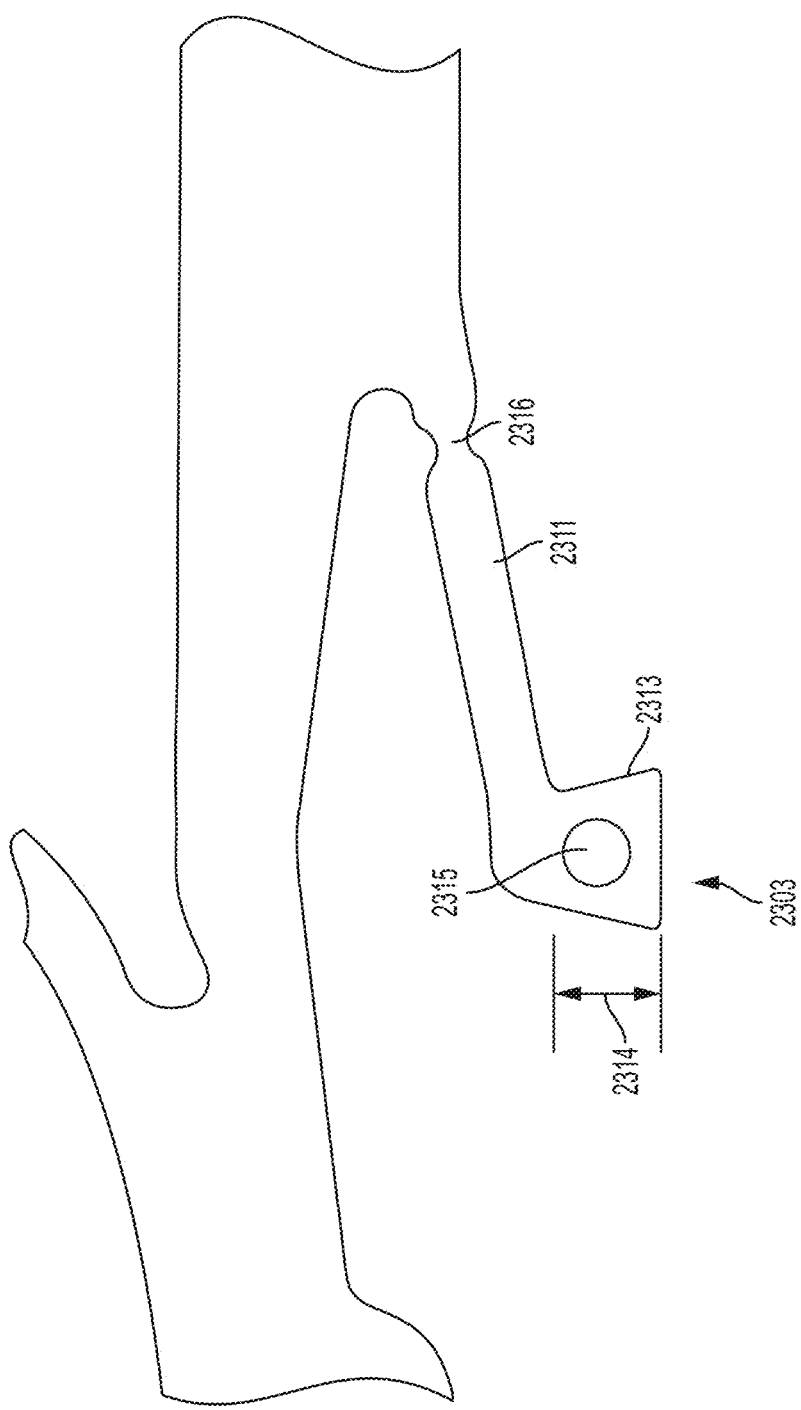
FIG. 23 depicts a detail view of another illustrated anchor stop feature.

FIG. 22 depicts another illustrative embodiment of an anchor stop feature 1803. As shown, the anchor stop feature 1803 may include a first connecting strut 2211, a second connecting strut 2212, a deployment angle 2213, and an anchor stop feature height 2214. Additionally or alternatively an embodiment, as shown in FIG. 23, may include an anchor stop feature 1803 with a weak point 2216 to direct an anchor stop disconnection at a certain point. Thus, an embodiment, as shown in FIG. 23, may include a first connecting strut 2311, a deployment angle 2313, an anchor stop feature height 2314, an anchor stop deployment hole 2315, and a weak point of the anchor stop feature strut 2316.

Figure 24:
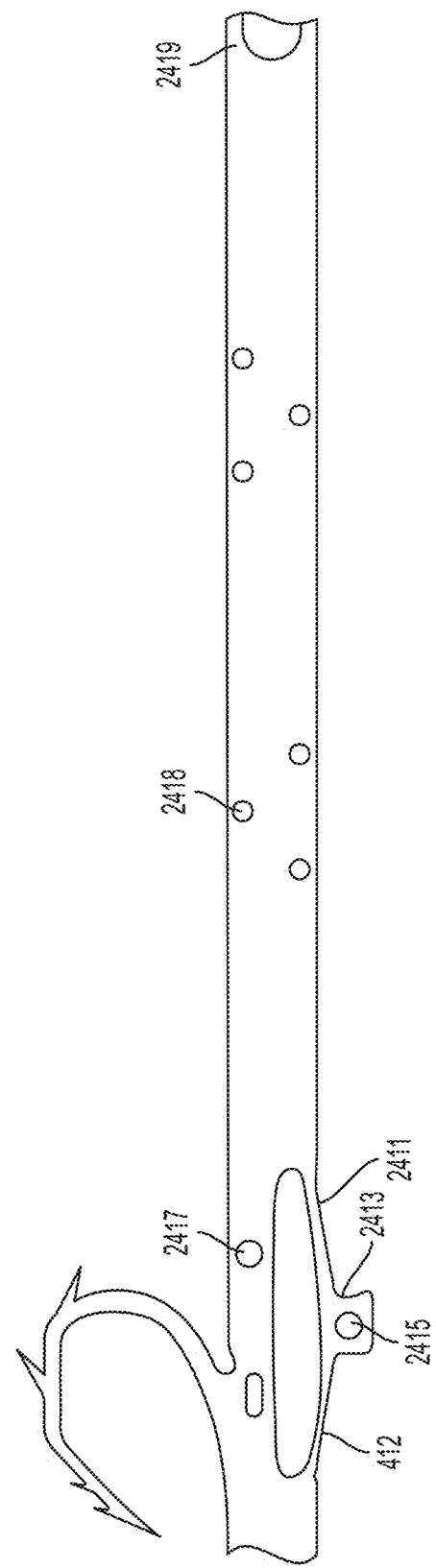
FIG. 24 depicts another illustrated anchor stop feature and an illustrated harpoon.

Referring now to FIG. 24, an embodiment may include an active anchor stop feature with activation holes 2417 on the anchor zone rail. Thus, as shown in FIG. 24, an illustrated embodiment may include a first connecting strut 2411, a deployment angle 2413, an anchor stop feature deployment hole 2415, an activation hole 2417 for transforming the suture direction from horizontal to vertical, an anchor zone suture routing hole 2418, and an anchor zone deployment hole 2419.

The anchor stop may be used to position the anchor zone in relation to the hypotube and act as a locking feature that prevent unintentional movement and activation of the anchor zone. In some embodiments, the feature may be passive and activated by pulling, and therefore bending, the zone. In further embodiments the feature may be an activation pulley that prevents the anchor zone from bending and exiting the hypotube. In some embodiments, the anchor stop is located on the ventricle side of the anchor zone. In other embodiments, the anchor stop is located on the atrial side of the anchor zone.

Figure 25:
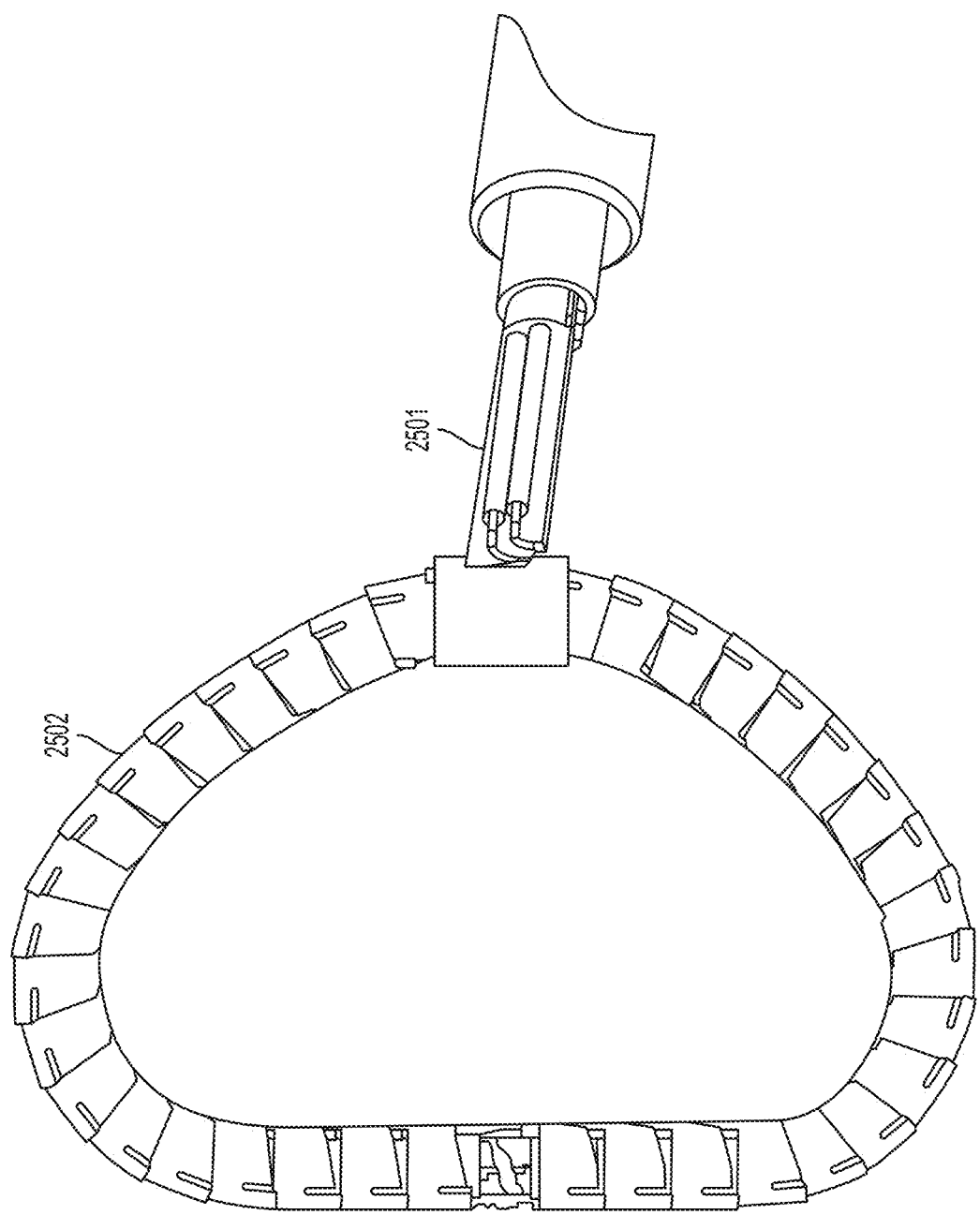
FIG. 25 depicts a perspective view of an illustrative non-deployed anchor parked adjacent to a deployment window.

As discussed herein, an embodiment may take the shape of the memory hypotube and may have an operable geometry, for example, an annular and/or D shaped geometry (as shown in FIG. 5). Referring now to FIG. 25, a perspective view of an illustrative distal end of a delivery system 2501 with an implant interface member connected to the tricuspid ring 2502 is shown.

Figure 26:
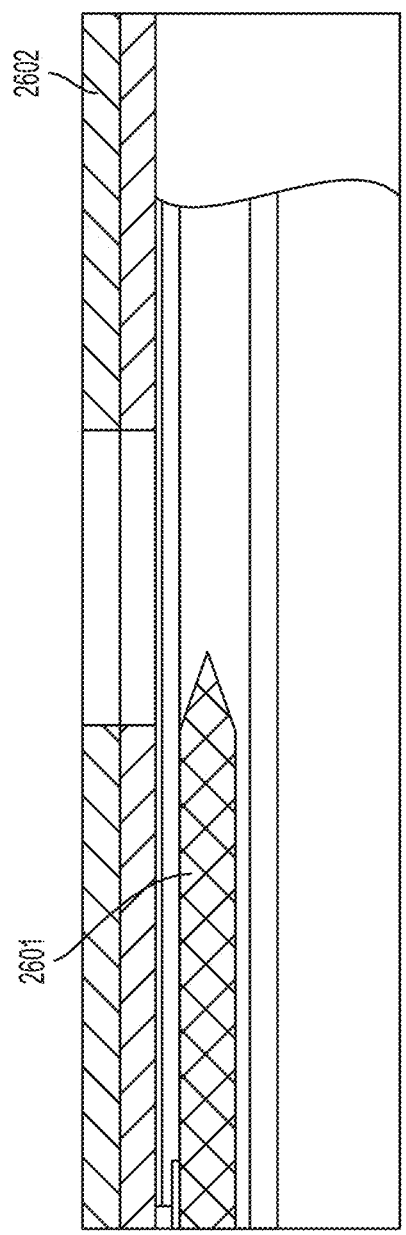
FIG. 26 depicts an illustrative view of a non-deployed anchor.
Figure 27:
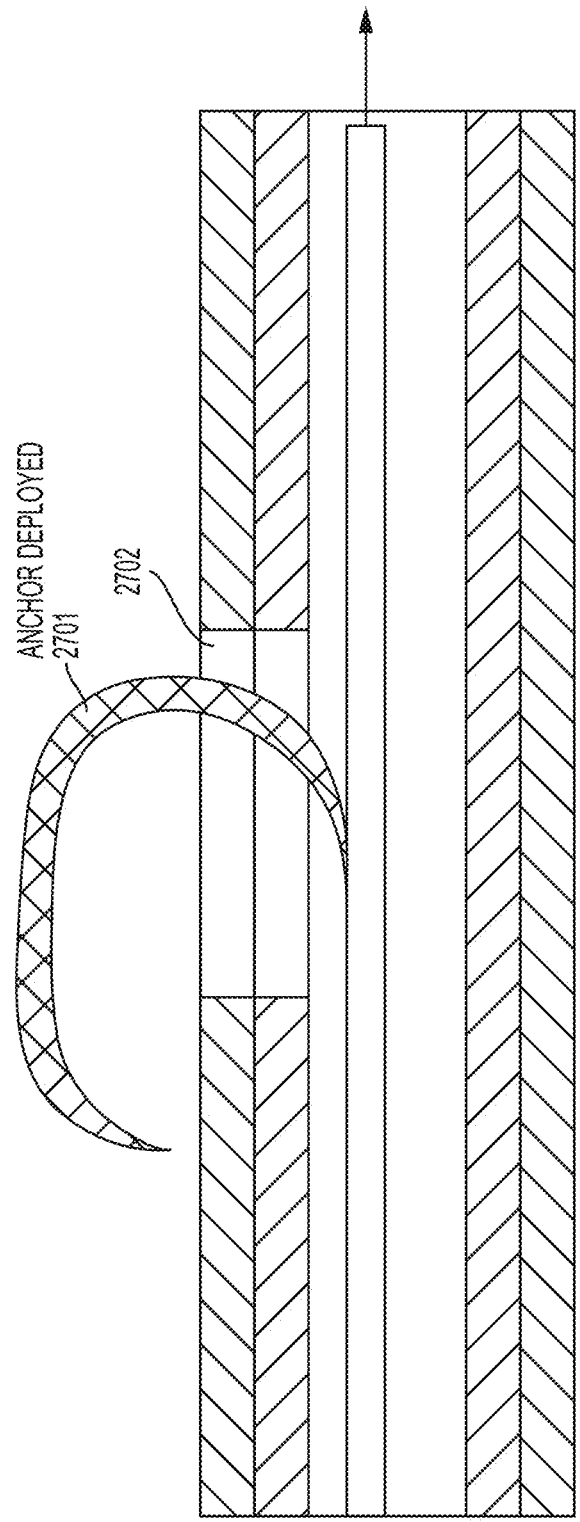
FIG. 27 depicts an illustrative view of a deployed anchor.
Figure 28:
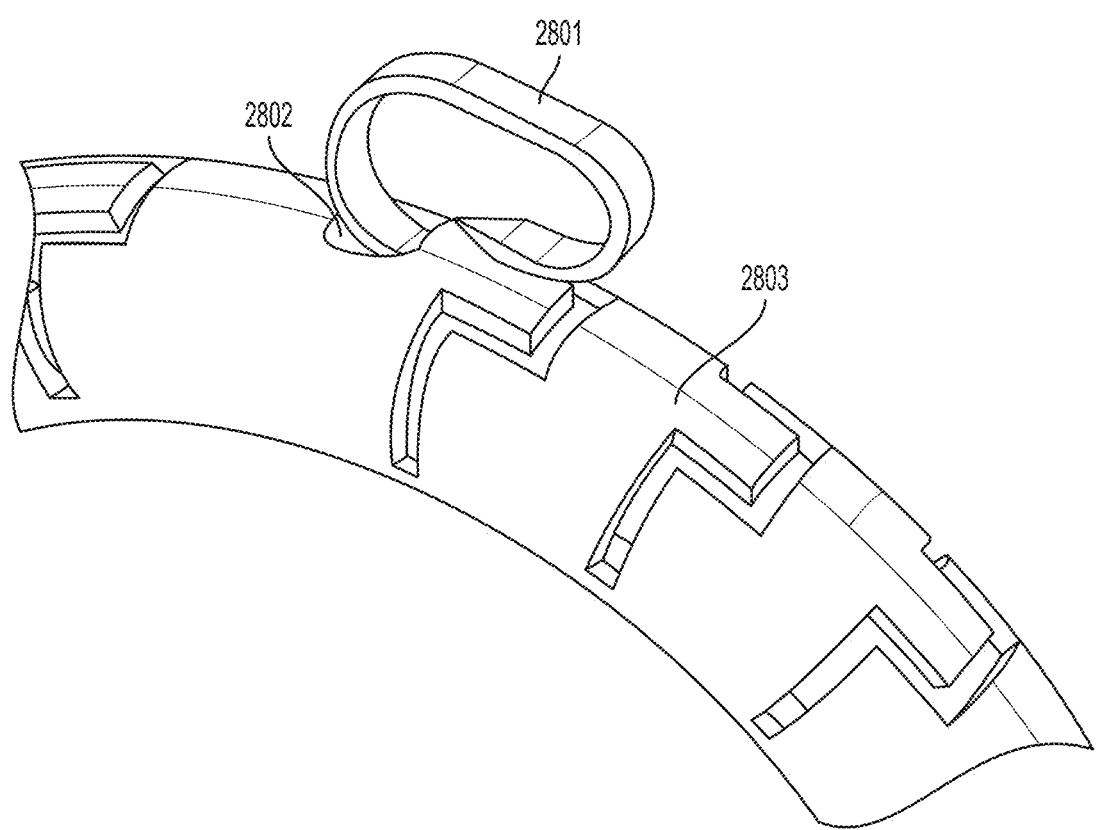
FIG. 28 depicts a detail view of a segment of the tricuspid ring with a deployed anchor.

FIGS. 26 and 27 illustrate a general view of one or more typical anchors in an initial and deployed position, respectively. In FIG. 26, the anchor 2601 is tucked within the hollow laser cut tube 2602 under its respective deployment window. In FIG. 27, a non-limiting illustration shows a deployed anchor 2701 after it has been deployed from its respective deployment window 2702. Further detail of a deployed anchor 2701 is shown in FIG. 28, which depicts a magnified view of a segment of the tricuspid ring 2803 that includes a deployment window 2802 (see also 602 of FIG. 6) and a deployment anchor 2801.

Figure 29:
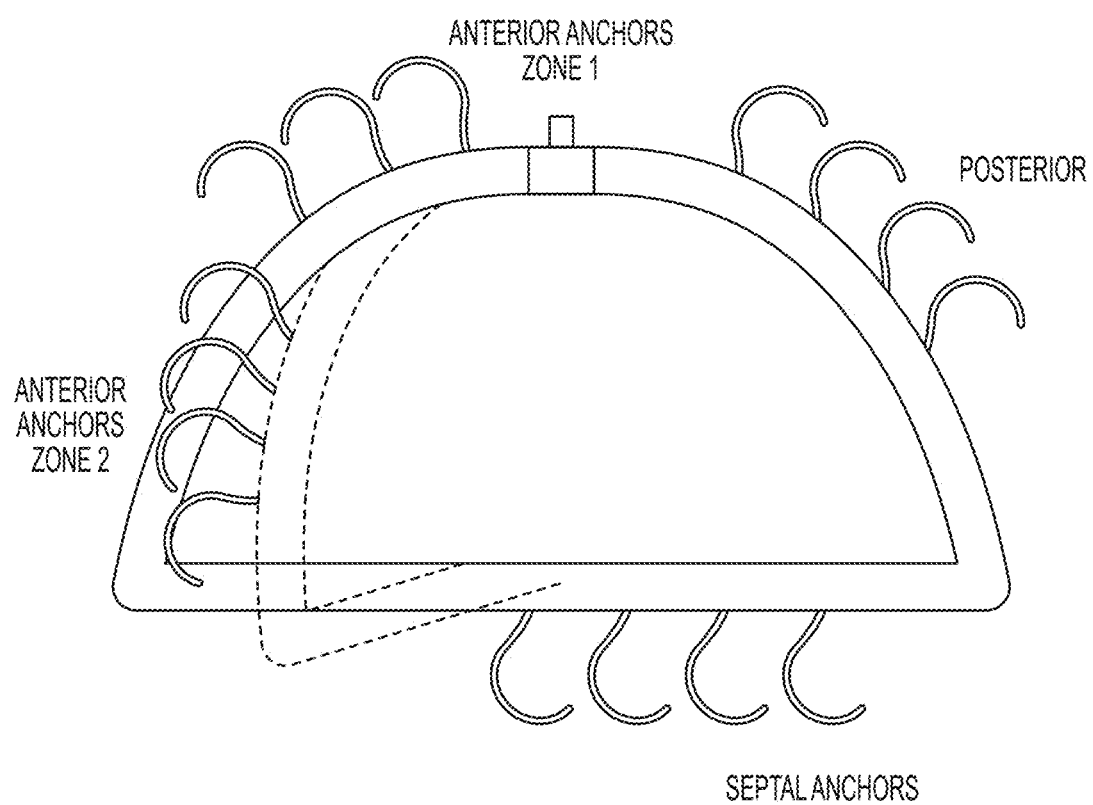
FIG. 29 depicts an illustrative initial geometry of a tricuspid ring.

Referring now to FIG. 29, an embodiment is depicted that includes an initial geometry of the tricuspid ring when deployed from the delivery system (e.g., the solid lines) and the geometry of the tricuspid ring after deployment of all anchors (e.g., the dashed lines). In some embodiments the tricuspid ring may comprise a first anterior zone, a second anterior zone, a posterior zone, and a septal zone. Thus, as shown in FIG. 29, the solid lines may depict the initially deployed geometry, while the dashed lines may depict one possible final geometry after the anterior leaflet (e.g., at zone 2) has been transferred to reduce the anterior septal height.

Figure 30:
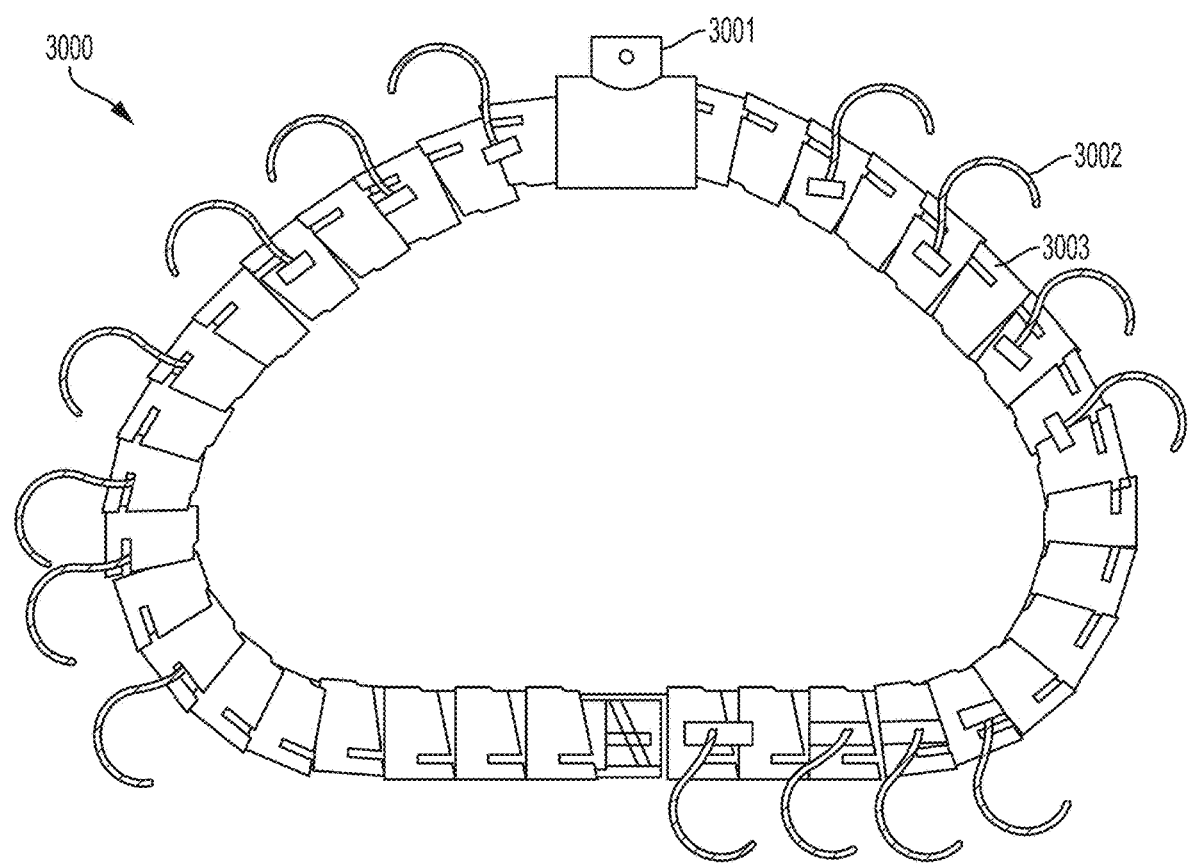
FIG. 30 depicts an illustrative tricuspid ring in a "D" shape geometry.

FIG. 30 shows a perspective view of an embodiment wherein a tricuspid ring 3000 may include one or more snap mechanisms 3001 that connect a proximal and distal end of the laser cut hollow tube to create a geometric shape (e.g., a "D" shape). In a further embodiment, the geometrically shaped tricuspid ring may include one or more anchors 3002 which can be deployed from the deployment windows 3003.

Figure 31:
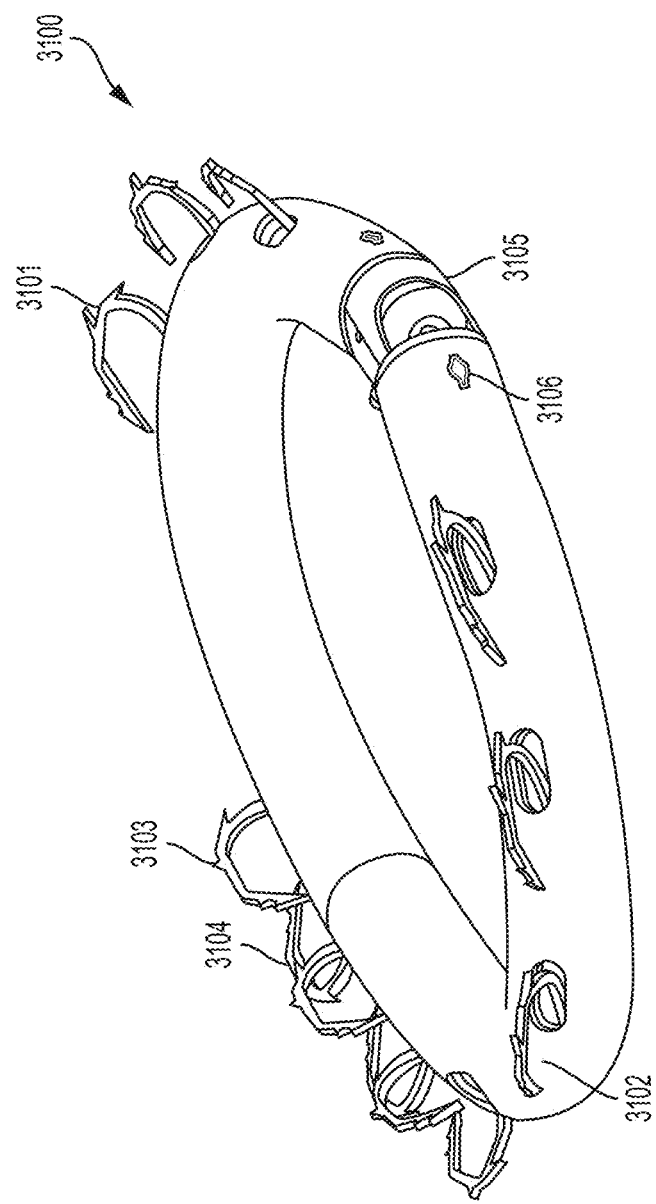
FIG. 31 depicts another illustrative tricuspid ring with a snap mechanism.

FIG. 31 shows a perspective view of an embodiment wherein a tricuspid ring 3100 includes a snap mechanism 3105 that connects a proximal and a distal end of the laser cut hollow tube (700 of FIG. 7) to create a shape that mimics the native shape of the tricuspid annulus. In a further embodiment, the tricuspid ring 3100 may also include one or more anchors deployed from the one or more deployment windows. In one embodiment, as shown in FIG. 31, the anchors may exit from the deployment windows at an angle within a range of about 30 degrees to the horizontal plane to about 75 degrees to the horizontal plane.

Thus, as shown in FIG. 31, an embodiment may include a tricuspid ring 3100, an anterior zone 3101 where the anchors exit from the tricuspid ring at an angle to provide anchoring forces in both the radial and axial directions, a posterior zone 3102 where the anchors exit from the tricuspid ring at an angle to provide anchoring forces in both the radial and axial directions, a first septal zone 3103 where the anchors exit the ring at an angle to provide anchoring forces in both the radial and axial directions, a second septal zone 3104 where the anchors exit from the ring at an angle to provide anchoring forces in both the radial and axial directions, a snapping mechanism (e.g., closure mechanism) 3105, and a suture pin to provide a rotational pin for the sutures 3106.

Figure 32:
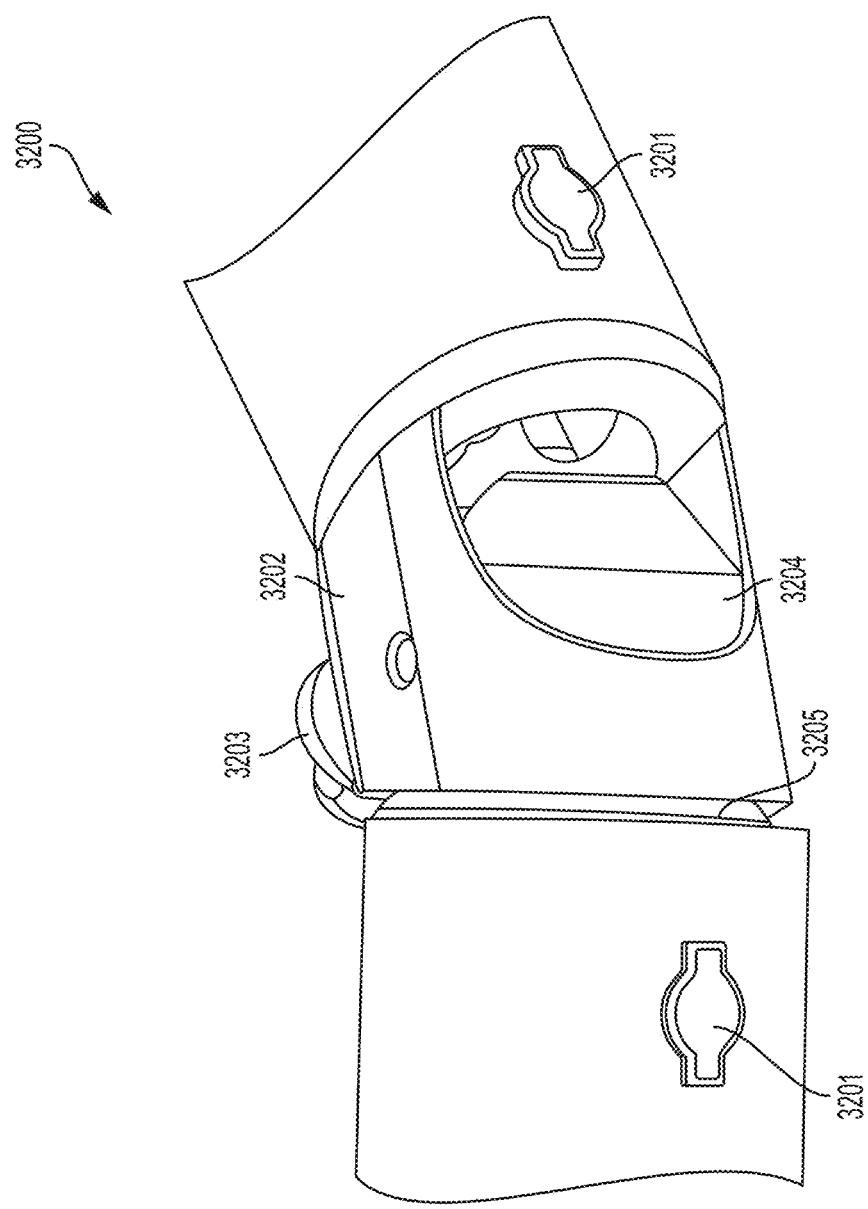
FIG. 32 depicts a detail view of an illustrative snapping mechanism in a closed configuration.

FIG. 32 shows a perspective view of an embodiment wherein a snapping mechanism 3200 is utilized to secure the tricuspid ring in a closed configuration. Thus, as shown in FIG. 32, an embodiment may include a snapping mechanism 3200, a suture pin (e.g., attachment of female and male parts of the ring tube) 3201, a female part of the snapping mechanism 3202, a pivot pin (e.g., attachment of the snapping mechanism to the delivery system with a safety wire) 3203, a cover part (e.g., a component to hold the nitinol disk that snaps the male part into the female) 3204, and a male part of the snapping mechanism 3205.

Figure 33:
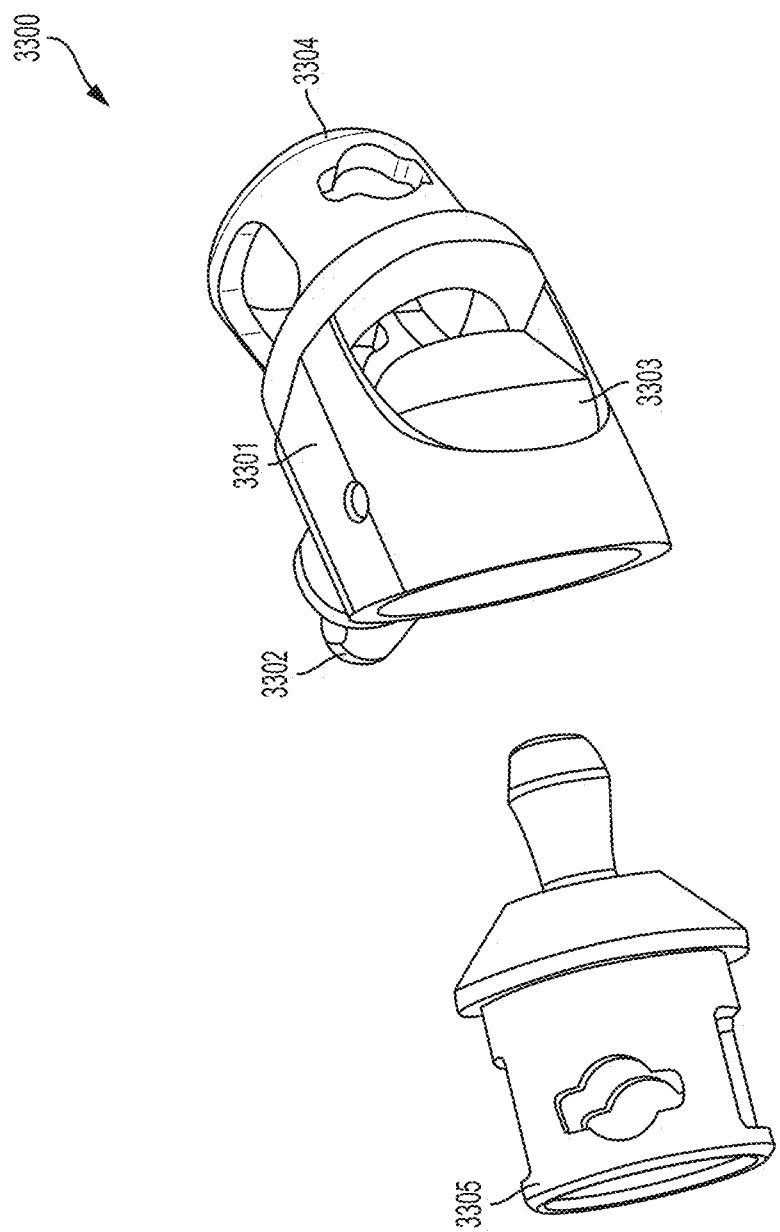
FIG. 33 depicts a detail view of an illustrative snapping mechanism in an open configuration.

FIG. 33 shows a detailed view of an embodiment, wherein the snapping mechanism 3300 is in an open configuration. Again, similar to embodiments discussed herein, the snapping mechanism 3300 is utilized to secure the tricuspid ring in a closed configuration. Thus, as shown in FIG. 33, an embodiment may include a snapping mechanism 3300, a female part of the snapping mechanism 3301, a pivot pin (e.g., attachment of the snapping mechanism to the delivery system with a safety wire) 3302, a cover part (e.g., a component to hold the Nitinol disk that snaps the male part into the female) 3303, a cup (e.g., an interface of the female to the ring tube) 3304, and a male part of the snapping mechanism 3305.

Figure 34:
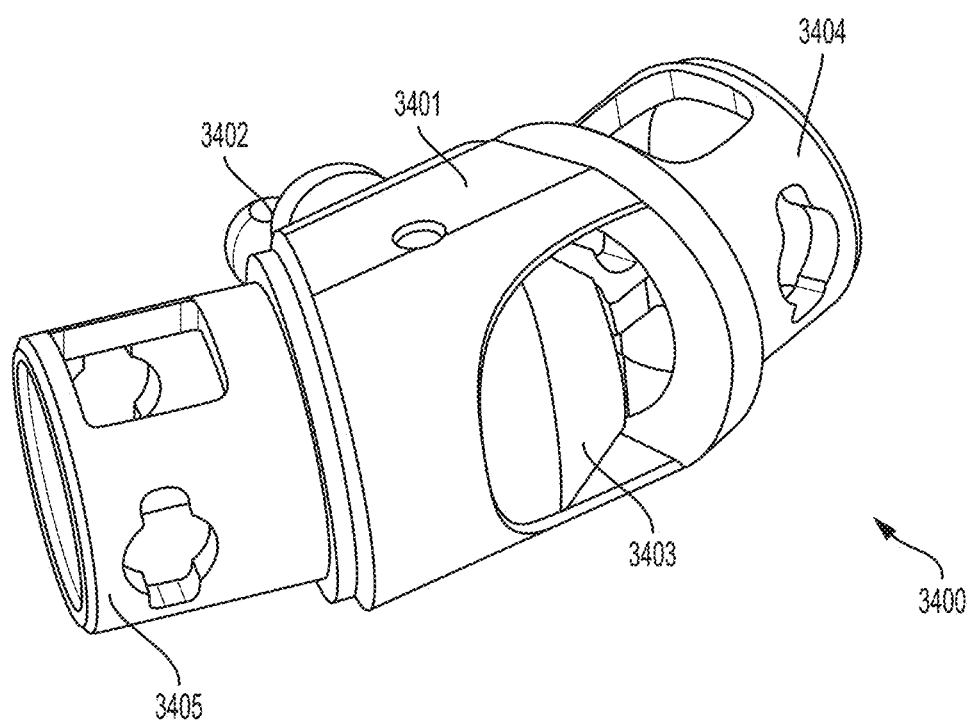
FIG. 34 depicts an isolated detail view of an illustrative snapping mechanism in a closed configuration.

A detailed view of an embodiment where the snapping mechanism is in a closed configuration is shown in FIG. 34. Similar to embodiments discussed herein, the snapping mechanism 3400 is utilized to secure the tricuspid ring in a closed configuration. Thus, as shown in FIG. 34, an embodiment may include a snapping mechanism 3400, a female part of the snapping mechanism 3401, a pivot pin (e.g., attachment of the snapping mechanism to the delivery system with a safety wire) 3402, a cover part (e.g., part to hold the Nitinol disk that snaps the male part into the female) 3403, a cup (e.g., an interface of the female to the ring tube) 3404, and a male part of the snapping mechanism 3405.

Figure 35:
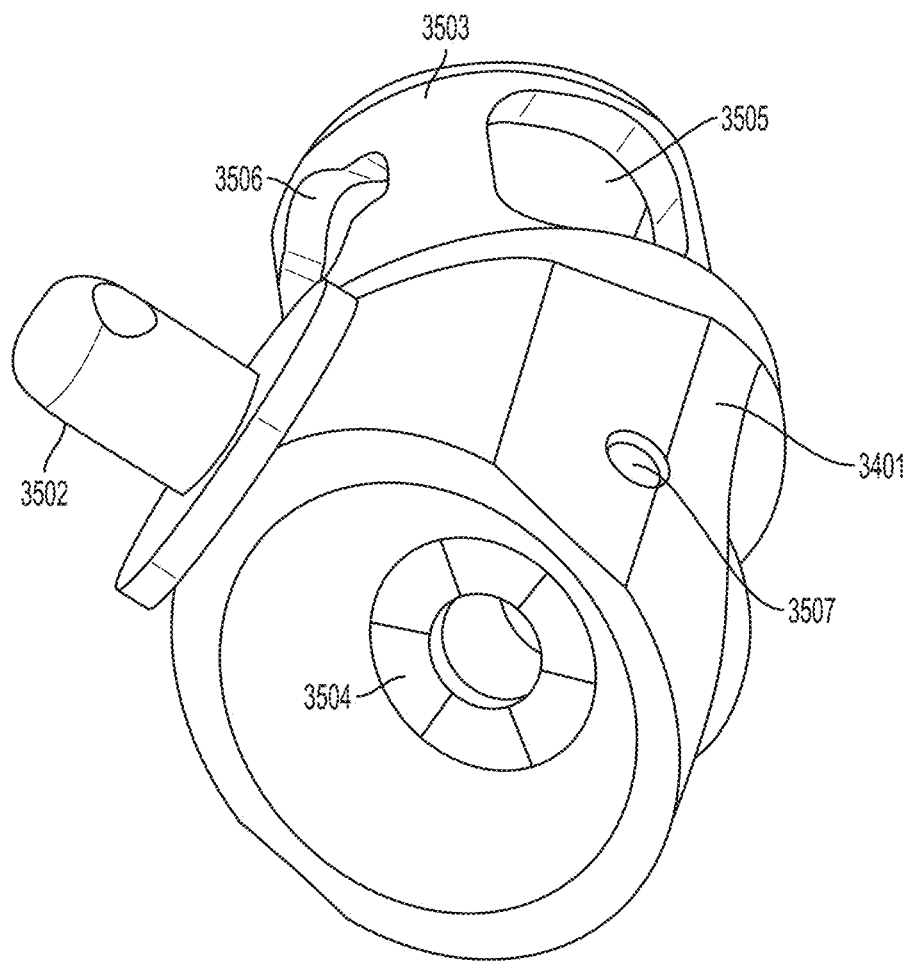
FIG. 35 depicts an isolated detail view of an illustrative female snapping mechanism.

A detailed view of the female part 3401 of the snapping mechanism 3400 according to one embodiment is shown in FIG. 35. As shown in FIG. 35, the female part 3401 of the snapping mechanism 3400 may include, a pivot pin (e.g., an attachment of the snapping mechanism to the delivery system with a safety wire) 3502, a cup (e.g., an interface of the female to the ring tube) 3503, a nitinol disk for locking the snap into position 3504, a window for suture routing 3505, a window for a suture pin 3506, and a gold marker 3507.

Figure 36:
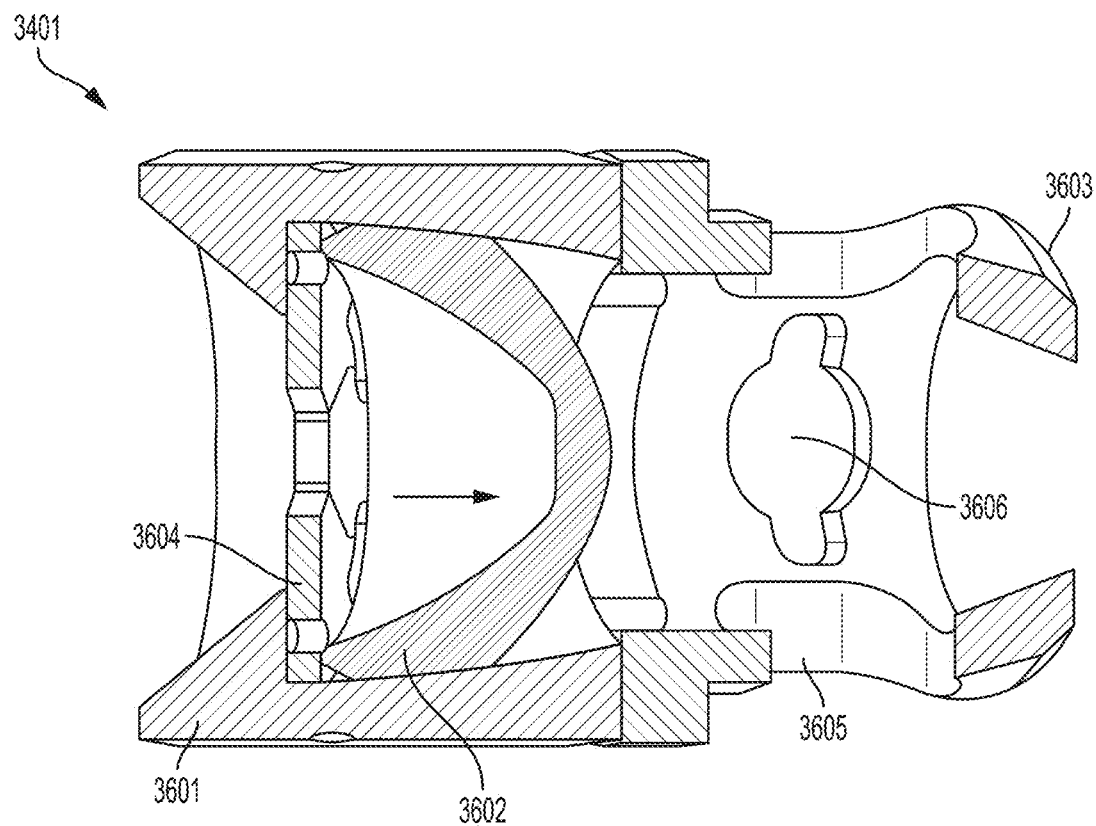
FIG. 36 depicts a cross-sectional view of an illustrative female snapping mechanism.

FIG. 36 shows an illustrative cross section of the female part 3401 of the snapping mechanism 3400 according to an embodiment. As shown in FIG. 36, the female part 3401 of the snapping mechanism 3400 may include a pivot pin (e.g., an attachment of the snapping mechanism to the delivery system with a safety wire) (not shown), a cover that holds a nickel titanium (Ni—Ti) disk 3602, a cup (e.g., an interface of the female to the ring tube) 3603, a nitinol disk for locking the snap into position (tongues can open only in one direction to prevent un-intentional unsnapping) 3604, a window for suture routing 3605, and a window for a suture pin 3606.

Figure 37:
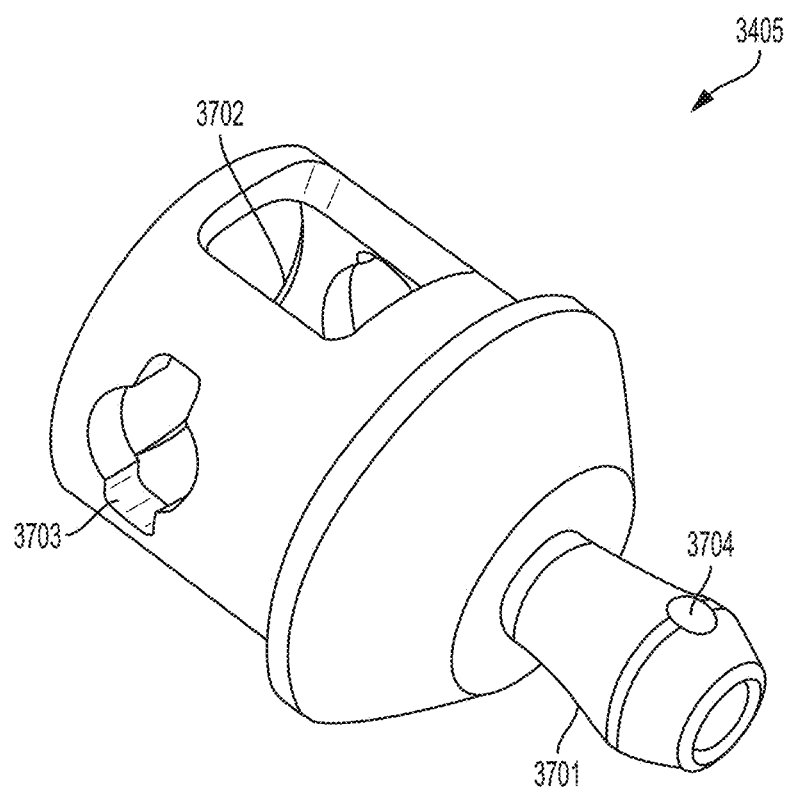
FIG. 37 depicts a detail view of an illustrative male snapping mechanism.

A detailed view of the male part 3405 of the snapping mechanism according to an embodiment is shown in FIG. 37. As shown in FIG. 37, the male part 3405 of the snapping mechanism 3400 may include a male cone 3701 to allow smooth entrance and locking of the male within the female, a least one window for suture routing 3702, at least one window for a suture pin 3703, and at least one protrusion 3704 upon the suture pin.

Figure 38:
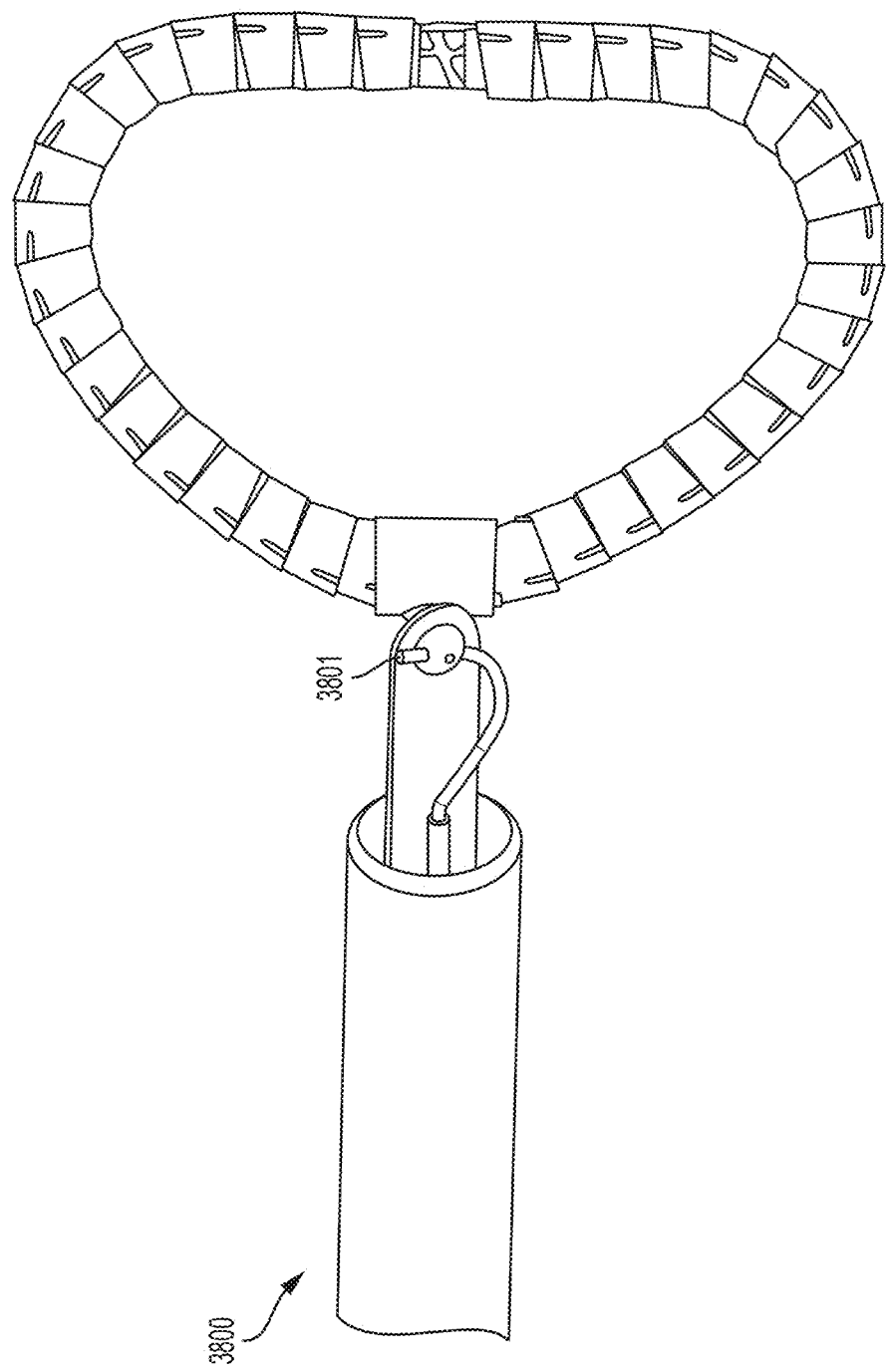
FIG. 38 depicts a view of an illustrative delivery system that is connected to a snapped ring.

Turning now to FIG. 38, a detailed view of a distal end of a delivery system 3800 is shown. In one embodiment, the distal end of the delivery system 3800 may interface with the tricuspid ring assembly. For example, FIG. 39 illustrates a detailed view of the distal end 3901 of the delivery system 3900, wherein the delivery system interfaces with the tricuspid ring assembly and the tricuspid ring 3950.

Figure 39:
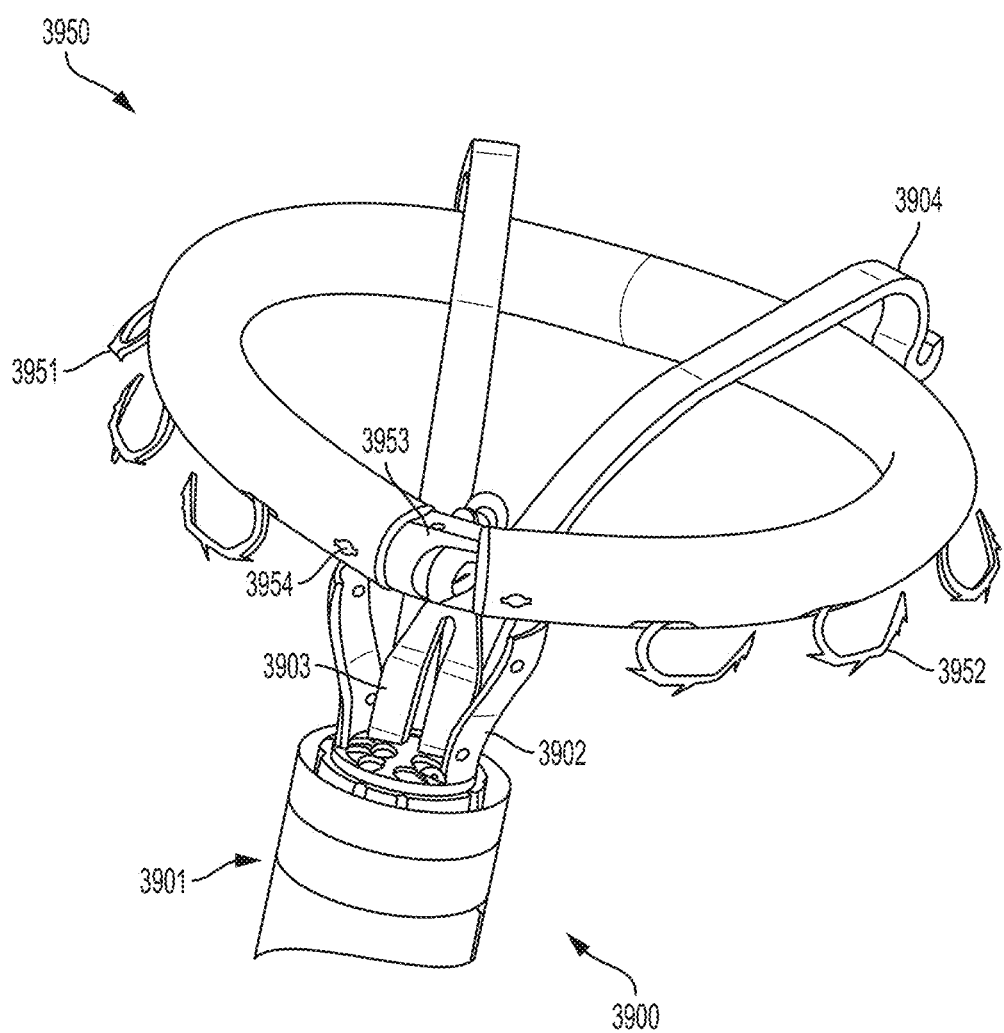
FIG. 39 depicts another view of an illustrative delivery system that is connected to a ring with deployed anchors with the stabilizing tool in the center.

As shown in FIG. 39, the delivery system 3900 may interface with a tricuspid ring 3950 that may have an anterior zone 3951 where anchors exit the ring at an angle to provide anchoring forces in both the radial and axial direction. The tricuspid ring 3950 may also have a posterior zone 3952 where anchors exit the tricuspid ring at an angle to provide anchoring forces in both the radial and axial direction, a snapping mechanism (e.g., closure mechanism) 3953, and a suture pin to provide a rotation pin for the sutures 3954. the delivery system 3900 may include a distal end of the guiding catheter 3901, a stabilizing mechanism to ensure ring stabilization during an implantation procedure 3902, a delivery system (DS) tongue (e.g., ring interface device) 3903, and a stabilizing tool 3904.

Figure 40:
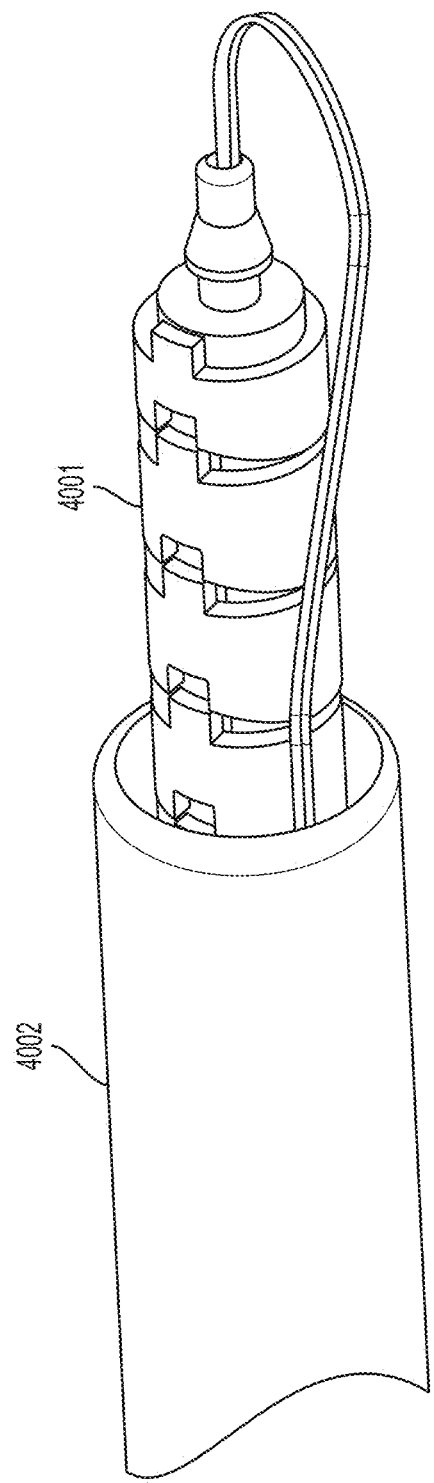
FIG. 40 depicts an illustrative view of the delivery system.
Figure 41:
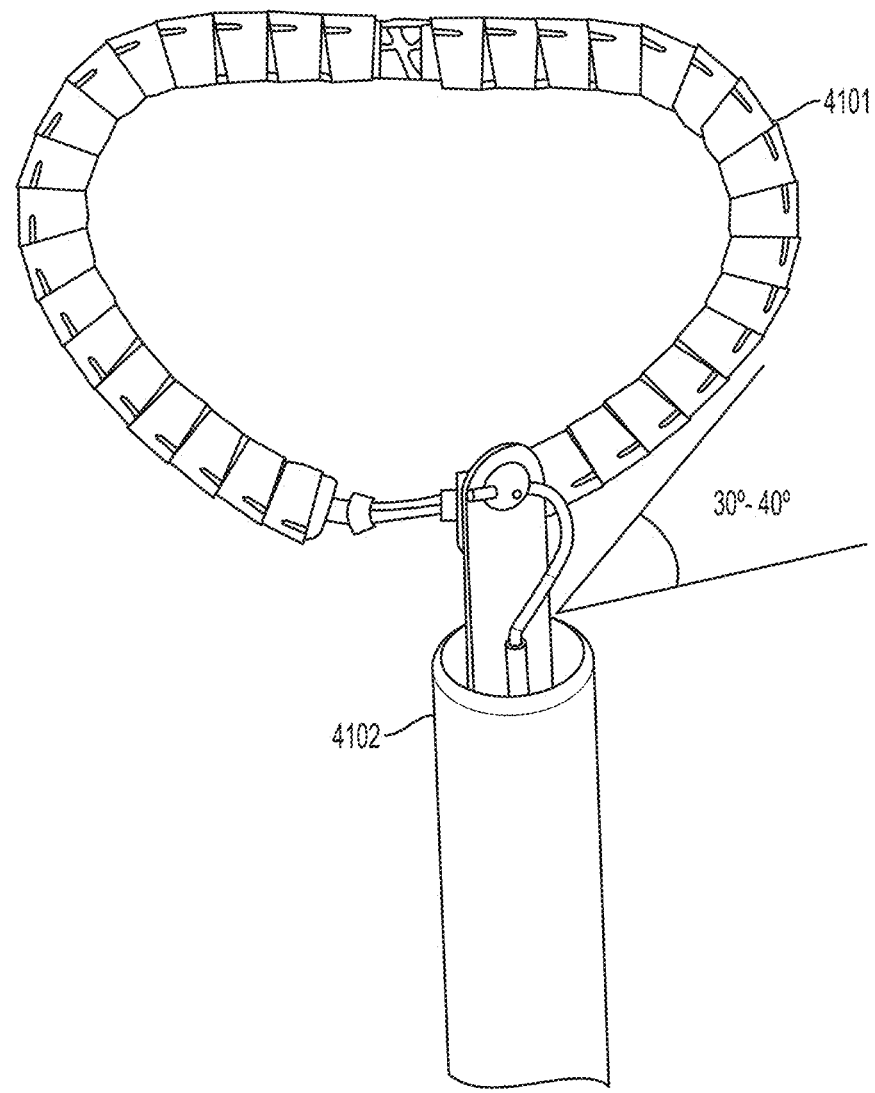
FIG. 41 depicts another illustrative view of the delivery system connected to a deployed ring.
Figure 42:
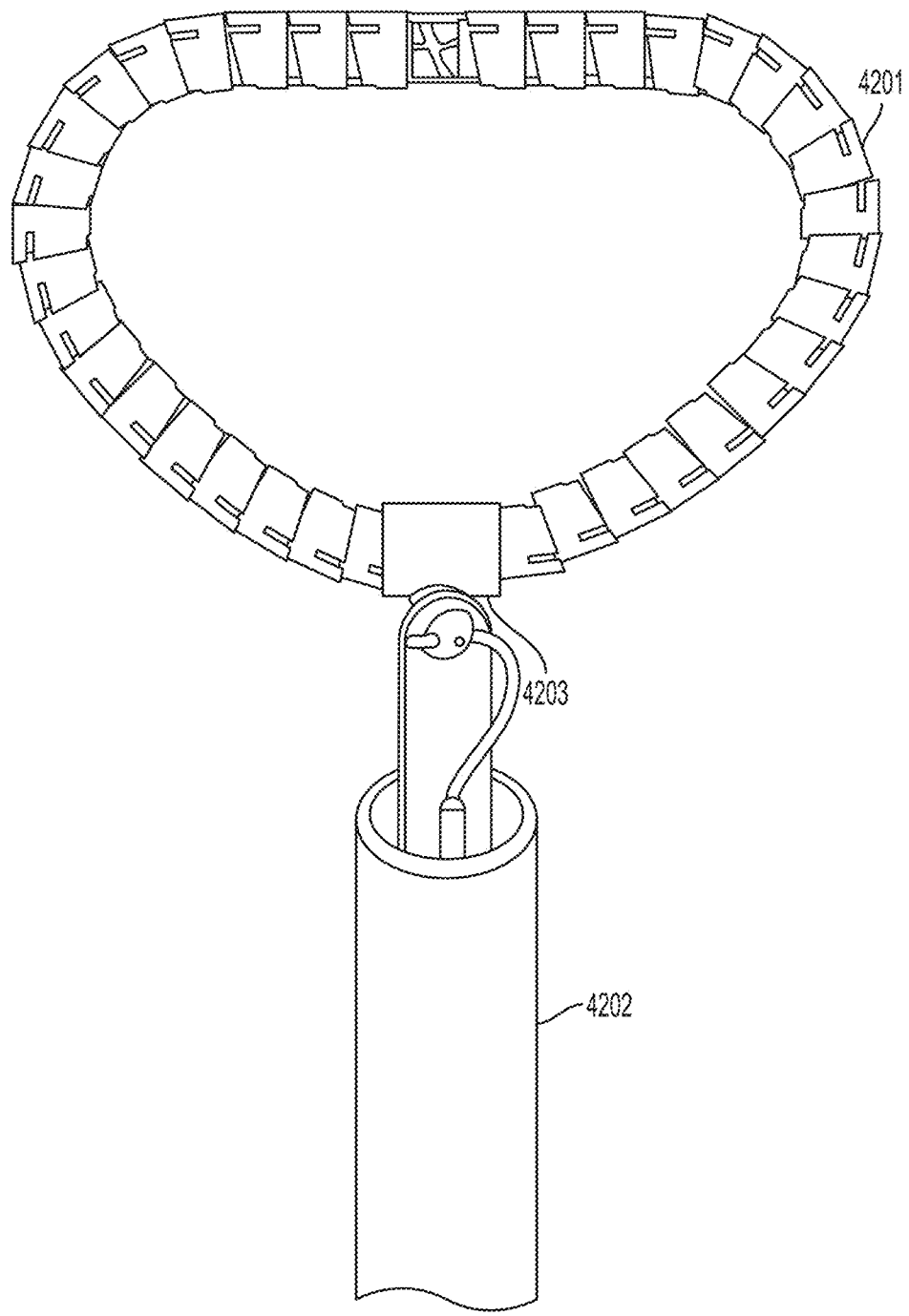
FIG. 42 depicts another illustrative view of the delivery system that is connected to a ring.

FIGS. 40-42 depict various views of the delivery system during the beginning of the deployment of the tricuspid ring from the delivery system. In one embodiment, and as shown in FIG. 40, the tricuspid ring 4001 may exit the delivery system 4002 in a linear shape. Once the tricuspid ring 4001 exits the delivery system, it may in some embodiments be formed into a ring-like shape using methods disclosed herein, and as shown in FIGS. 41 and 42. FIG. 41 shows an embodiment in which the tricuspid ring 4101 is formed using the delivery system 4102. In some embodiments, and as shown in FIG. 41, the tricuspid ring 4101 may be between about 30° and about 40° from a plane normal to the delivery system 4102. FIG. 42 shows an embodiment in which the tricuspid ring 4201 is formed and the snapping mechanism (e.g., closure mechanism) 4203 secures the ring in the proper geometry. In some embodiments, such as that shown in FIG. 42, the delivery system 4202 may be used to move or modify the shape or location of the tricuspid ring 4201.

Figure 43:
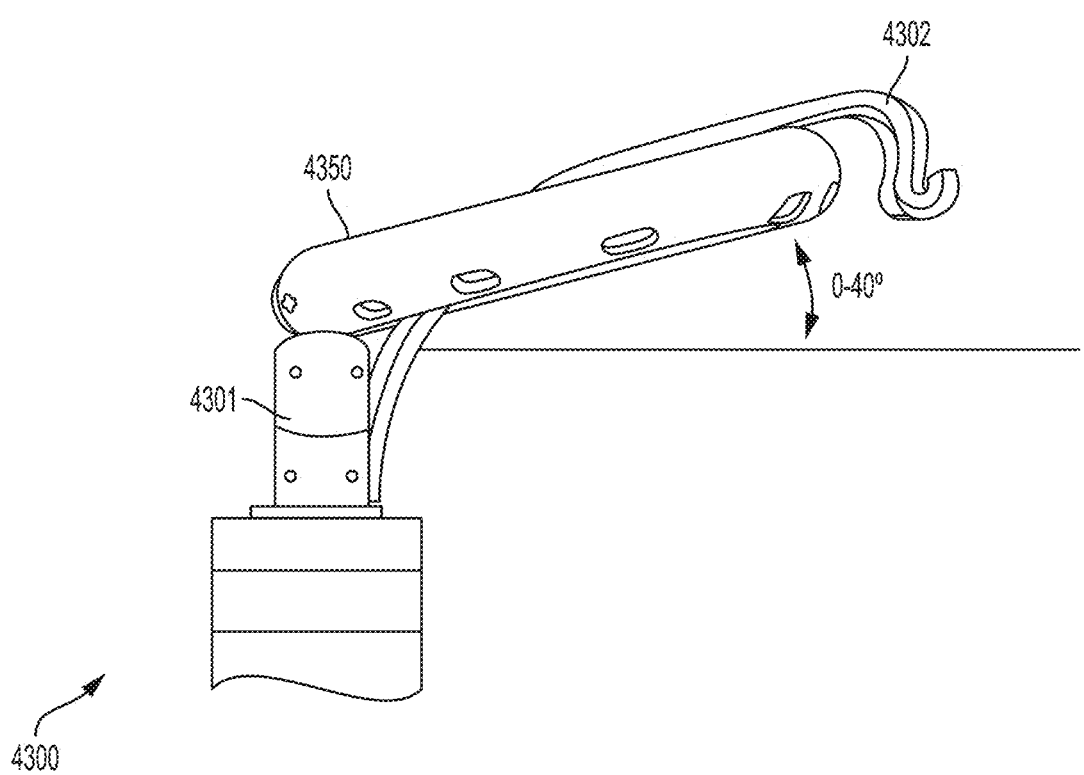
FIG. 43 depicts another illustrative view of a hinge system associated with the delivery system and a stabilizing tool.

In some embodiments, such as that shown in FIG. 43, the delivery system 4300 may interface with a tricuspid ring

4350. The tricuspid ring 4350 may also have a posterior zone where anchors exit the tricuspid ring (not shown) at an angle to provide anchoring forces in both the radial and axial direction, a snapping mechanism (e.g., closure mechanism) (not shown), and a suture pin to provide rotation pin for the sutures (not shown). The delivery system 4300 may include a distal end of the guiding catheter (not shown), a stabilizing mechanism 4301 to ensure ring stabilization during an implantation procedure, a delivery system (DS) tongue (e.g., ring interface device) (not shown), and a stabilizing tool 4302. As shown, the plane of the tricuspid ring 4350 may be between about 0° and about 40° removed from the plane of the tricuspid valve after rotation around the hinge.

Figure 44:
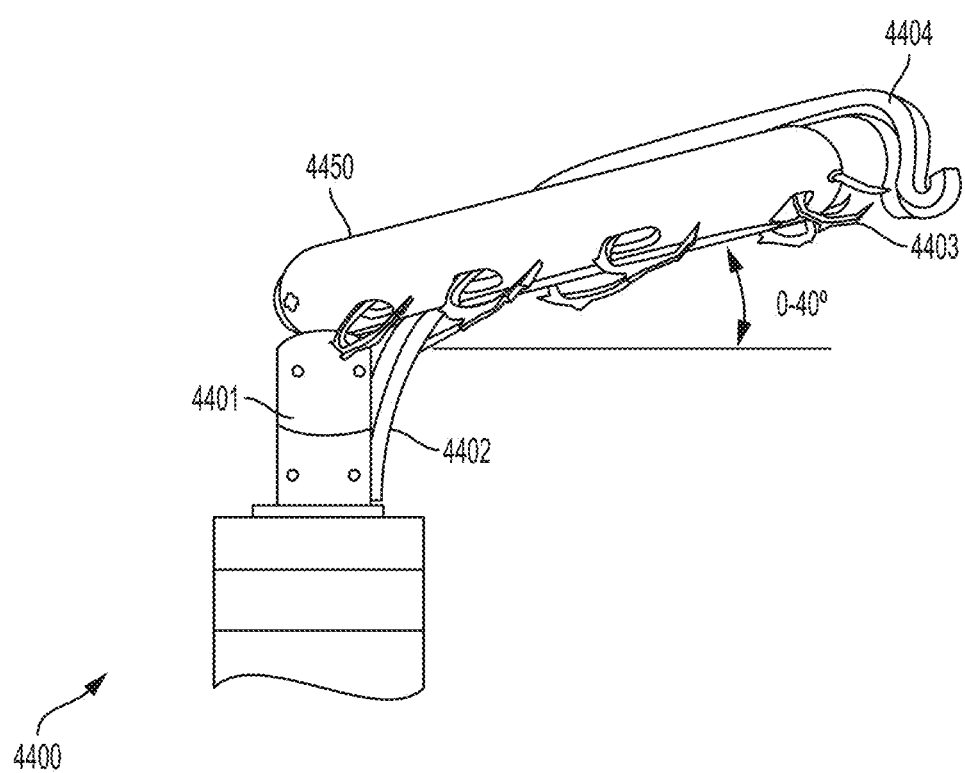
FIG. 44 depicts an illustrative view of a delivery system connected to a fully deployed ring and stabilizing tool.

In another embodiment, as shown in FIG. 44, the plane of the ring may be parallel or slightly angled (e.g., from about 0° to about 40°) to the plane of the tricuspid valve after rotation around the hinge. Thus, an embodiment may utilize a trans-apical approach (i.e., pulling the ring to the tissue). In some embodiments, the delivery system 4400 may interface with a tricuspid ring 4450 that may have an anterior zone where anchors (not shown) exit the ring at an angle to provide anchoring forces in both the radial and axial direction. The tricuspid ring 4450 may also have a posterior zone 4403 where anchors exit the tricuspid ring at an angle to provide anchoring forces in both the radial and axial direction, a snapping mechanism (e.g., closure mechanism) (not shown), and a suture pin to provide a rotation pin for the sutures (not shown). The delivery system 4400 may include a distal end of the guiding catheter 4401, a stabilizing mechanism 4402 to ensure ring stabilization during an implantation procedure, a delivery system (DS) tongue (e.g., ring interface device) (not shown), and a stabilizing tool 4404. As stated, the ring orientation in relation to the delivery system 4400 may be in a range of about 0 degrees to about 40 degrees "above" the horizontal plane. As discussed herein, this approach is trans-apical, thus pulling the ring to the tissue. In a further embodiment, the ring orientation may be in a range of about 0 degrees to about 40 degrees "above" the horizontal plane of the delivery system. FIG. 44 depicts the embodiment of FIG. 43 with the anchors deployed.

Figure 45:
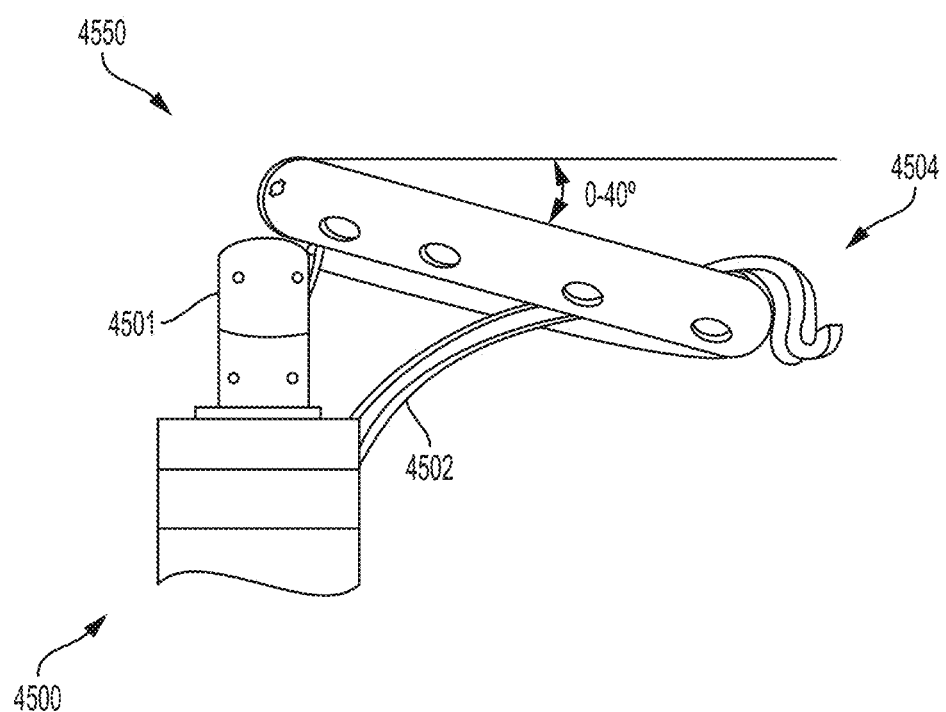
FIG. 45 depicts another illustrative view of a hinge system associated with the delivery system.
Figure 46:
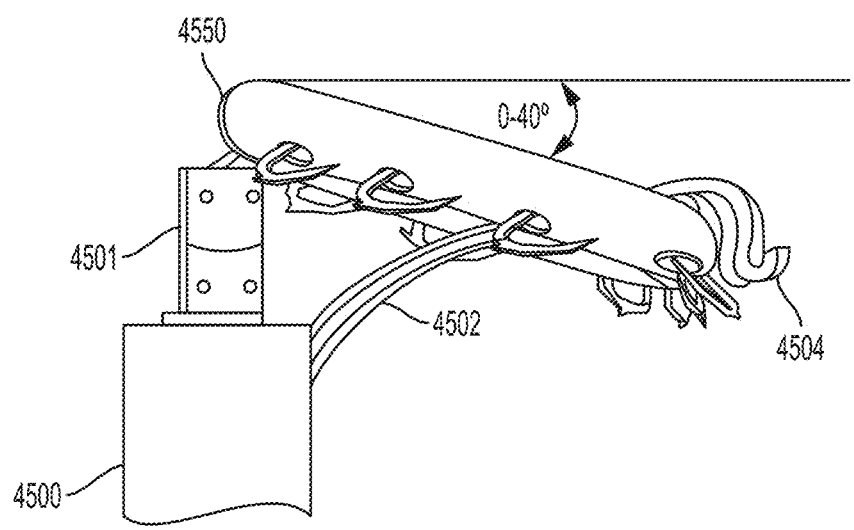
FIG. 46 depicts another illustrative view of a delivery system that is connected to a deployed ring while being manipulated by a stabilizing tool and before anchors are deployed.

In another embodiment, as shown in FIG. 45, the position of the tricuspid ring may be parallel to or below the plane of the tricuspid valve after rotation around the hinge. Again this approach is trans-apical, thus pulling the ring to the tissue. However, FIG. 45 differs from the embodiment of FIGS. 43-44, in that the ring orientation in relation to the delivery system may be in a range of about 0 degrees to about 40 degrees "below" the horizontal plane. In an additional embodiment, as shown in FIG. 45, the position of the tricuspid ring after rotation around the hinge may be parallel or slightly below to the plane of the tricuspid valve. The ring orientation, in this embodiment, in relation to the delivery system may be in a range of about 0 degrees to about 40 degrees "below" the horizontal plane. FIG. 46 depicts an embodiment with the anchors deployed.

As shown in FIGS. 45-46, in some embodiments, the delivery system 4500 may interface with a tricuspid ring 4550 that may have an anterior zone where anchors (not shown) exit the ring at an angle to provide anchoring forces in both the radial and axial direction. The tricuspid ring 4550 may also have a posterior zone where anchors exit the tricuspid ring at an angle to provide anchoring forces in both the radial and axial direction, a snapping mechanism (e.g., closure mechanism) (not shown), and a suture pin to provide a rotation pin for the sutures (not shown). The delivery system 4500 may include a distal end of the guiding catheter 4501, a stabilizing mechanism to ensure ring stabilization during an implantation procedure 4502, a delivery system (DS) tongue (e.g., ring interface device) (not shown), and a stabilizing tool 4504.

Figure 47:
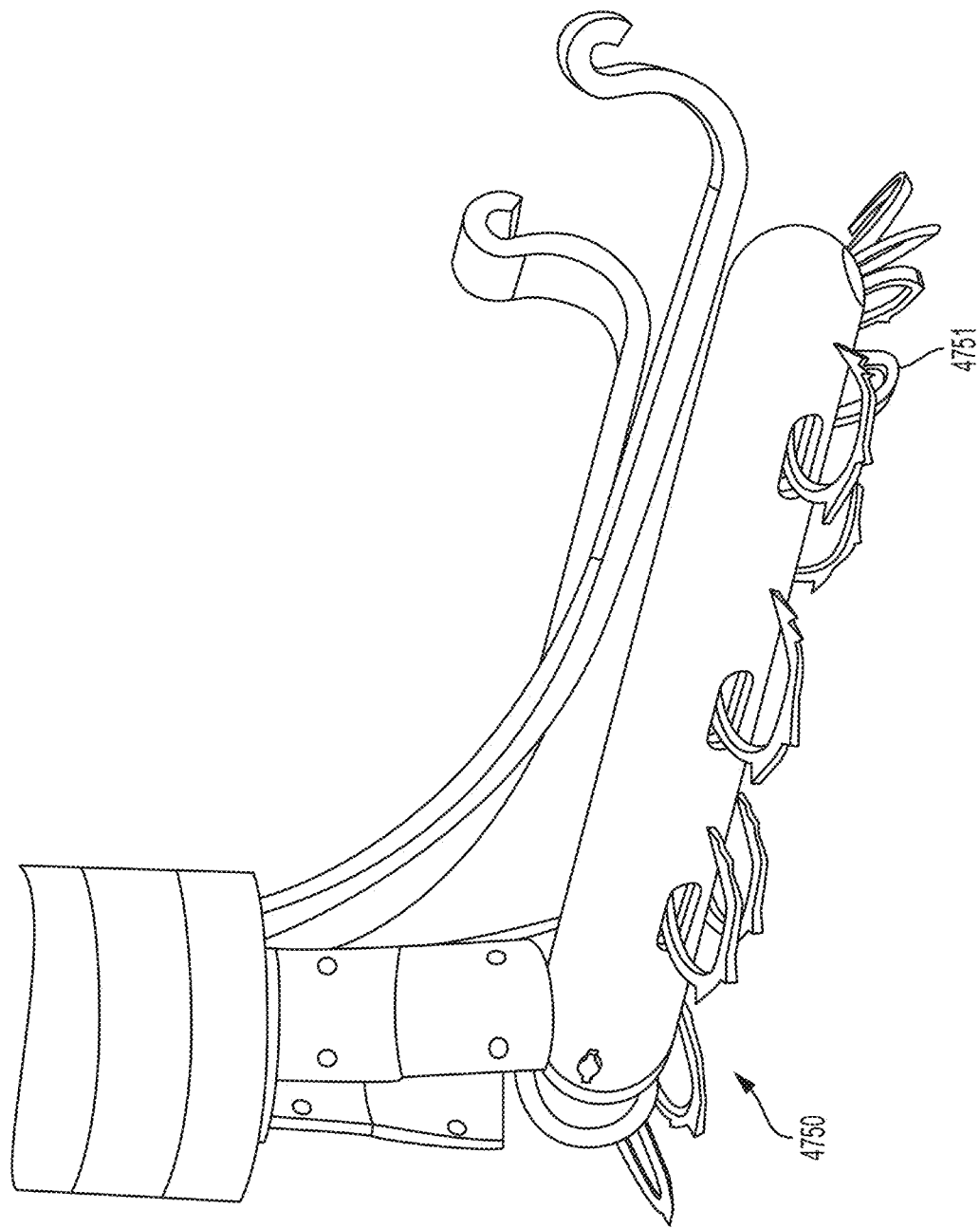
FIG. 47 depicts another illustrative view of a hinge system associated with the delivery system.

FIG. 47 shows a zoomed-in view of the tricuspid ring 4750 after rotation around the hinge whereby the plane of the ring may be parallel to the plane of the tricuspid valve. The approach may be trans-atrial, trans-septal, and/or trans-jugular, thus pulling the ring to the tissue. In an embodiment, as shown in FIG. 47, the ring orientation in relation to the delivery system may be in a range of about 0 degrees to about 40 degrees "below" the horizontal plane, and the anchors 4751 may or may not be deployed.

Figure 48:
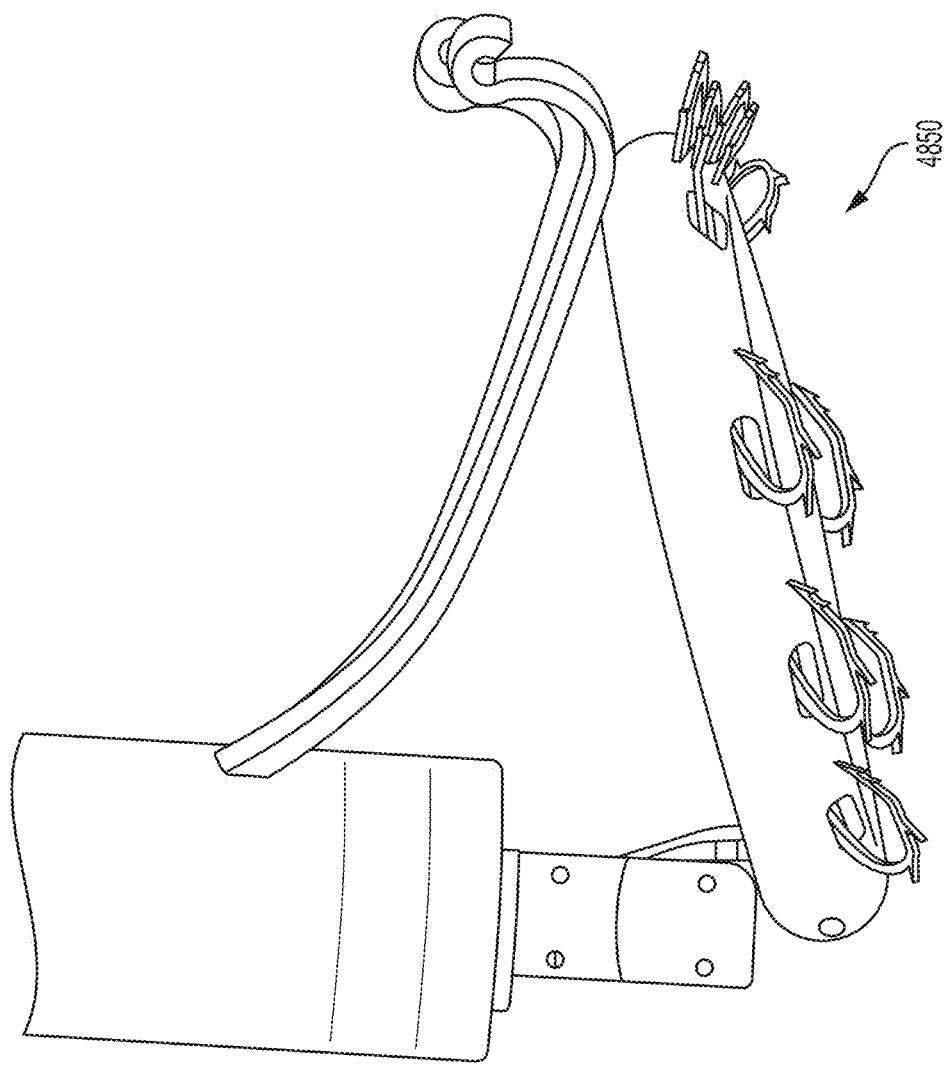
FIG. 48 depicts another illustrative view of a hinge system associated with the delivery system.

Additionally or alternatively, FIG. 48 shows a zoomed in view of the tricuspid ring 4850 after rotation around the hinge whereby the plane of the ring is parallel to the plane of the tricuspid valve. The approach of FIG. 48 may also be trans-atrial, trans-septal, and/or trans-jugular, thus pulling the ring to the tissue. In another embodiment, as shown in FIG. 48, the ring orientation in relation to the delivery system may be in a range of about 0 degrees to about 40 degrees "above" the horizontal plane, and the anchors may or may not be deployed.

Figure 49:
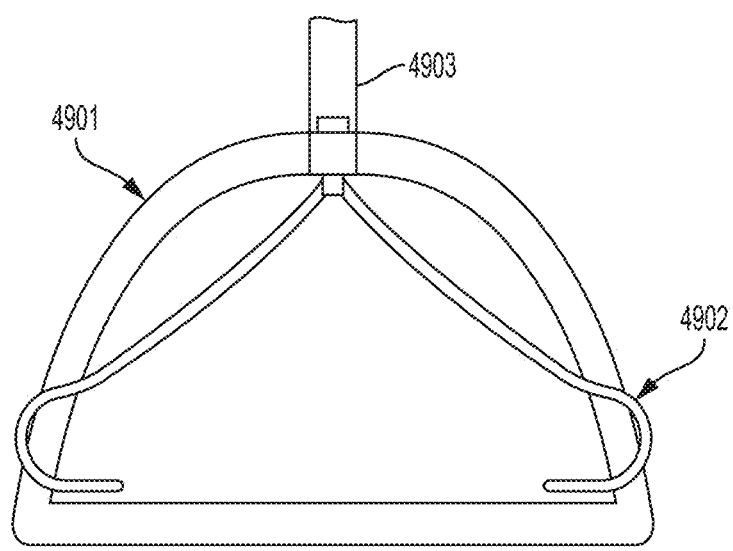
FIG. 49 depicts an illustrative view of a stabilizing tool and tricuspid ring.
Figure 50:
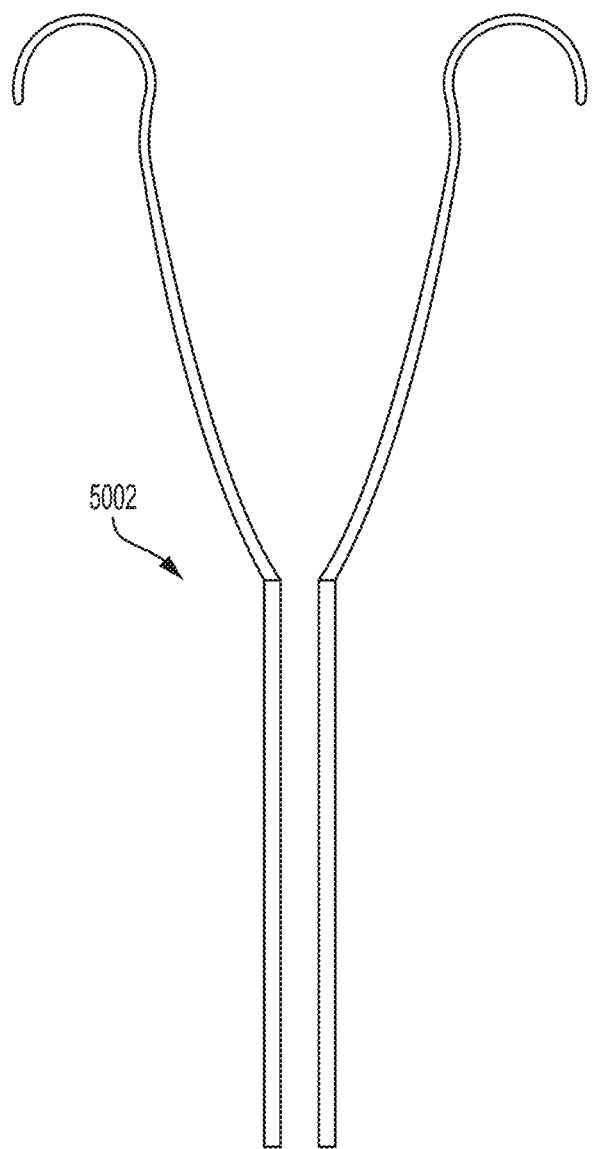
FIG. 50 depicts an isolated illustrative view of a stabilizing tool.

Referring now to FIGS. 49-50, an embodiment shows the geometry of the stabilizing tool that may be needed for the placement of the tricuspid ring 4901 above the annulus. By way of non-limiting example, FIG. 49 shows the tricuspid ring 4901, which may comprise various zones, and its interaction with the stabilizing tool 4902. In one embodiment, the stabilizing tool 4902 may be incorporated or attached to the delivery system 4903, as shown in FIG. 49. A more detailed view of the stabilizing tool is shown in FIG. 50. In some embodiments, the stabilizing tool 5002 may be made of super-elastic nickel titanium (Ni—Ti) from a laser cut hypotube.

Figure 51:
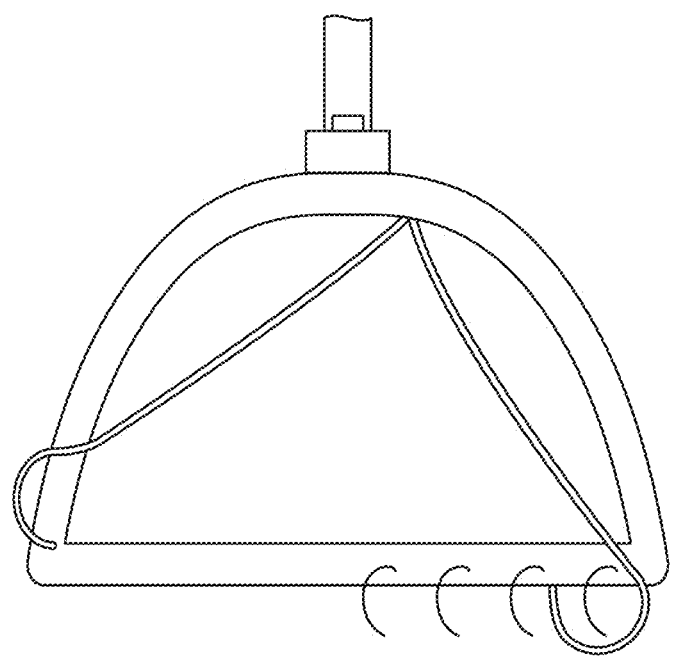
FIG. 51 depicts an illustrative view of deployed anchors at the septal zone.
Figure 52:
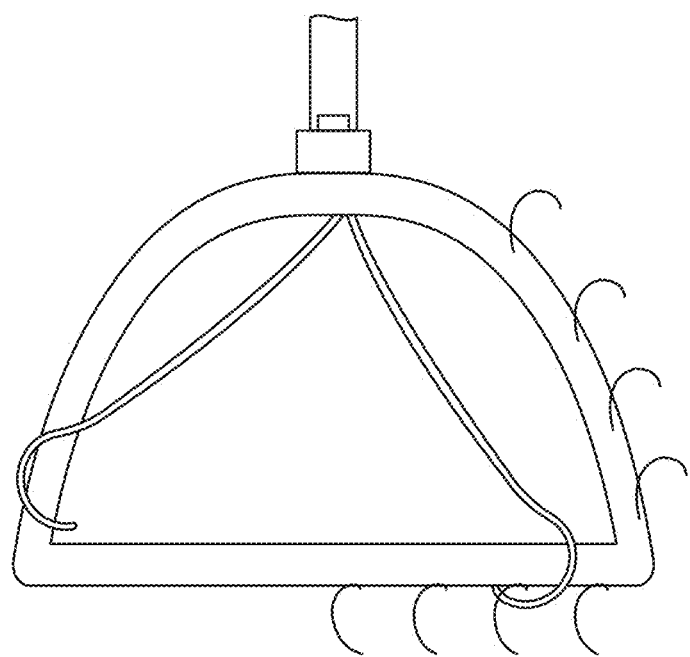
FIG. 52 depicts another illustrative view of deployed anchors at the septal and posterior zones.
Figure 53:
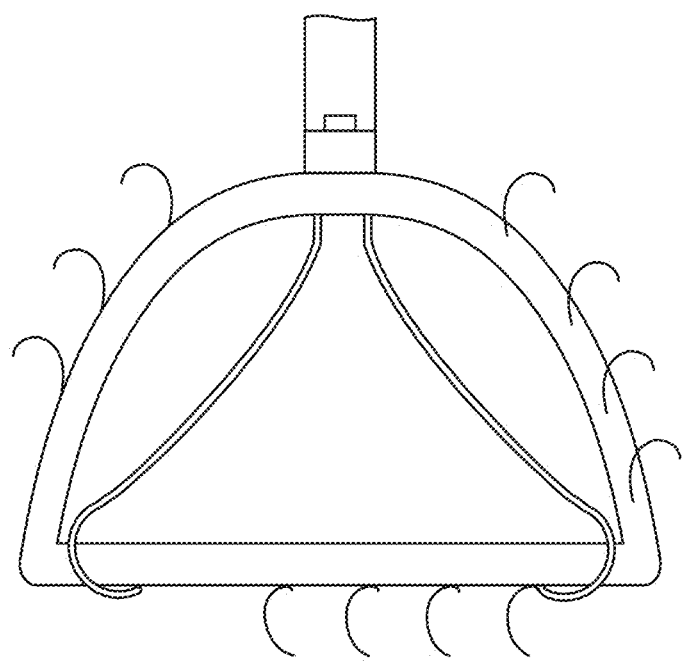
FIG. 53 depicts another illustrative view of deployed anchors at the septal zone, posterior zone, and first anterior zone.
Figure 54:
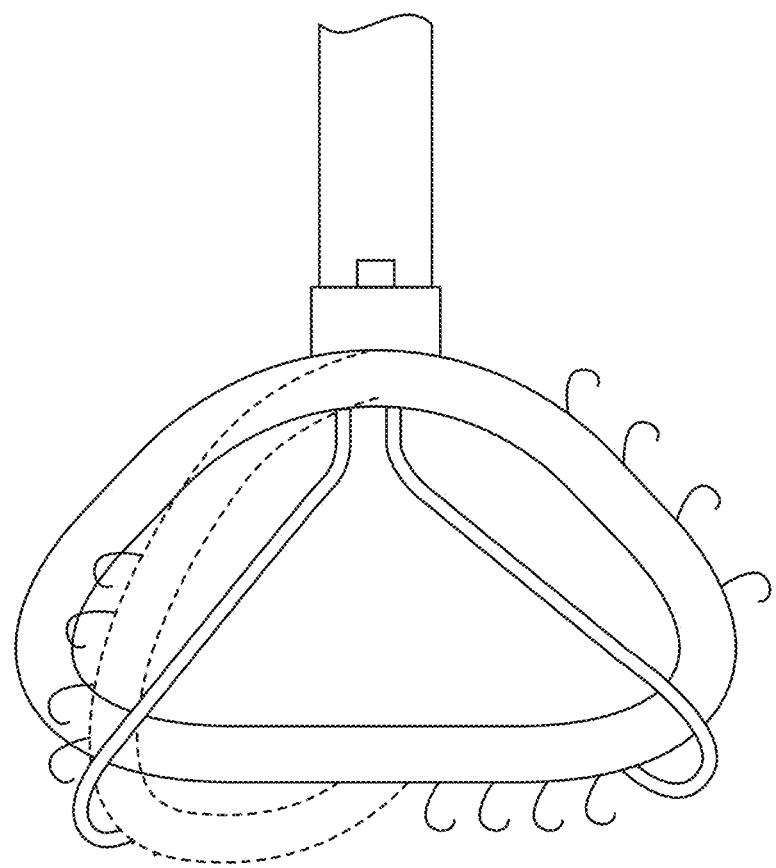
FIG. 54 depicts another illustrative view of a stabilizing tool and tricuspid ring with deployed anchors at all zones.

FIGS. 51-54 depict an illustrative ring as it is placed in the annulus, and the deployment of the anchors into the tricuspid annulus. In particular, FIG. 51 depicts the deployment of the septal anchors into the septal section of the tricuspid annulus adjacent to the septal leaflet. Additionally, FIG. 52 shows the deployment of the posterior anchors into the posterior section of the annulus adjacent to the posterior leaflet. FIG. 53 shows the additional deployment of the first zone of the anterior anchors that are adjacent to the anterior leaflet. FIG. 54 shows dragging of the anterior leaflet (e.g., by the stabilizing tool) as a means to reduce the dilation of the annulus and as a consequence, improve the coaptation of the anterior leaflet and the septal leaflet.

Figure 55:
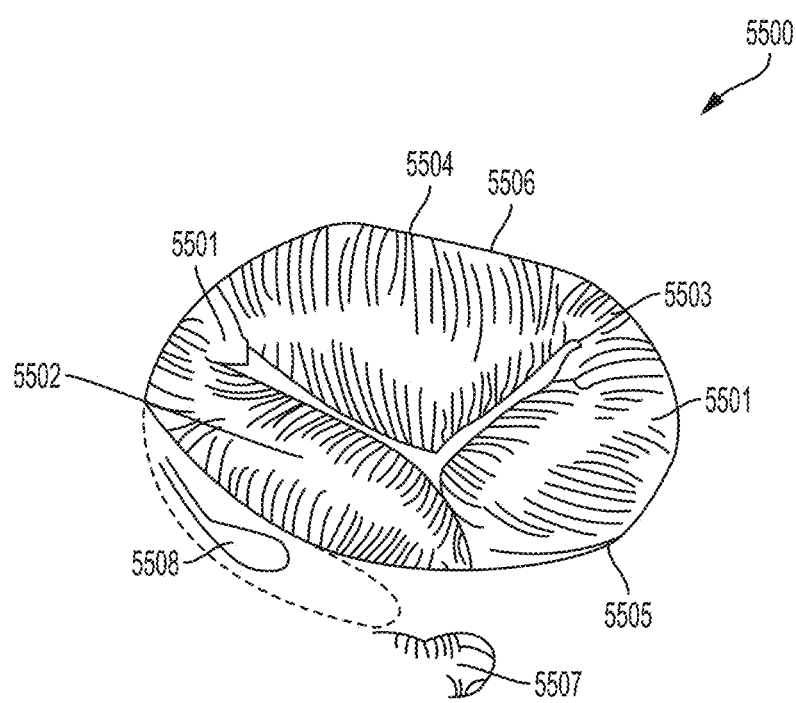
FIG. 55 depicts an illustrative view of a tricuspid valve.
Figure 56:
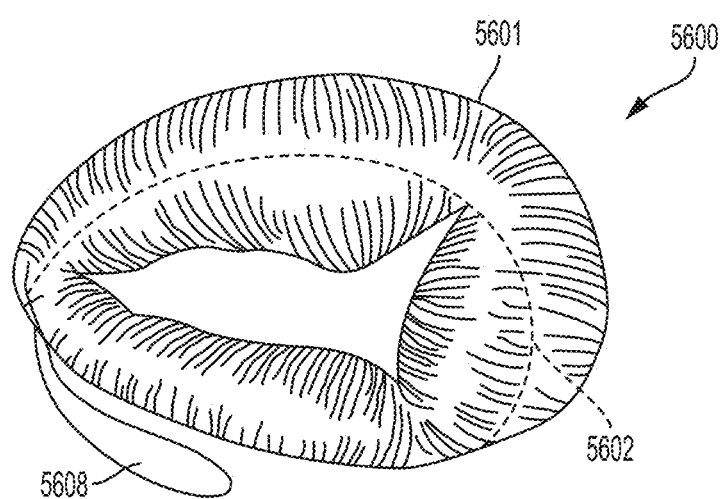
FIG. 56 depicts another illustrative view of a tricuspid valve.

FIGS. 55-56 shows further illustrative embodiments of a tricuspid valve 5500/5600. With reference to FIG. 55, it should be understood that a tricuspid valve 5500 may include: an anteroseptal commissure 5501, a septal leaflet 5502, an anteroposterior commissure 5503, an anterior leaflet 5504, a posteroseptal commissure 5505, an annulus 5506, a coronary sinus 5507, and an AV node 5508. As shown in FIG. 56, the annulus of tricuspid valve 5600 may be dilated. A dilated annulus shape 5601 is shown alongside a normal sized annulus (i.e., the desired shape of a tricuspid ring) 5602 (dashed lines) as a non-limiting example for clarity purposes. The tricuspid valve 5600 may also include an AV node 5608.

As would be understood by one skilled in the art, various methods for Mitral Valve Repair system are discussed herein. In some embodiments, a delivery system and an annuloplasty ring may be implanted in a minimally invasive manner into the human mitral annulus using trans-apical or trans-septal approaches. Moreover, described herein in detail are methods and tools for the delivery of a system with an annuloplasty ring having anchors introduced in a trans-apical manner to the mitral valve annulus.

As shown in various figures, (e.g., FIG. 39) in some embodiments, control over the position of the annuloplasty ring (e.g., the tilt angle and creation of intimate contact to tissue to facilitate the deployment of anchors) is capable due to various stabilizing mechanisms or tools (e.g. 3904). In some embodiments, the stabilizing tool may be made out of a tubular Ni—Ti structure. In some embodiments, the structure may have various prongs (e.g., as shown in FIG. 39, two prongs) that are designed to engage the annuloplasty ring, control its tilt, and control movement, thereby achieving anterior posterior reduction after the posterior portion of the annulus is anchored to the ring and before the anterior portion of the ring is anchored. In the various embodiments discussed above, the stabilizing tool may be a rigid element housed within one or more lumens of the delivery system.

Using the above disclosed system, once the ring is deployed (e.g., ejected from the delivery system) and has been placed in an operable geometry (e.g., a "D" shape), the stabilizing tool may be pushed through the at least one internal lumen of the delivery system and deployed adjacent and/or above the ring. The stabilizing tool may then engage the prongs (e.g., 2 prongs as shown in FIG. 39) with the ring using fluoroscopic guidance.

Although the stabilizing tool described above is effective and functional in a trans-apical approach, it can have limitations when the procedure needs to take place via a trans-septal approach. This limitation is due to the rigid nature of the stabilizing tool, both the portion housed permanently within the delivery system and the prongs. The rigid nature of the stabilizing tool limits its ability to impart a push-pull movement upon the annuloplasty ring during placement.

Figure 57:
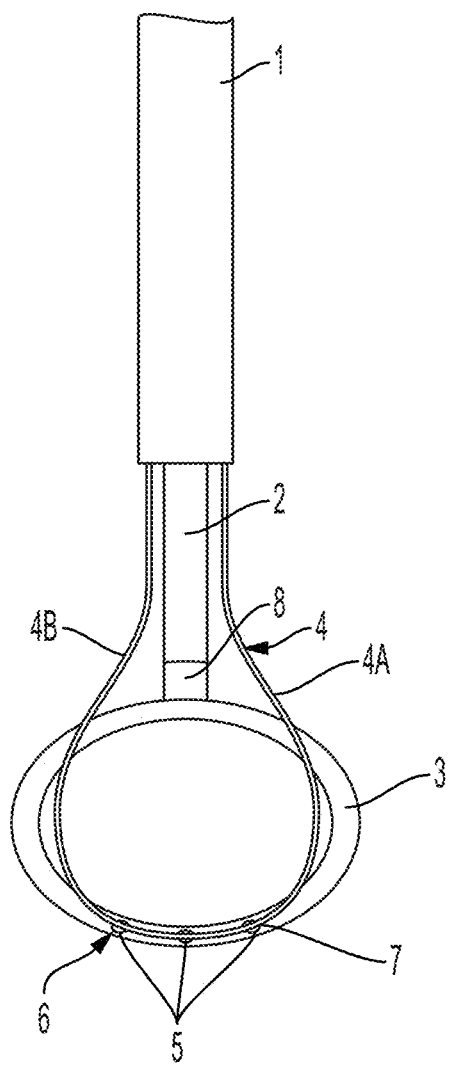
FIGS. 57-102 depict various illustrative views of a stabilizing tool.
Figure 58:
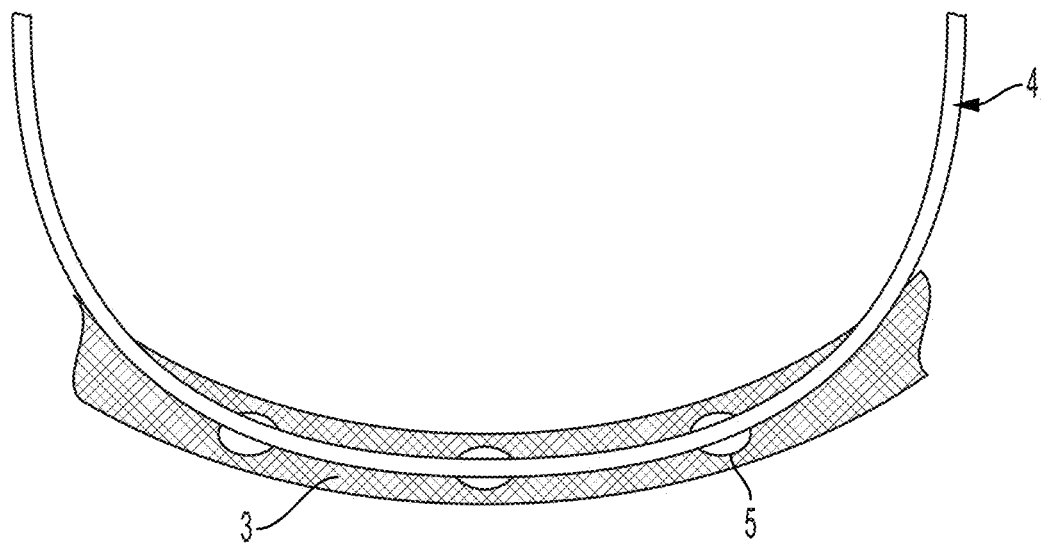
Figure 59:
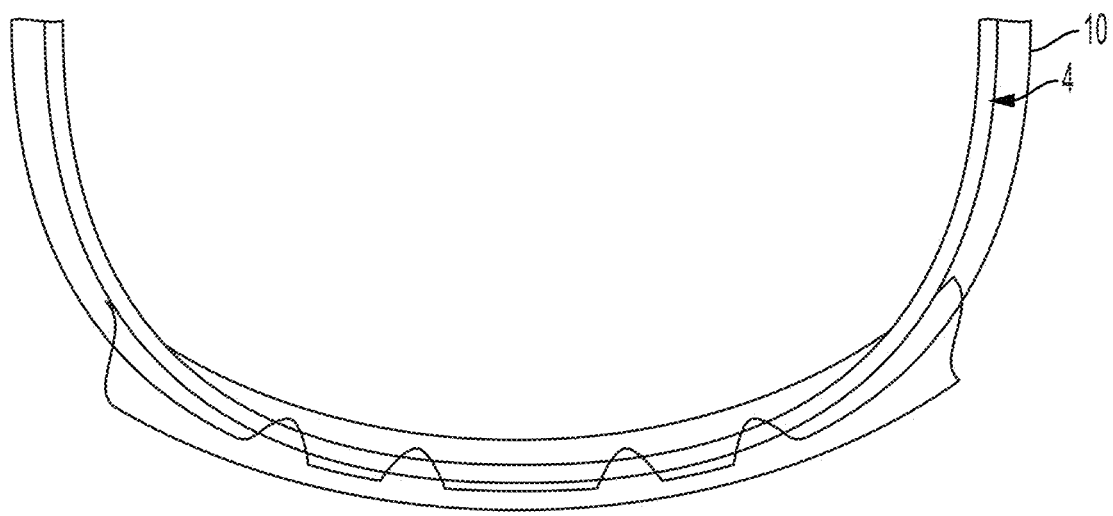

Thus, an alternative, more flexible, stabilizing mechanism, which is effective and functional in a trans-apical and trans-septal approach, is disclosed herein. Referring now to FIGS. 57-59, a perspective view of a distal portion of a mitral valve repair system is shown according to some embodiments. It should be noted that the figures are for illustrative purposes only, and that various other embodiments may exist and be described herein. Specifically, the system and methods described may also apply to tricuspid valve repair. As shown in FIG. 57, in some embodiments, the system may have an outer catheter 1, an inner catheter 2, an annuloplasty ring (e.g., after deployment and in "D" shape) 3, a stabilizing mechanism (i.e., adjusting tool) 4, connectors (e.g., suture connectors) 5, a surface (e.g., dracon surface) 6, one or more sutures 7, a hinged connection 8, one or more anchors 9, and one or more suture loops 10.

As shown in FIG. 57, the stabilizing mechanism 4 of some embodiments may include a Ninitol (Ni—Ti) wire having an outside diameter of between approximately 0.015 mm and approximately 0.030 mm. In a further embodiment, the stabilizing mechanism 4 may be of a length of approximately 4 meters, or any length to allow for proper manipulation of the annuloplasty ring as disclosed herein. In other embodiments, the stabilizing mechanism 4 may be heat treated to create a shape, which may have the ability to force transmission to the annuloplasty ring 3 at one or more desired locations.

It should be understood, that the stabilizing mechanism (e.g., the wire) 4 may have various and/or changing diameters along its length. For example, in some embodiments, the stabilizing mechanism 4 may have a larger diameter within the catheter (e.g., the straight section of catheter) 1 or 2 to allow the stabilizing mechanism to withstand a greater push-pull force to facilitate transmission. In additional embodiments, the stabilizing mechanism 4 may have a smaller or gradually decreasing diameter within the curves (e.g., the proximal section of the stabilizing mechanism) of the inner 2 or outer 1 catheter in order to create less catheter stiffness in the curved region of the system. Additionally, other diameters may be used in various portions of the stabilizing mechanism 4 (e.g., a section that exits the tip of the catheter and interacts with the annuloplasty ring). Accordingly, in some embodiments, the various diameters allow for the stabilizing mechanism 4 to provide optimal push-pull force transmission to the annuloplasty ring without prolapsing.

In further embodiments, the stabilizing mechanism 4 may be drawn or ground (e.g., have an oval or rectangular cross section) to provide greater push-pull force transmission to a desired section. One or more embodiments may also have a mid-section. The mid-section of the stabilizing mechanism 4 may be welded with two (2) connectors 5 that may then be stitched or inserted into the fabric of an annuloplasty ring 3, see for example, FIG. 58. This connection can create a strong yet removable connection between the stabilizing mechanism 4 and the annuloplasty ring.

In some embodiments, the stabilizing tool 4 may have two distinct portions. As shown in FIG. 57, the stabilizing mechanism 4 may have a first portion 4A and a second portion 4B that may be housed in the inner catheter 2. In a further embodiment, the inner catheter 2 may have two separate dedicated lumens (not shown), wherein the first portion 4A and second portion 4B may each be housed in a separate dedicated lumen. Accordingly, in various embodiments, the proximal end(s) of stabilizing mechanism 4 (e.g., 4A and 4B) may be emitted from the proximal end of the inner catheter 2 housed in the proximal handle.

In one or more embodiments, the stabilizing mechanism 4 may provide the ability to control for the angle of tilt of the annuloplasty ring 3 around the hinged connection 8. As shown, and in some embodiments, the hinged connection 8 may be located at the connection point between the annuloplasty ring 3 and the inner catheter 2. As discussed herein, the angle of tilt of the annuloplasty ring 3 may be adjusted by pushing and/or pulling the proximal end of the first portion 4A and/or the second portion 4B either simultaneously or separately.

Figure 60:
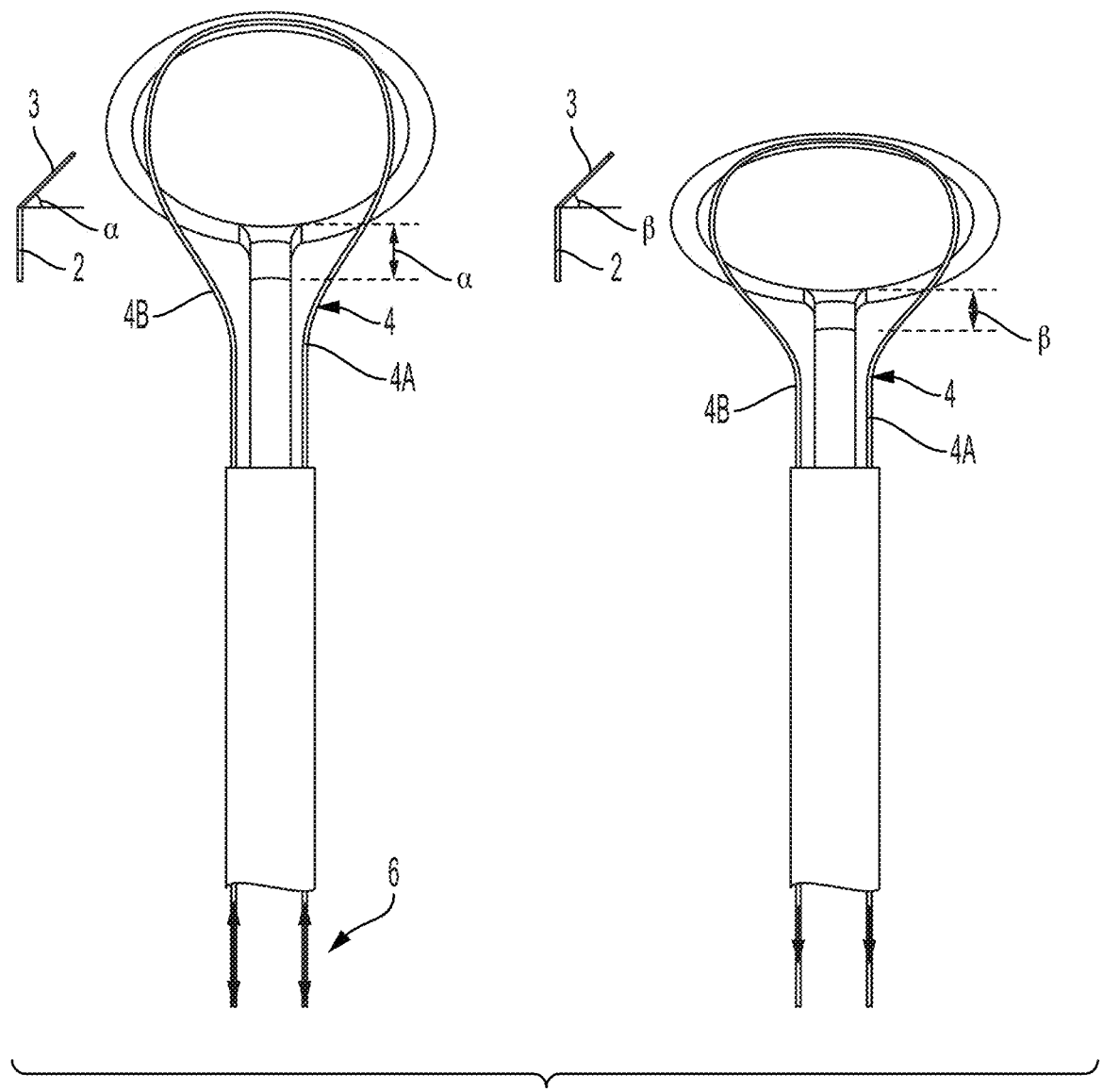

Referring now to FIG. 60, in some embodiments, the initial tilt angle of an annuloplasty ring 3, in reference to inner catheter 2, may be a. In a further embodiment, if there is a need to tilt the anterior section of the ring in a uniform manner (i.e., in order to decrease angle α to a smaller angle β), then an operator may pull both the first portion 4A and the second portion 4B simultaneously (e.g., using an additional mechanism to smoothly pull and/or push) within the proximal handle.

As should be understood, when an operator simultaneously pulls the first portion 4A and the second portion 4B it will cause a biasing force to be applied to one or more connector points 5, such as shown in FIGS. 57 and 58, consequently causing the rotation of the annuloplasty ring 3 around the hinged connection 8. The rotation of the annuloplasty ring 3 around the hinged connection 8, results in decreasing the ring tilt angle from a to (3, as illustrated in FIG. 60.

In an additional embodiment, (i.e., wherein a non-uniform tilt of the annuloplasty ring 3 is necessary), the first portion 4A may be fixed and the second portion 4B may be biased in one or more directions, thus resulting in a tilt of the annuloplasty ring in a single direction (e.g., toward the second portion 4B). In an alternative embodiment, (i.e., wherein a non-uniform tilt of the annuloplasty ring 3 is necessary), the second portion 4B may be fixed and the first portion 4A may be biased in one or more directions, thus resulting in a tilt of the annuloplasty ring in a single direction (e.g., toward the first portion 4A).

Figure 61:
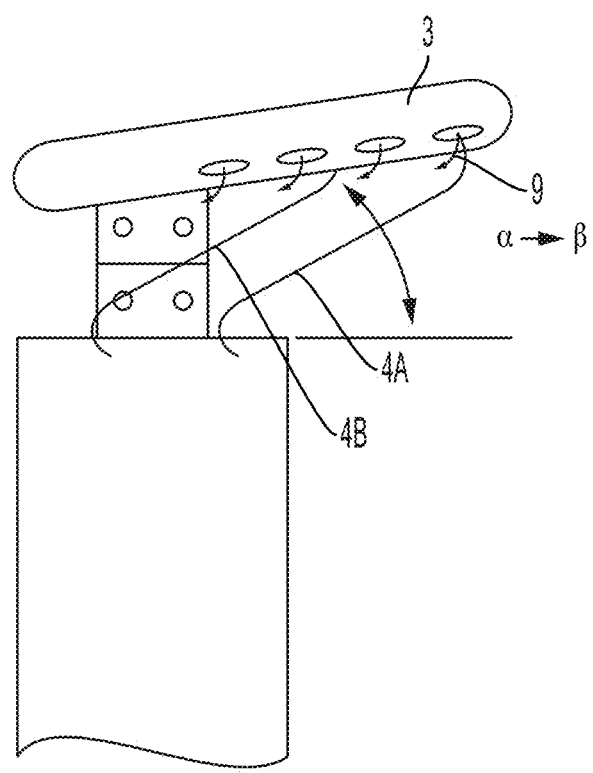

In some embodiments, during a mitral valve repair procedure, the deployment of the stabilizing mechanism 4 may be conducted before or after deployment of the anchors 9, shown in FIG. 61, in the posterior section of the ring.

Accordingly, in some embodiments, the annuloplasty ring 3 may be deployed out of the outer catheter 1 in an elongated geometry. In a further embodiment, a "D" shaped geometry may then be achieved via manipulation of the annuloplasty ring 3 using one or more steering mechanisms (not shown) in thw outer catheter 1 and/or the inner catheter 2, as described herein. Thus, in one or more embodiments, using the techniques described herein, intimate contact and desired placement of the annuloplasty ring 3, and thus the one or more anchors 9 (e.g., in the posterior side of the annuloplasty ring) may be achieved to allow for proper deployment of the anchors.

Once the posterior side of the annuloplasty ring 3 is properly anchored, further manipulation of the annuloplasty ring 3 may be accomplished. For example, it may be desired to drag or move the anterior side of the annuloplasty ring 3 to the anterior side of annulus. Accordingly, in some embodiments, control of the tilt angle for annuloplasty ring 3 may be achieved via the stabilizing mechanism 4 as shown in FIG. 61. It should be understood, that this is a non-limiting example, and that the annuloplasty ring 3 may be properly anchored on the anterior side, and movement may be required related to the posterior side of the annuloplasty ring.

In a further embodiment, the stabilizing mechanism 4 may not only control the tilt angle of the annuloplasty ring 3, but may also control the intimate contact between the annuloplasty ring 3 and the annulus. For example, once an optimal tilt angle of the annuloplasty ring 3 has been achieved, initial contact with the anterior portion of the annulus may be established, and verified by echocardiogram. Once verified, the stabilizing mechanism 4 may remain engaged in order to stabilize the intimate contact between the annuloplasty ring 3 and the annulus during the deployment of anchors 9 in the anterior portion of the annuloplasty ring.

After successful deployment of the one or more anterior anchors 9 and completing the anchoring process, the stabilizing mechanism 4 may be released from the annuloplasty ring 3. In one embodiment, removal of the stabilizing mechanism 4 may be accomplished by applying a biasing force (e.g., pulling) on one end of the stabilizing mechanism (e.g., the first portion 4A or the second portion 4B). This is possible because, in some embodiments, the stabilizing mechanism 4 may be threaded through a Dacron covering (e.g., a Dracon covering the outer portion of the annuloplasty ring 3, such as that shown in FIG. 58). In another embodiment, the stabilizing mechanism 4 may be released from the Dacron fabric by applying a biasing force (e.g., pulling) on the stabilizing mechanism to remove it from the suture loops 10 attached to the Dacron cover, such as that shown in FIG. 59. Once the stabilizing mechanism 4 is fully removed from the suture loops 10, it can be retracted through the tip of the inner catheter 2 and drawn from the proximal handle.

Figure 62:
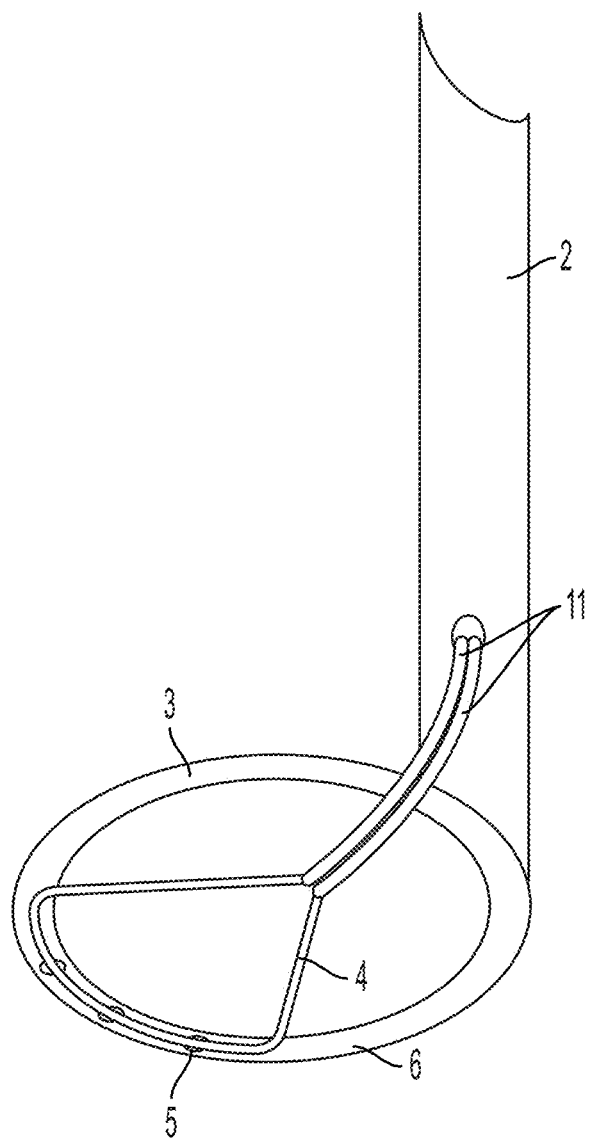

Referring now to FIG. 62, an embodiment is shown having an annuloplasty ring 3 connected to inner catheter 2. According to some embodiments, one or more hypotubes 11 may exit from the inner catheter 2. As shown in the illustrative example of FIG. 62, two hypotubes 11 may exit the inner catheter 2. In some embodiments, the hypotubes 11 may run in/through (e.g., be housed inside) separate lumens (not shown) within the inner catheter 2. In a further embodiment, and as shown in FIG. 62, the one or more hypotubes 11 may house the stabilizing mechanism 4 (e.g., first 4A and second 4B portions). In some embodiments, the hypotubes 11 may be constructed of Ni-TI, stainless steel, a polymeric (e.g., reinforced polyamide), etc. In additional embodiments, the inside diameter may range from about 0.020 inches to about 0.038 inches and may have an ID which may range from about 0.012 inches to about 0.022 inches.

Figure 63:
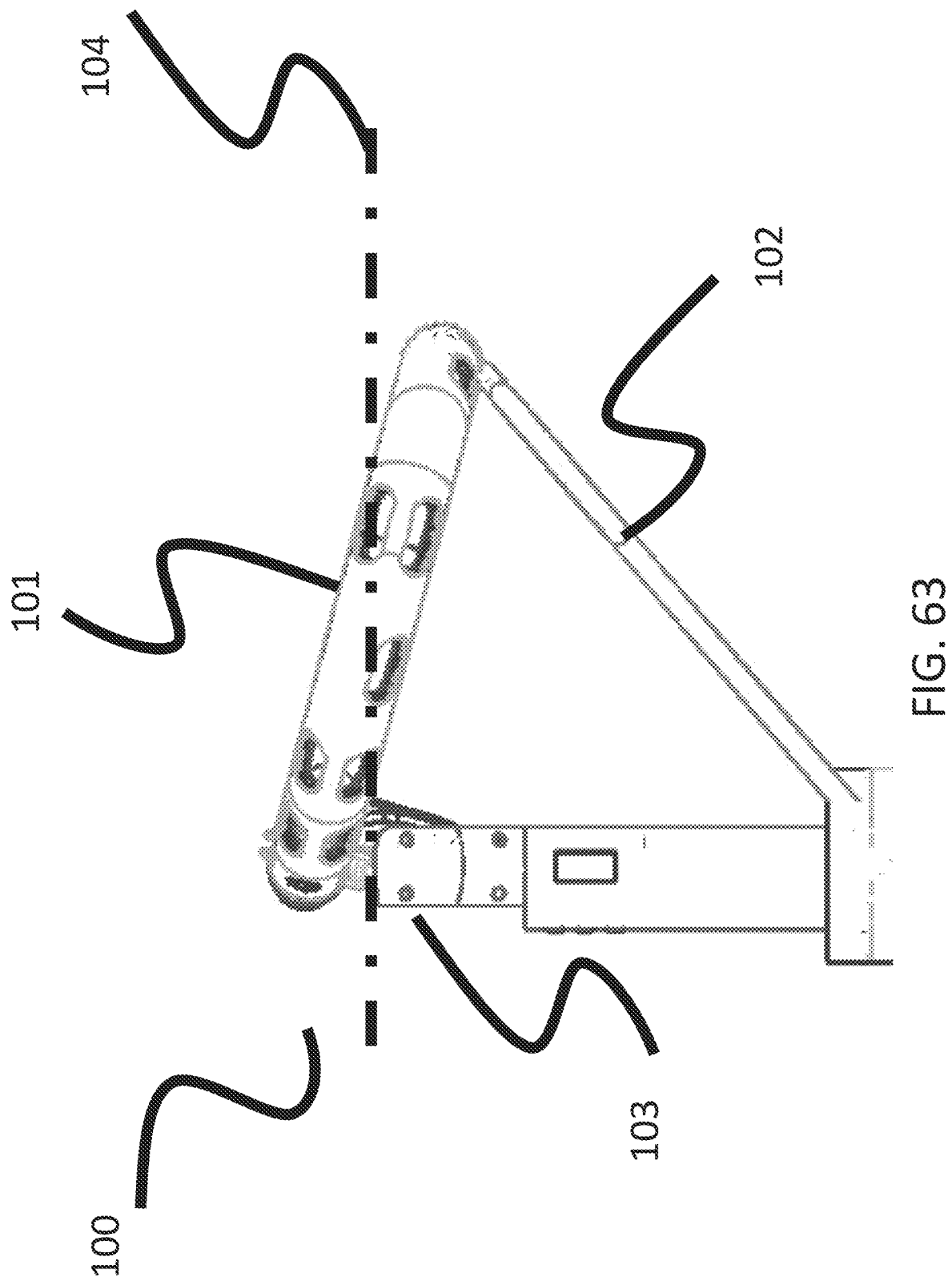
Figure 64:
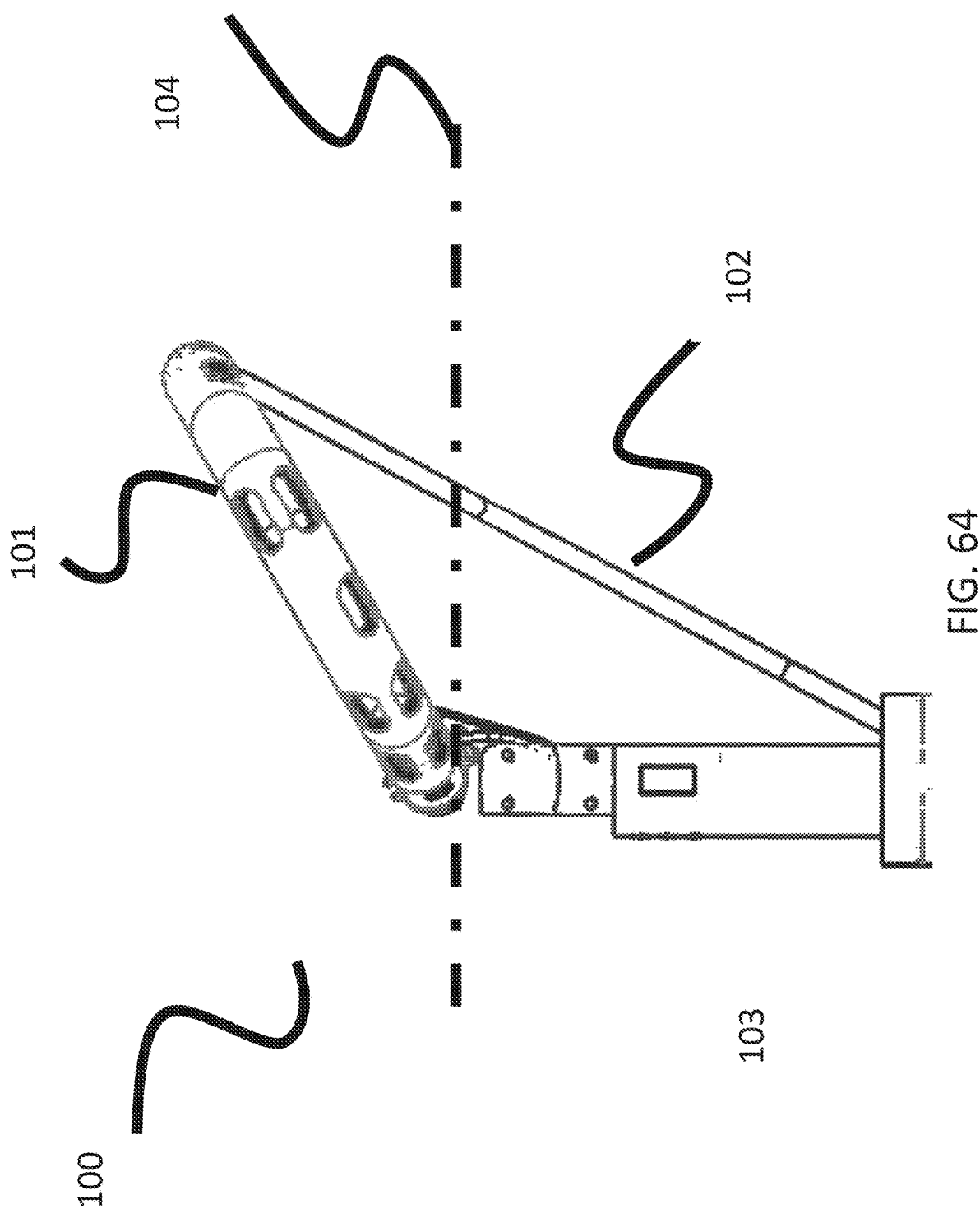

Referring now to FIGS. 63 and 64, a distal section of a trans-apical system 100 is shown according to one or more embodiments. The system 100 may have an annuloplasty ring 101, a stabilizing mechanism (i.e., adjusting tool) 102, and a delivery system interface (e.g., a hinged connection) 103. FIGS. 63 and 64 also provides a guideline 104 for indicating a level orientation of the annuloplasty ring 101. As shown, FIG. 63 illustrates an embodiment wherein a negative angle exists between the annuloplasty ring 101 and the level guideline 104. Alternatively, FIG. 64 illustrates an embodiment wherein a positive angle exists between the annuloplasty ring 101 and the level guideline 104. Thus, as should be understood from FIGS. 63 and 64, the stabilizing mechanism 102 may control the angle of the annuloplasty ring 101 in relation to the annulus in a trans-apical approach to and from a negative angle (e.g., FIG. 63) and a positive angle (e.g., FIG. 64).

Figure 65:
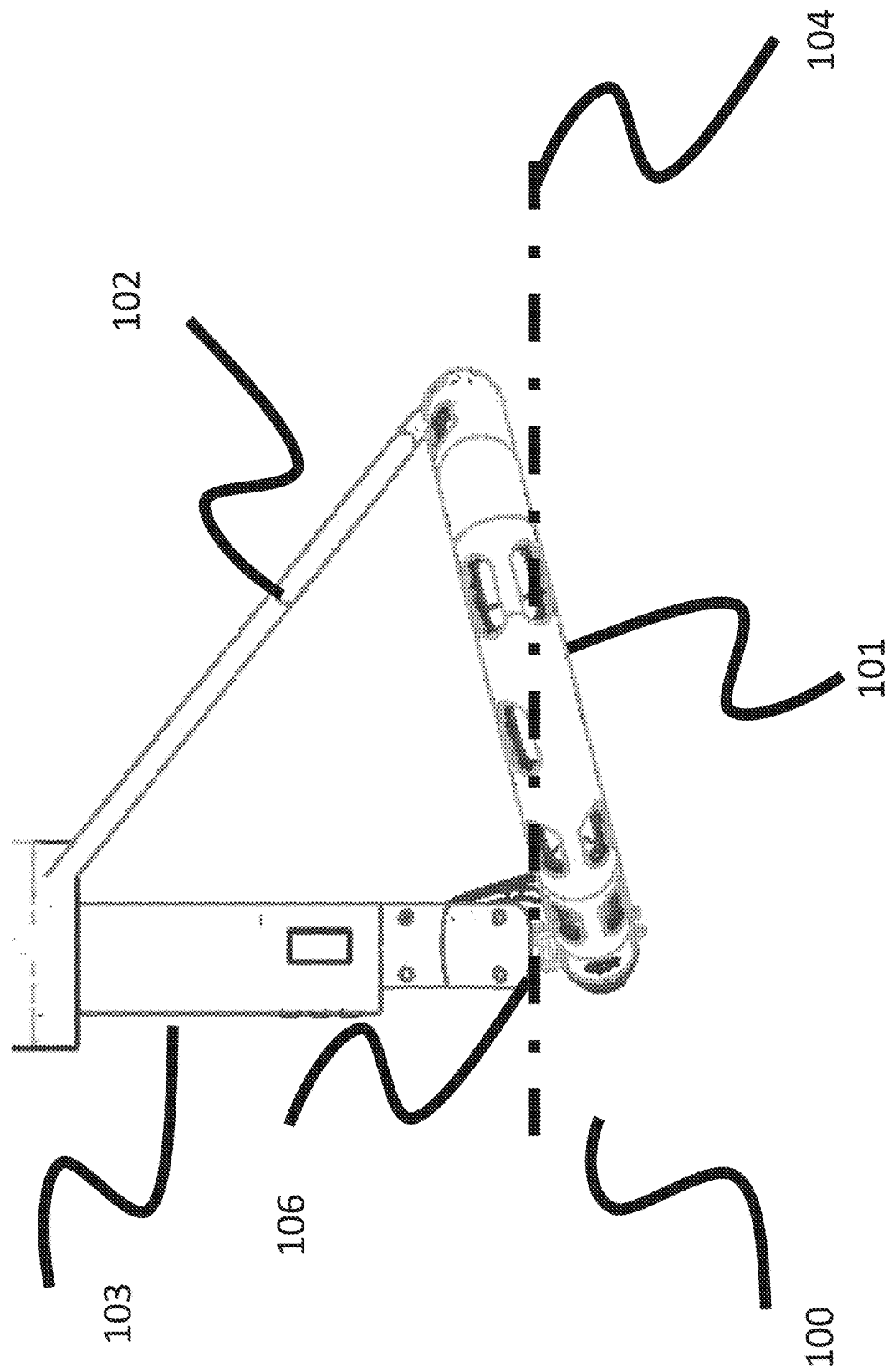
Figure 66:
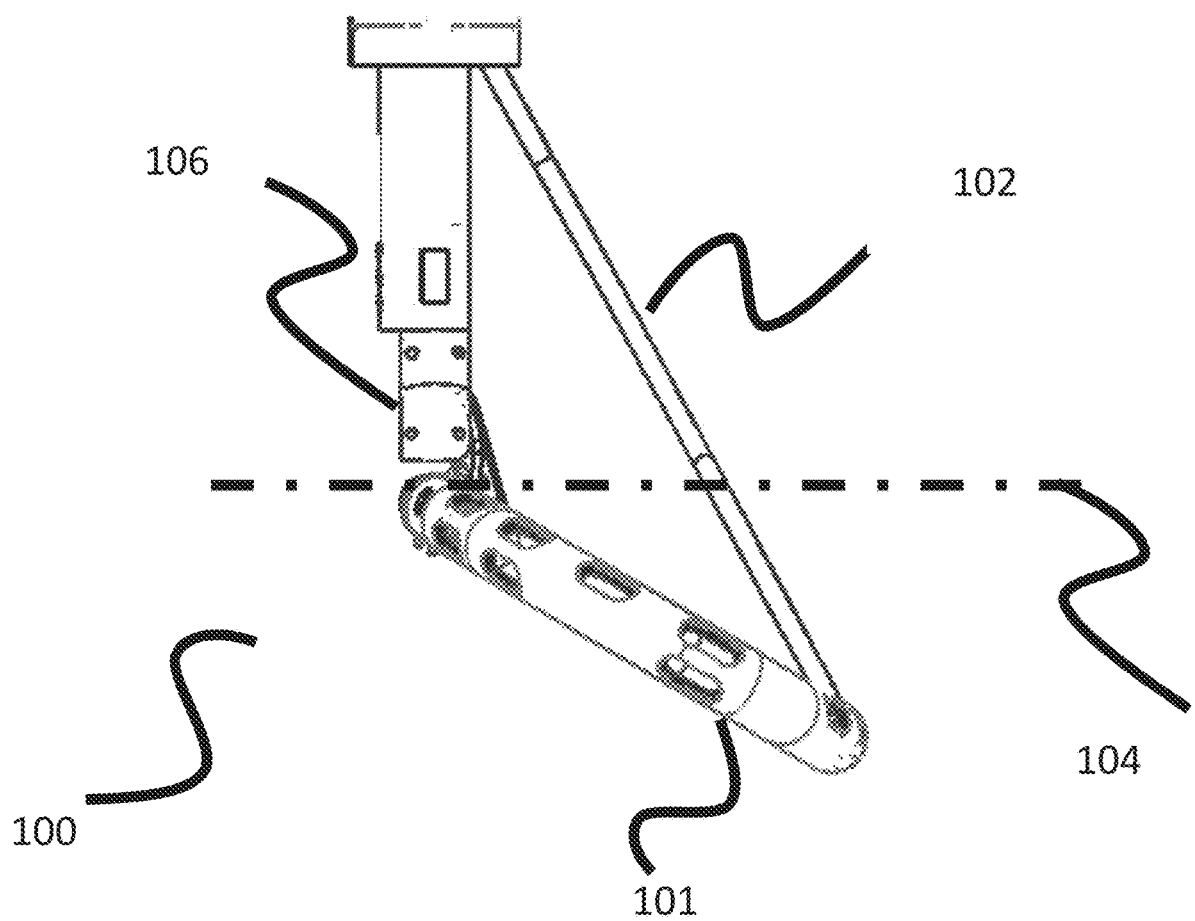

FIGS. 65 and 66 show an embodiment of the distal section of a trans-septal approach 100. Similar to the trans-apical approach, the annuloplasty ring 101 may be controlled via a stabilizing mechanism (i.e., adjusting tool) 102 in order to obtain a positive angle (e.g., FIG. 65) and/or a negative angle (e.g., FIG. 66).

Figure 67:
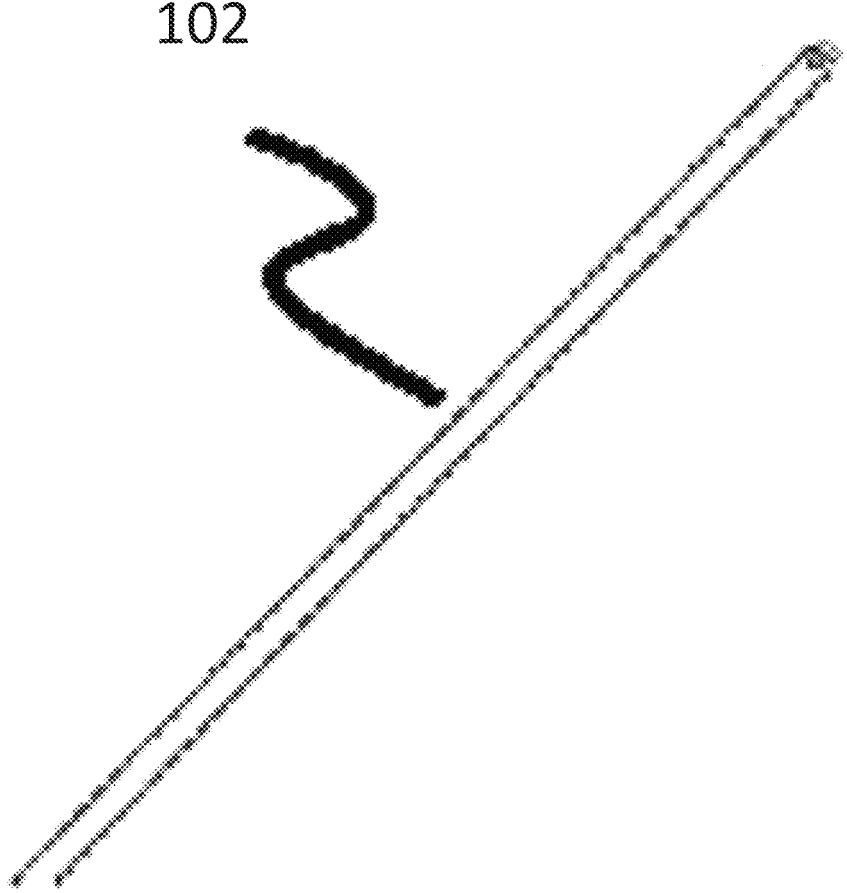

Turning to FIG. 67, an illustrative embodiment of the distal end of a stabilizing mechanism 102 is shown. In some embodiments, the stabilizing mechanism 102 may be machine cut, laser cut, and/or heat treated to any shape. As should be understood by one skilled in the art, this may include adding a hole on the distal end that may be used to form an attachment to the annuloplasty ring 101. In a further embodiment, the stabilizing mechanism 102 may be constructed from one or more pieces (e.g., 1, 2, 3, . . . n pieces of wire or cable as discussed herein). Accordingly, the stabilizing mechanism 102 may be constructed of any material or combination of materials in order to provide the required geometry and to attach at the distal end of the annuloplasty ring 101.

Figure 68:
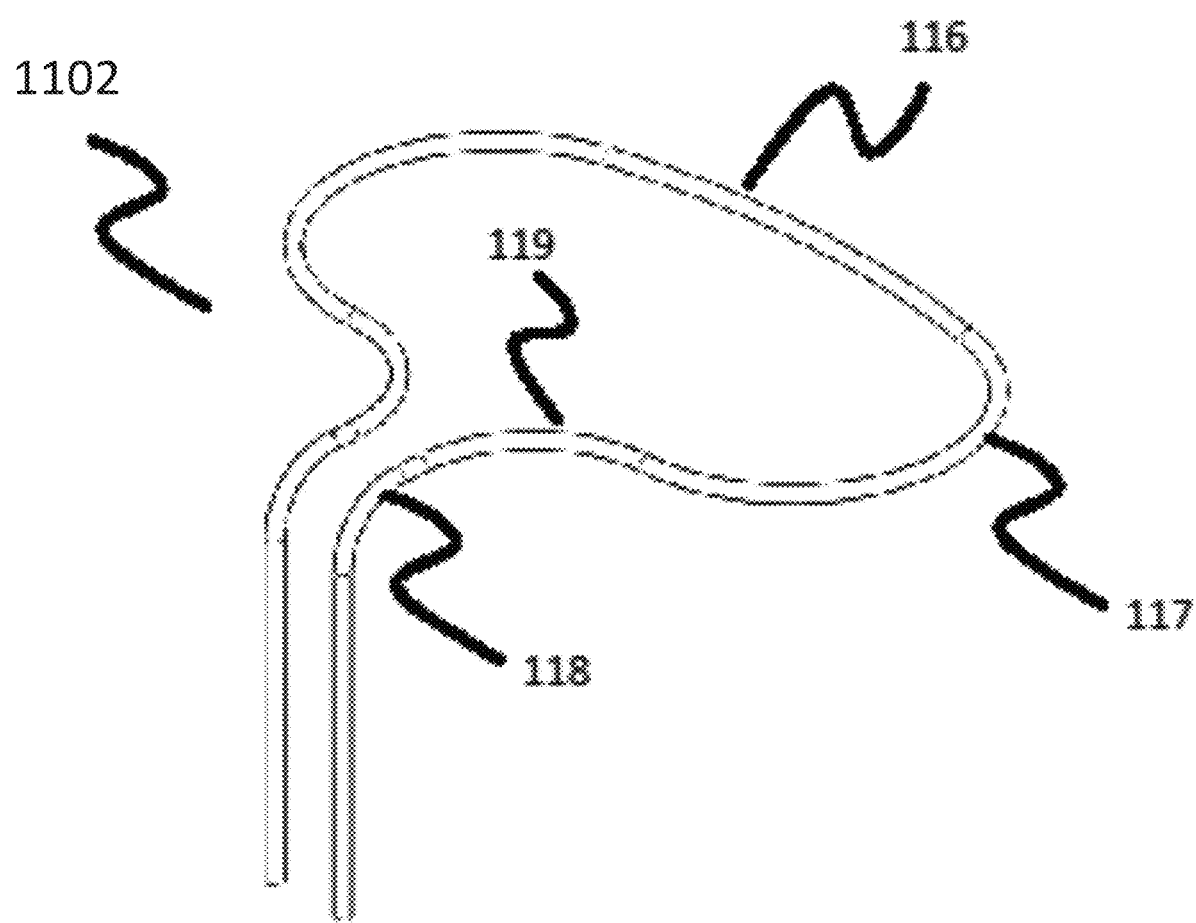

As shown in FIG. 68, in some embodiments, the stabilizing mechanism 102 may be constructed from a single wire shaped, with or without heat treating/setting, into a desired shape at the distal end. In a further embodiment, the wire is advanced through the catheter into the proximal side of the delivery system. In some embodiments, and as shown in FIG. 68, the stabilizing mechanism 102 may have an anterior portion 116 designed to support the anterior portion of the annuloplasty ring 101. In a further embodiment, the stabilizing mechanism 102 may comprise a bending radius area 117 in or near the commissure area, a bending radius area 118 in or near the annuloplasty ring 101 plane, and a bending radius area 119 in or near the posterior side of the annuloplasty ring.

As discussed herein, the stabilizing mechanism 102 may be constructed of various materials and be of various sizes, such as, for example, the wire shape may be constructed of stainless steel, steel, and/or a memory shape material (e.g., Nitinol) and may have a diameter from about 0.2 mm to about 2 mm. The stabilizing mechanism 102 may vary in size and diameter (e.g., be reduced to allow for greater flexibly and/or enlarged to increase rigidity and support).

Figure 69:
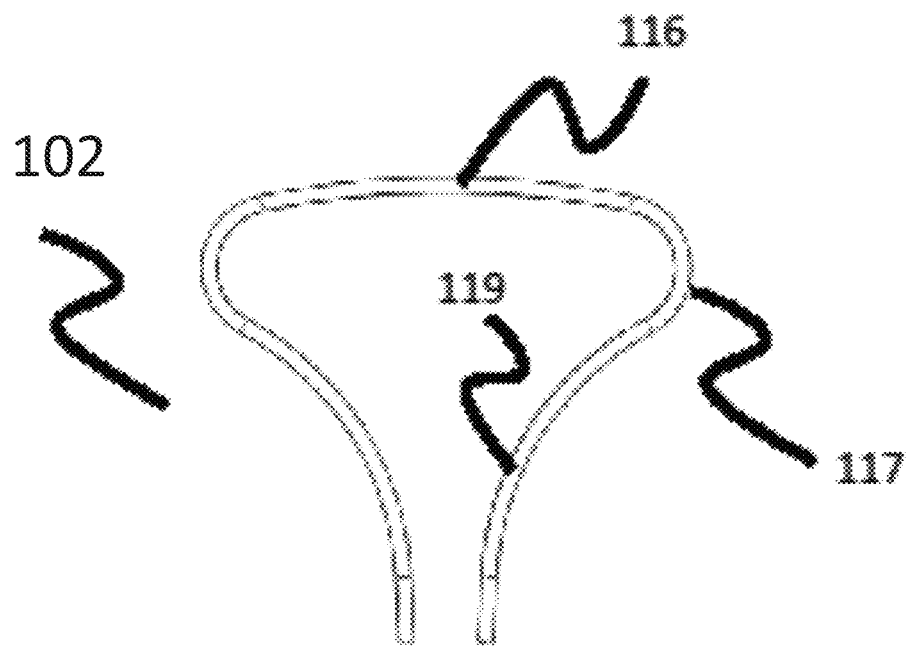
Figure 70:
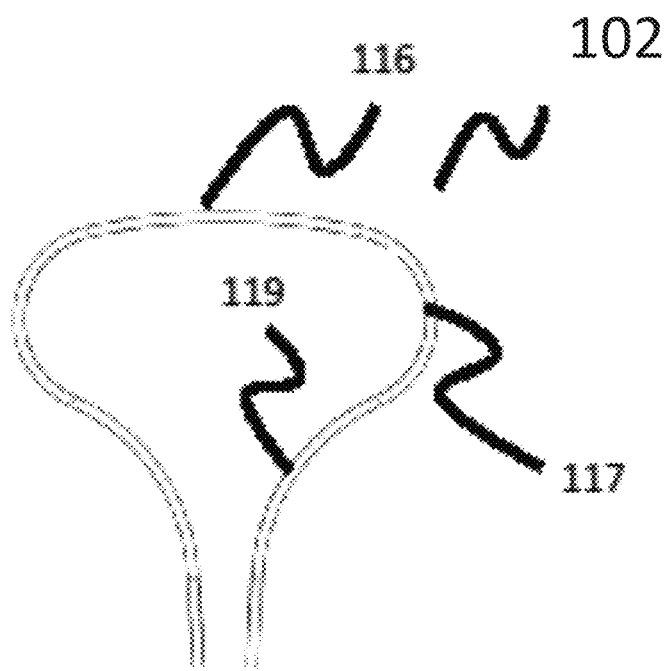
Figure 71:
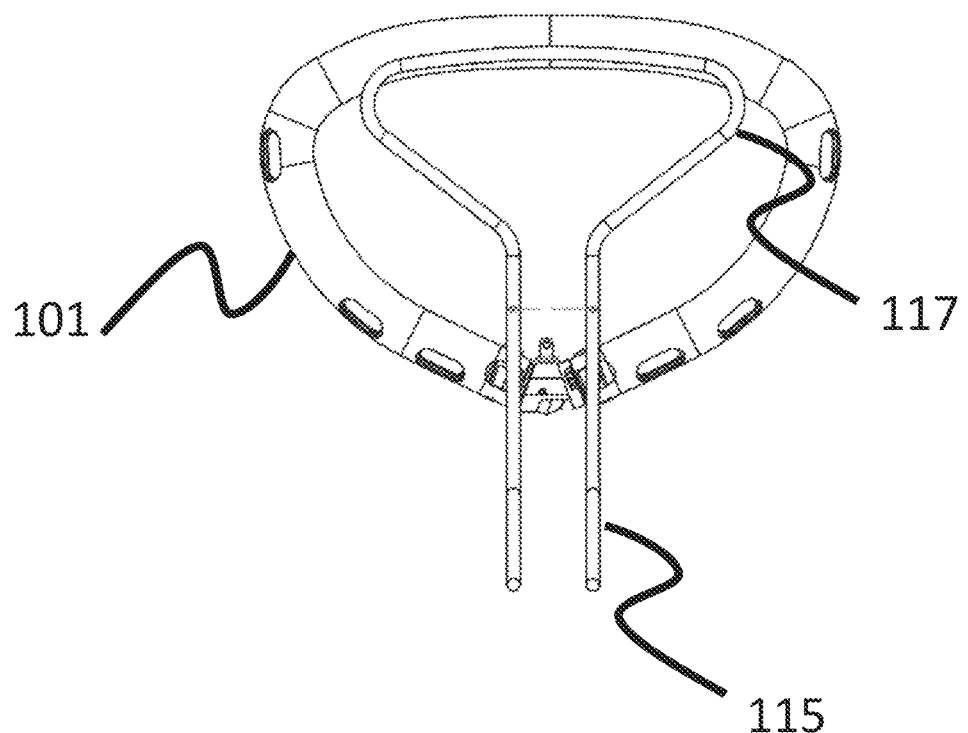
Figure 72:
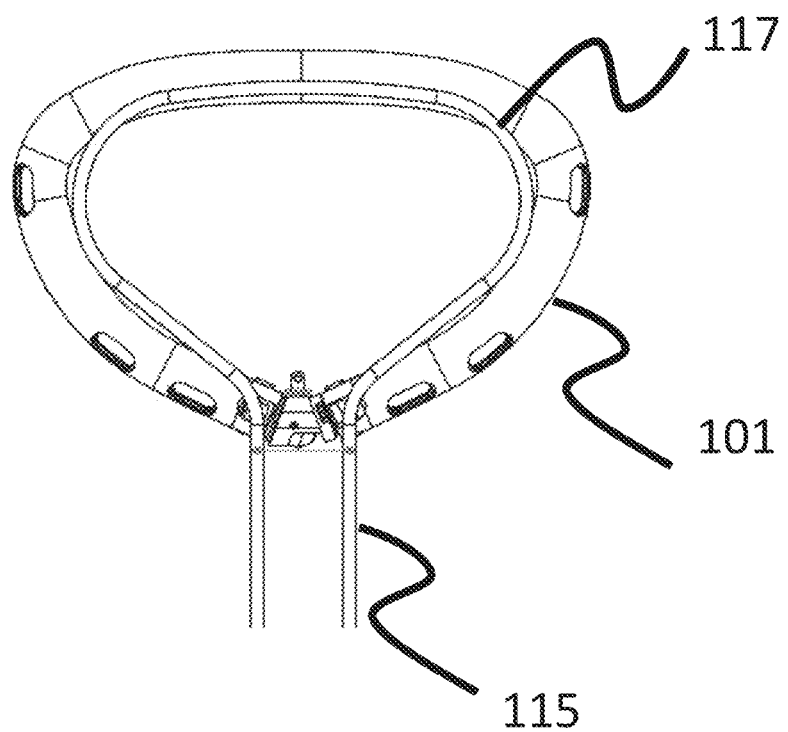

Referring now to FIGS. 69 and 70, illustrative embodiments are shown demonstrating different shapes that the stabilizing mechanism 102 can take on via manipulation of the anterior portion 116 and the two bending radiuses (e.g., 117 and 119). Additional illustrative embodiments are shown in FIGS. 71 and 72 in which the anterior portion 116 of the stabilizing mechanism 102 can influence the shape of the annuloplastly ring 101 via the bending radiuses 117 and 119. As shown, FIG. 72 illustrates an embodiment wherein the support is against the entire circumference of the annuloplastly ring 101. In contrast, FIG. 71 illustrates a potential alternative system wherein the stabilizing mechanism 102 only contacts the anterior portion of the annuloplastly ring.

Figure 73:
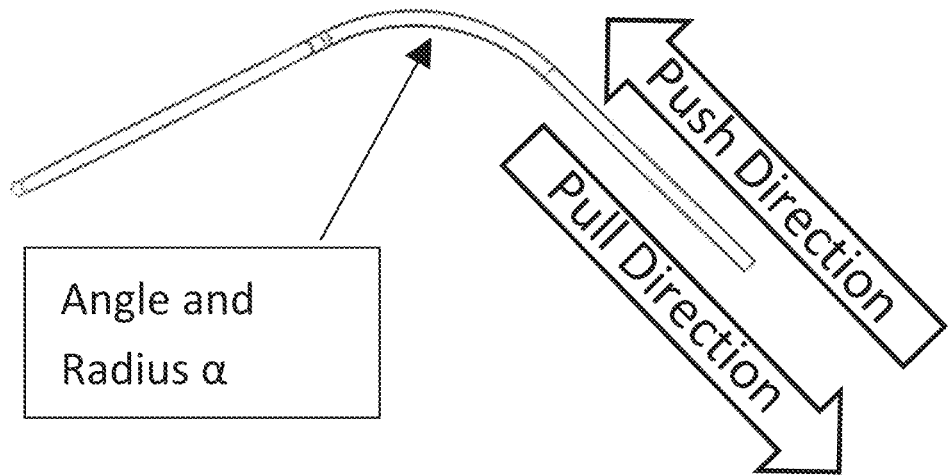
Figure 74:
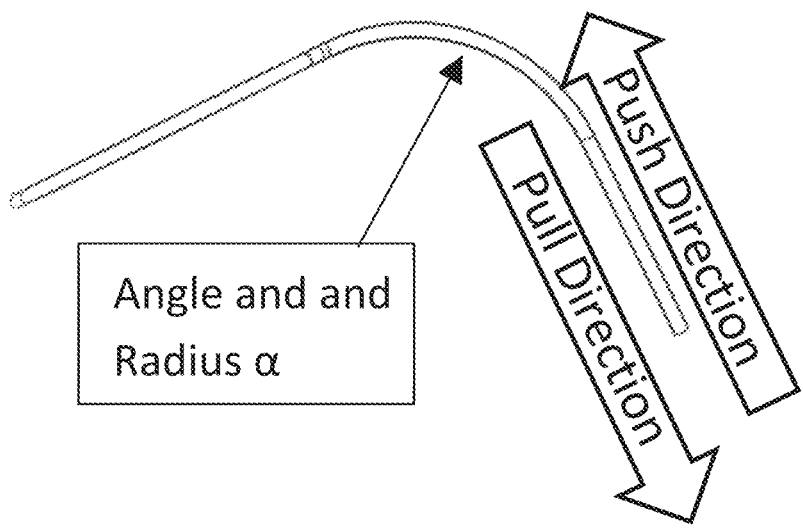

As shown in FIGS. 73 and 74, an alpha angle and radius may be modified. In some embodiments, the angle may range from about 45° to about 180°, and the radius may vary from about 2 mm to about 30 mm. In some embodiments, modifying the angle and radius may influence the push/pull ability as well as the elongation of the stabilizing mechanism 102.

Figure 75:
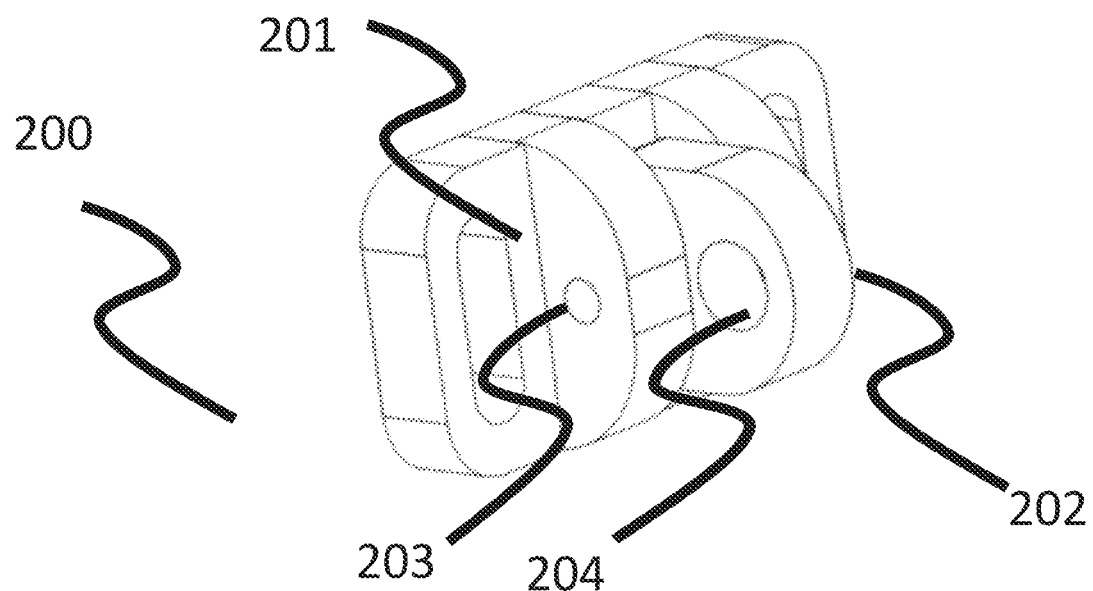
Figure 76:
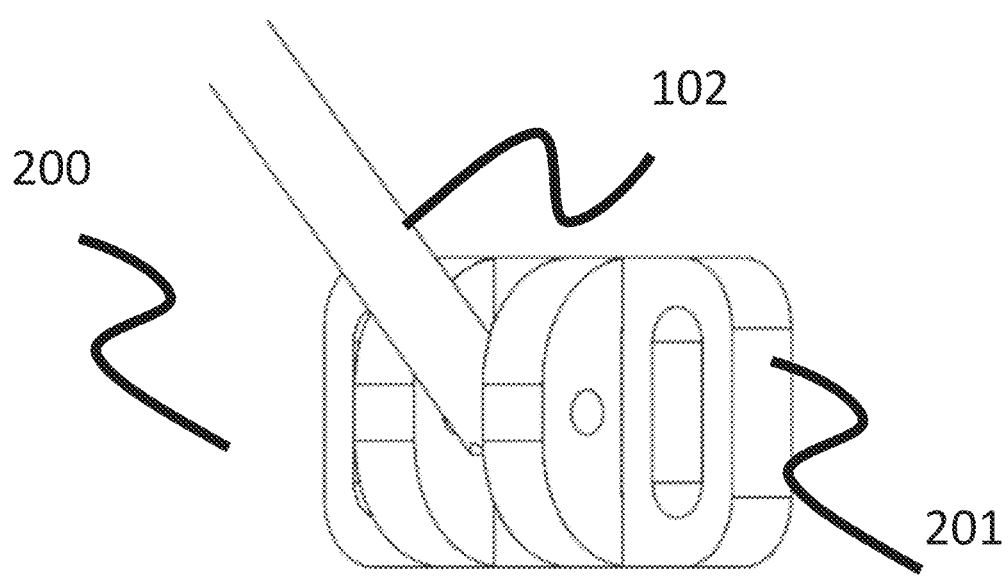

Referring to FIGS. 75-78, some embodiments, as illustrated, may comprise a stabilization mechanisms (e.g., a wire) 102, a pull attachment subassembly 200, a docking post 201, a docking post anchorage 202, a deactivation wire 210, an opening 203 for a deactivation wire, and an opening 204 in the docking post anchorage to attach the stabilization mechanism. As shown in FIGS. 75 and 76, an embodiment may comprise a docking post 202 for the stabilization mechanism 102.

Figure 77:
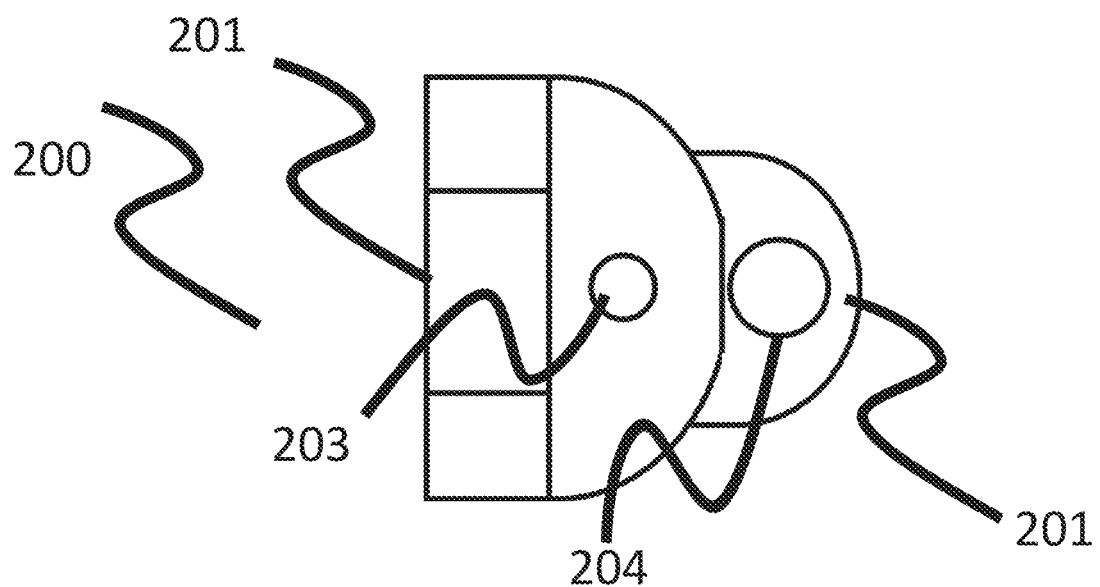
Figure 78:
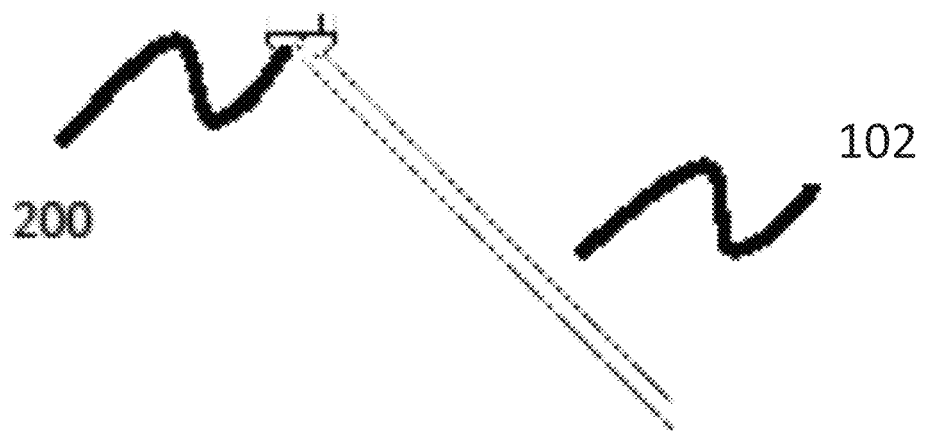

As shown in FIG. 75, the attachment feature 200 may be composed of two separate components: the docking post 201, which may be attached to an annuloplasty ring (not shown) using any of the various methods disclosed herein (e.g., suturing to the tubing itself and/or suturing to a fabric that covers the body of the ring); and the docking post anchorage 202, which may be comprised of metal or a plastic (e.g., polyethylene, polypropylene and PVC). In some embodiments, the docking post anchorage 202 may be attached to the stabilization mechanism 102 using various means (e.g., adhesive, welding, sutures, etc.). FIGS. 75 and 77 are illustrative embodiments of the attachment feature 200 without the stabilization mechanism 102 attached. Alternatively, FIGS. 76 and 78 are shown with the stabilization mechanism 102 attached to the attachment feature 200.

Separation of the stabilization mechanism 102 from the attachment feature 200 may occur in various ways. In some embodiments, an area may be prepared such that it breaks at a certain point responsive to a particular force level or a specific movement. In other embodiments, a separate component may function as a deactivation feature, such as, for example, a deactivation wire. In an even further embodiment, the separation may happen responsive to a suture being pulled (e.g., by a user) causing the release of the attachment. As shown in FIGS. 77 and 78, an attachment may be separated using the deactivation wire 210. Accordingly, in some embodiments, a hole 203 for the deactivation wire may be used to secure the stabilizing mechanism 102. It should be understood that the foregoing are merely exemplary and that other means of separation may exist.

Figure 79:
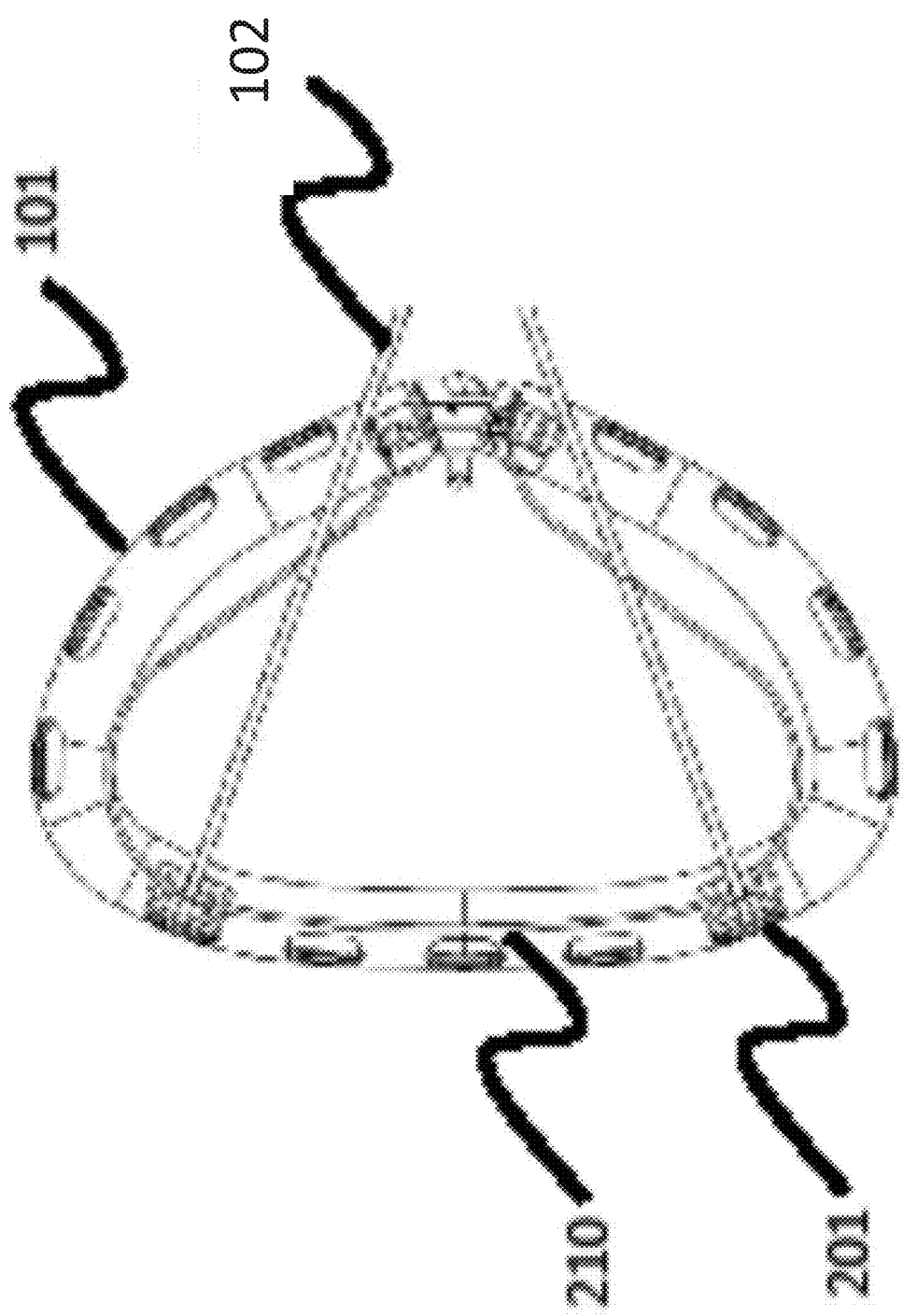
Figure 80:
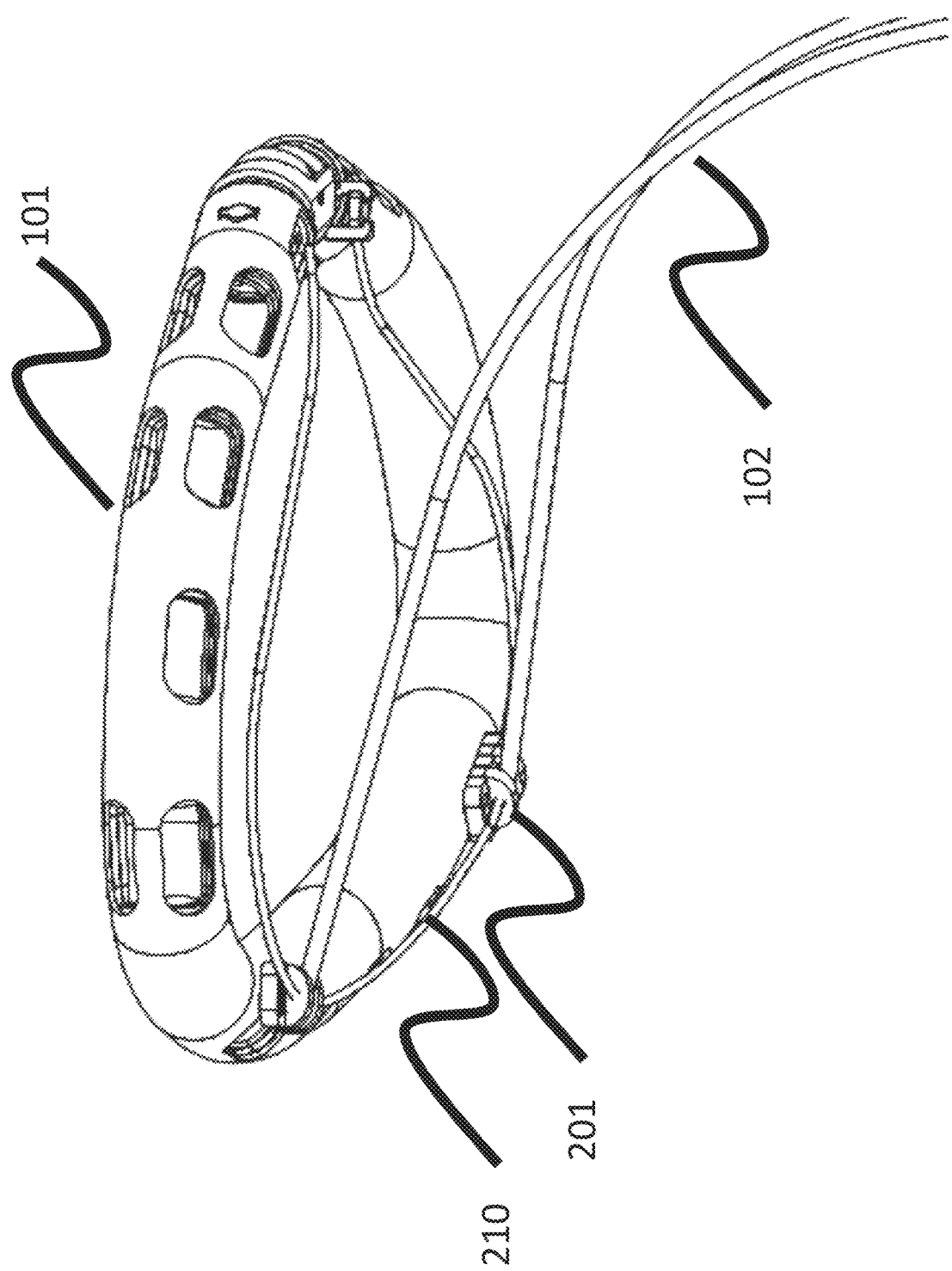
Figure 81:
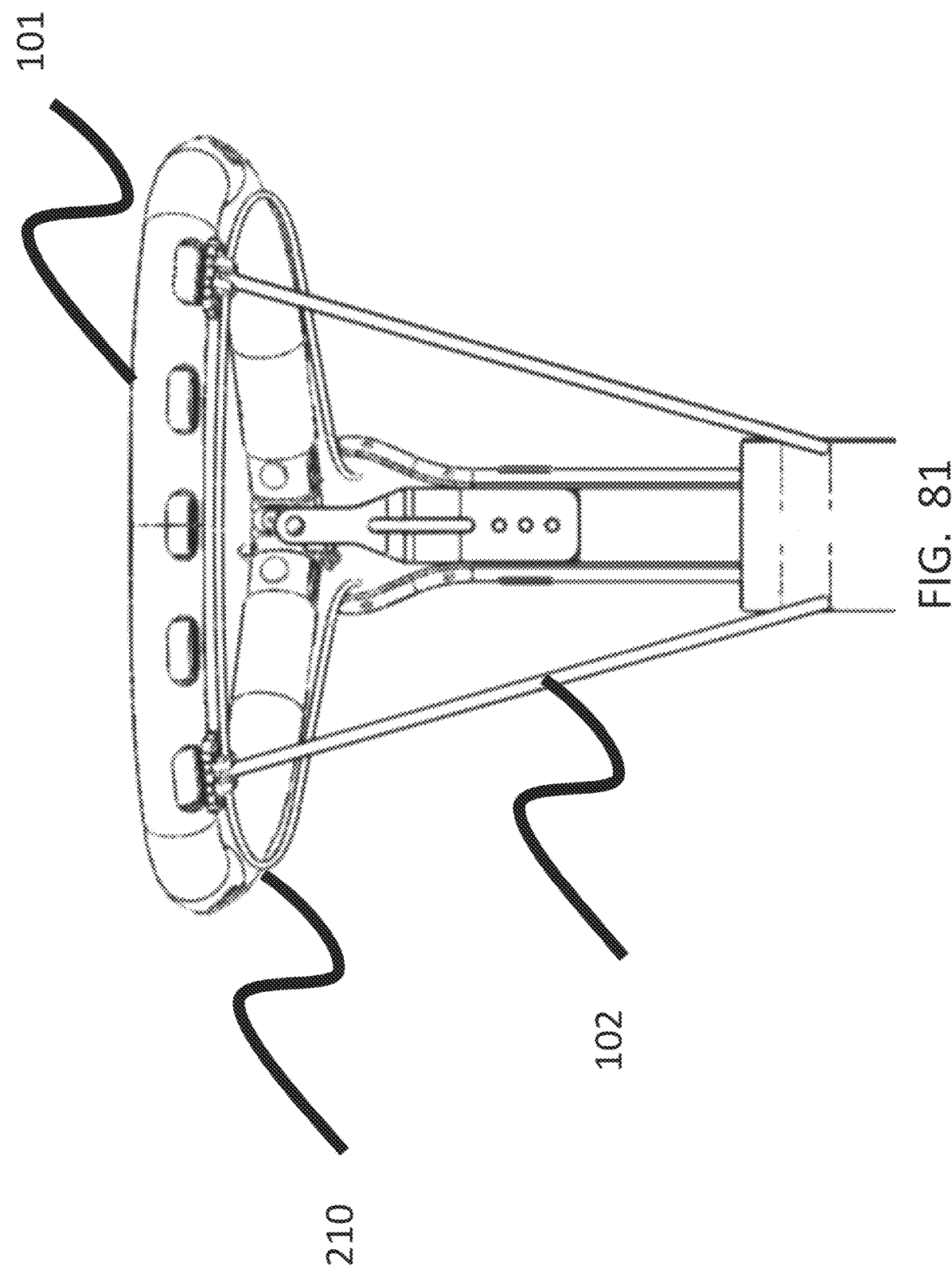

Referring now to FIGS. 79-81, embodiments are shown comprising an annuloplasty ring 101, a stabilizing mechanism 102, a docking post 201, and a deactivation wire 210. As shown, the stabilizing mechanism 102 may include a plurality of wires and may be attached to the annuloplasty ring 101 via a docking post 201 using a deactivation wire 210. In some embodiments, the deactivation wire 210 may follow approximately the same pathway as the stabilizing mechanism 102. Alternatively, the deactivation wire 210 may follow a different pathway than the stabilizing mechanism 102 based on situational requirement (e.g., an amount of force to be transferred to the annuloplasty ring 101).

If a significant amount of force must be transferred or applied to the annuloplasty ring 101, it may be beneficial for the deactivation wire 210 to follow the path of the stabilization mechanism 102. In an embodiment where forces need to be cancelled out (i.e., not applied to the annuloplasty ring 101), the stabilizing mechanism 102 may be passed through the attachment mechanism of the annuloplasty ring to the delivery system (FIG. 63 at 103) to prevent force transmission from use of the stabilizing mechanism 102 and tongue in the delivery system.

Figure 82:
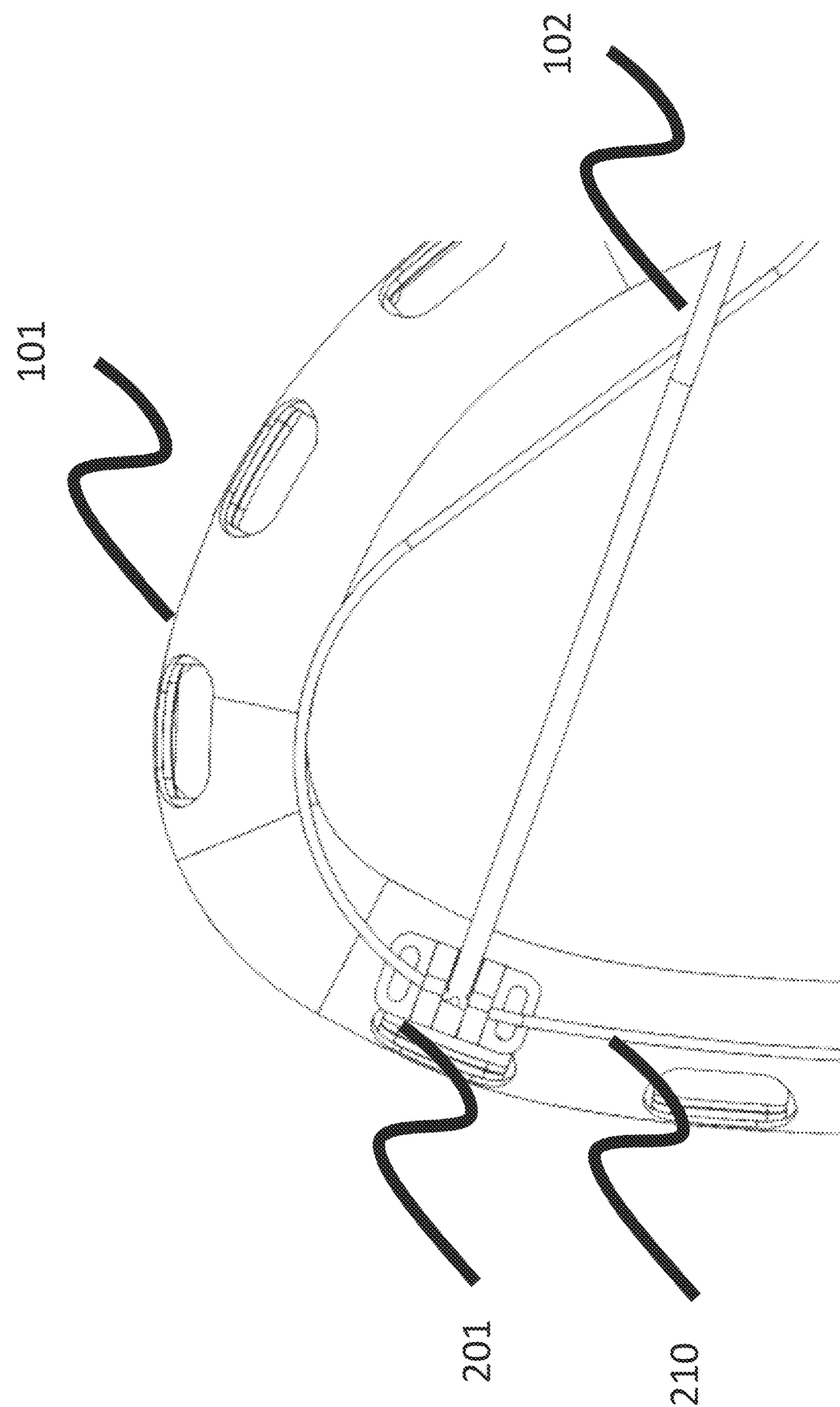
Figure 83:
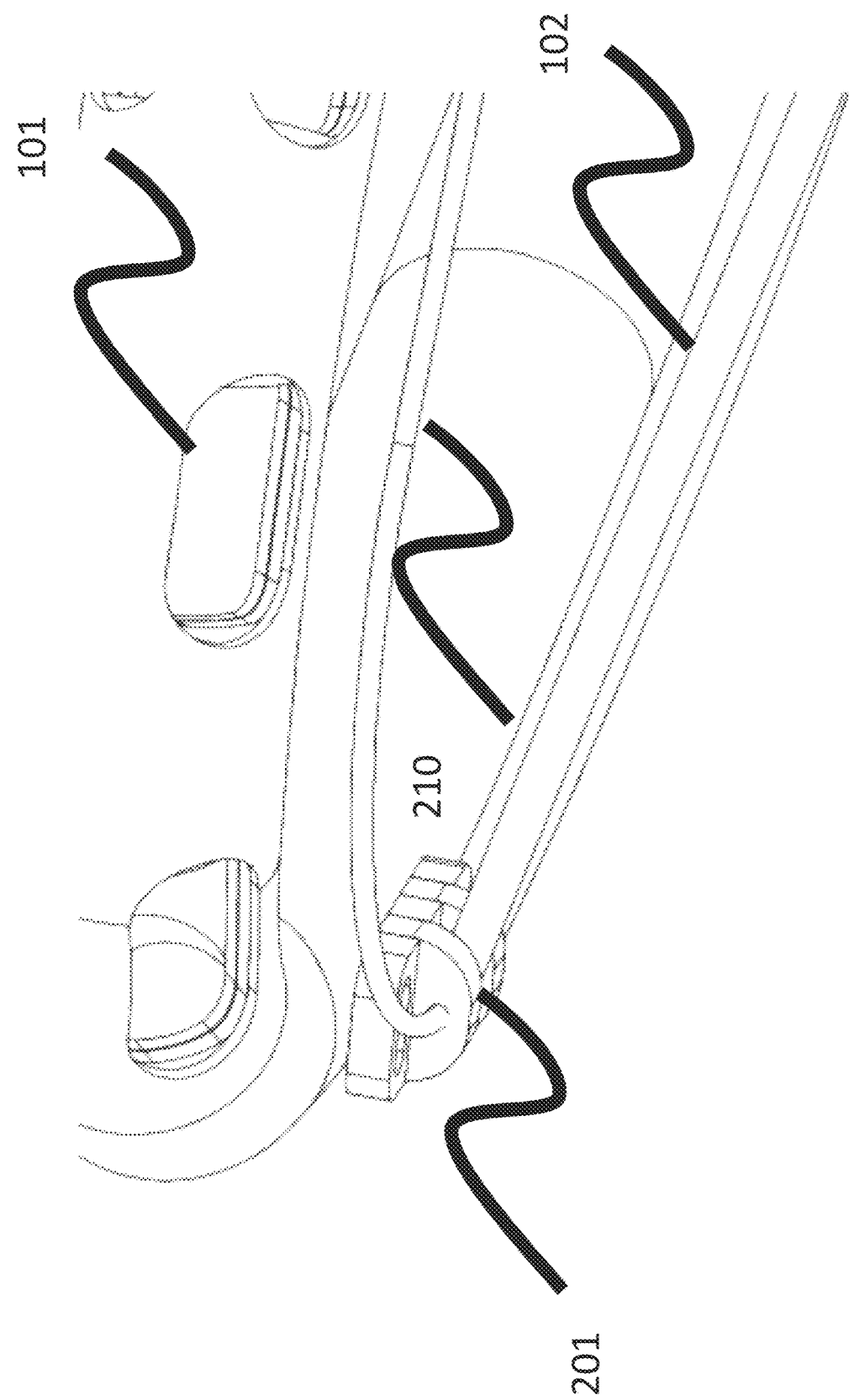
Figure 84:
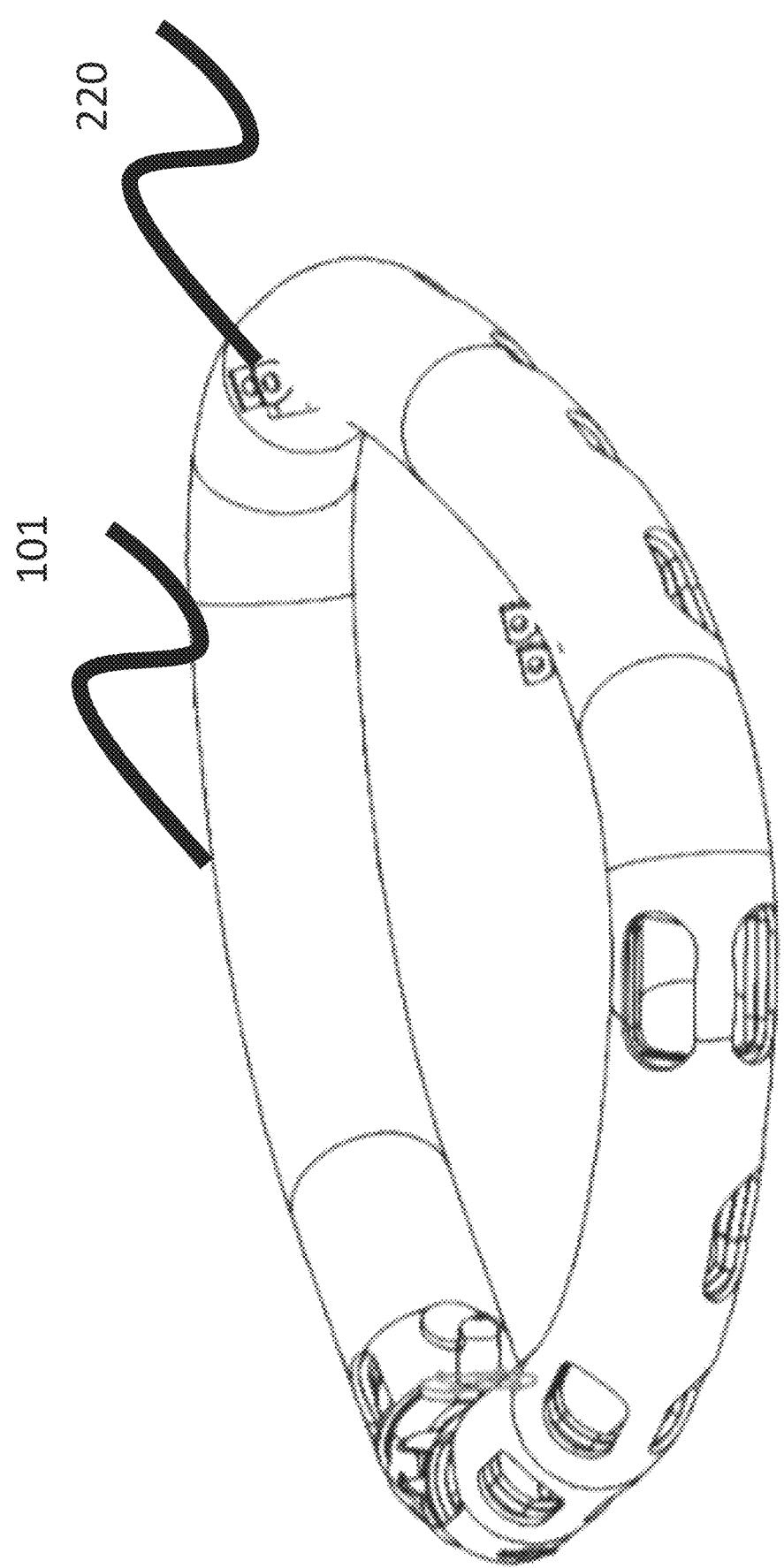
Figure 85:
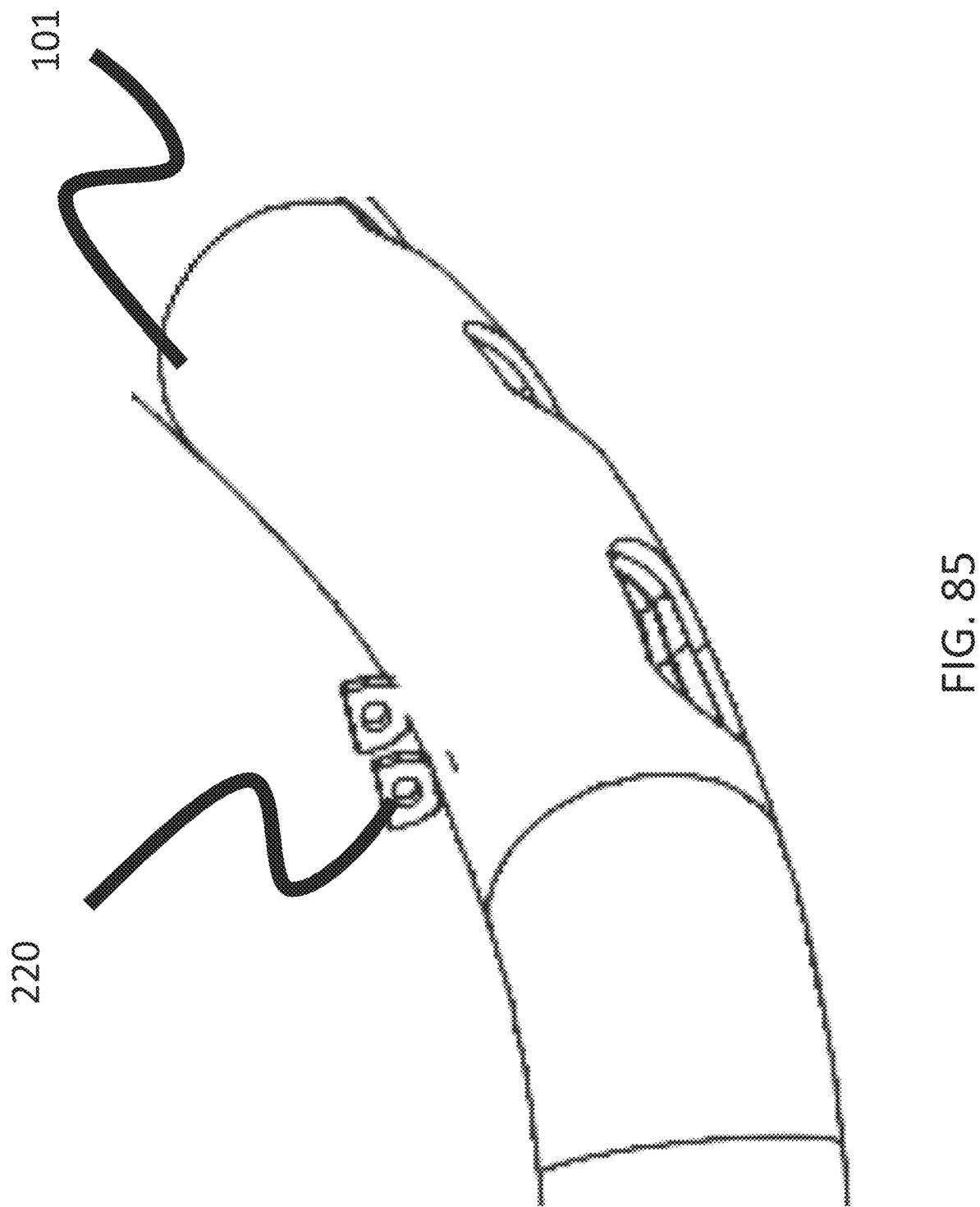
Figure 86:
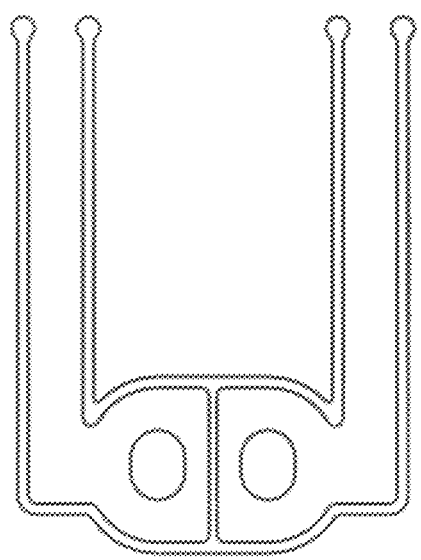
Figure 87:
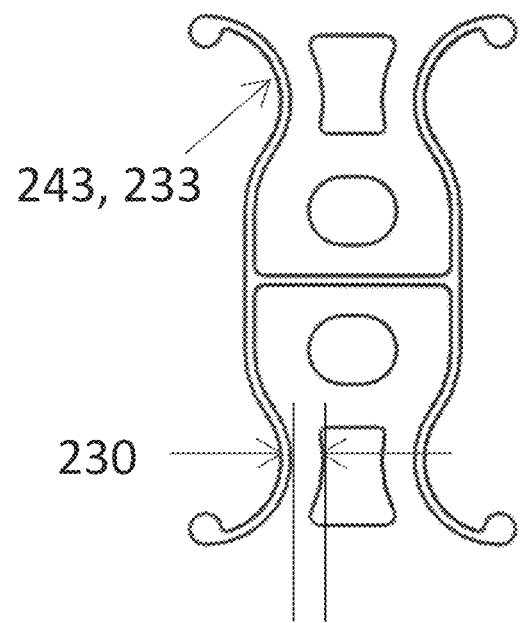
Figure 88:
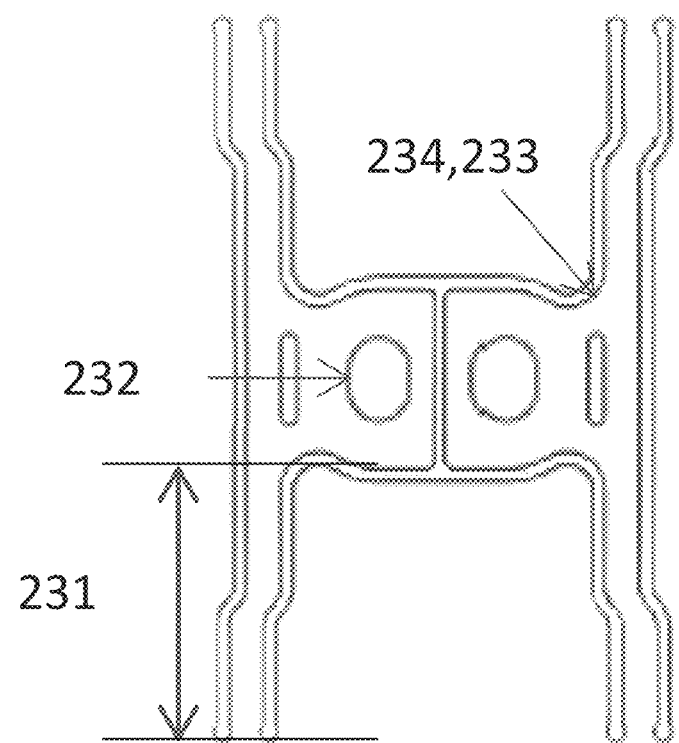
Figure 89:
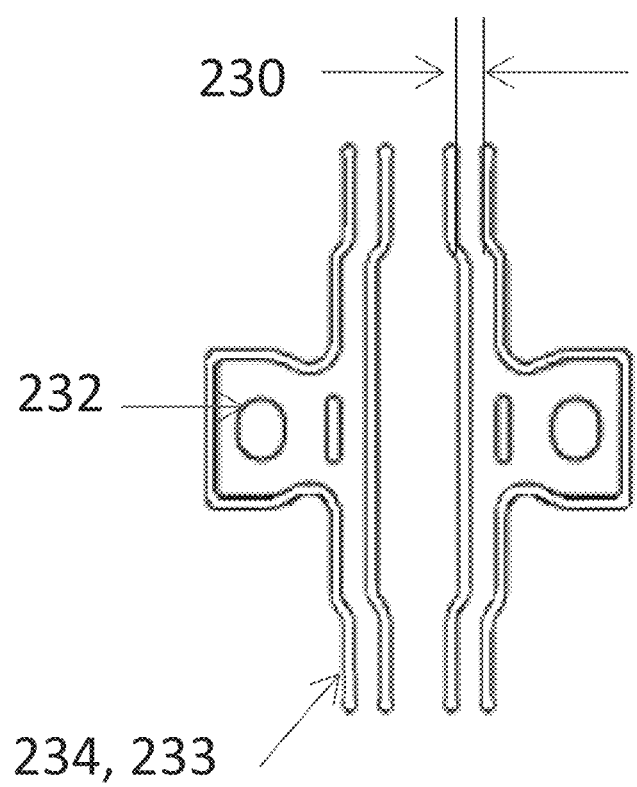
Figure 90:
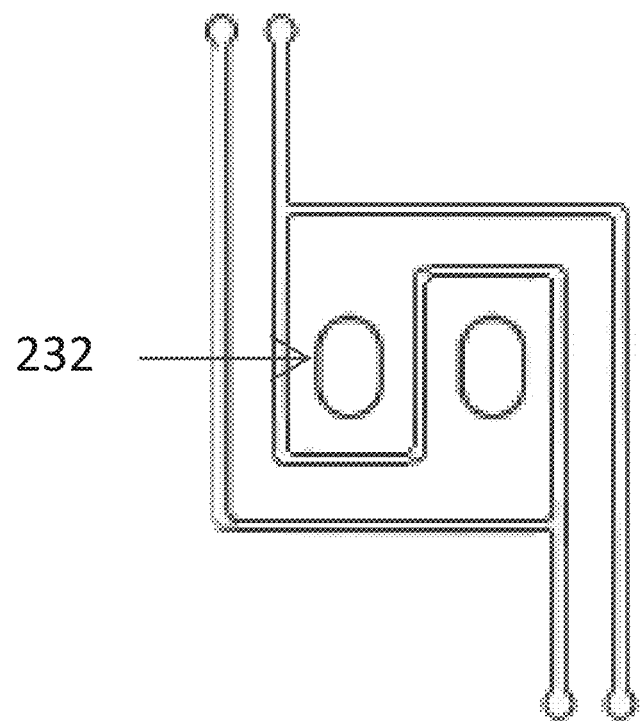
Figure 91:
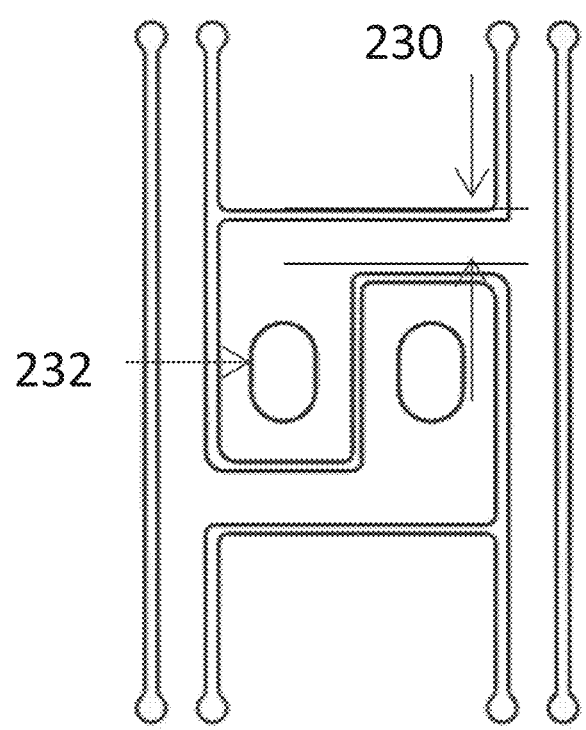
Figure 92:
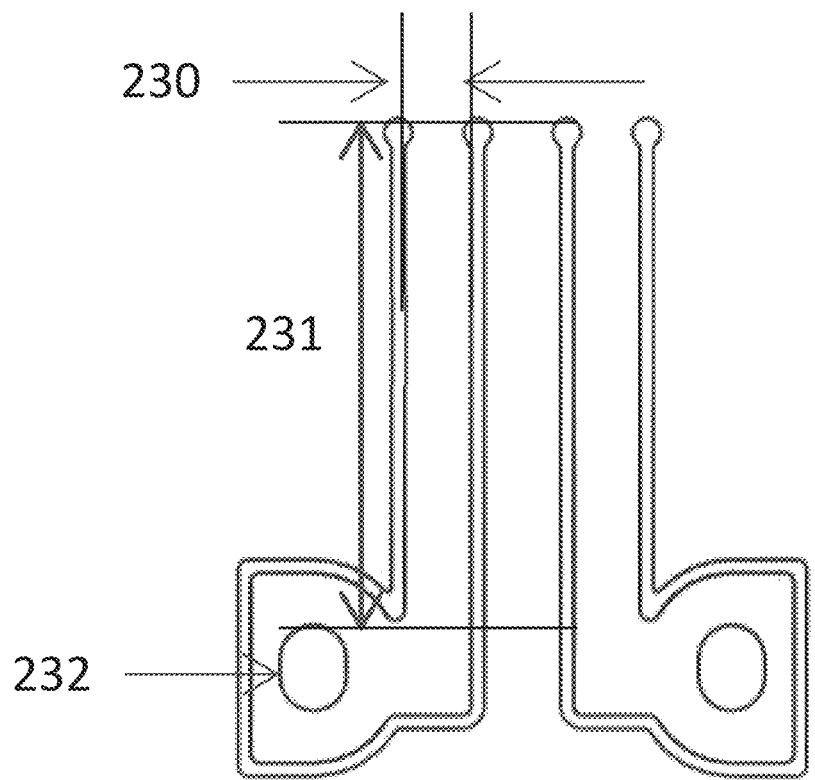
Figure 93:
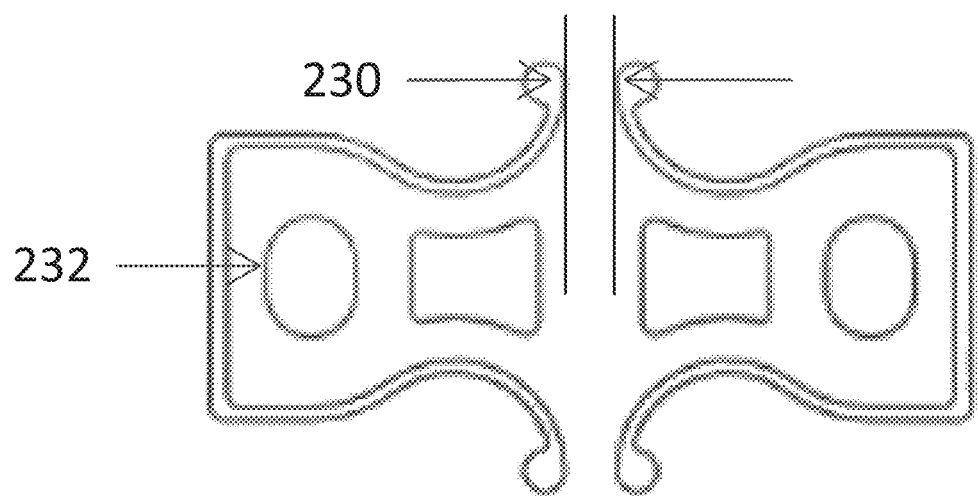

Turning now to FIGS. 82 and 83, an illustrative embodiment is shown regarding the detail of the docking post 201 sub-assembly. As shown, the docking post 201 is attached to the annuloplasty ring 101, and the stabilizing mechanism 102 is attached via the docking post which includes a deactivation wire 210. FIGS. 84 and 85 illustrate an alternative embodiment in which one or more docking posts 220 are integrated into the annuloplasty ring 101. In some embodiments, the docking posts 220 may be laser cut from the wall of the annuloplasty ring 101 and bent outward. In some further embodiments, the docking posts 220 may be permanently bent outward or have the ability to flex back into the wall of the annuloplasty ring 101 depending on the elasticity of the material.

The embodiments shown in FIGS. 84 and 85 may not require additional components, but rather can be cut directly from the wall of the annuloplasty ring 101. In addition, in some embodiments, after releasing the deactivation wire 210, the docking posts 220 may return to their original location within the wall of the annuloplasty ring 101 (i.e., leave no residual footprint that extends from the surface of the annuloplasty ring 101.

Referring now to FIGS. 86-93, illustrative example embodiments are shown of various potential laser cut patters for the docking posts 220. As shown, the start widths 230, start length 231, hole dimensions 232, bending/torqueing areas 234, and radii 233 may vary based on design and need. It should be understood that various other design patterns may be used. The potential patterns may be excessive and thus the embodiments shown are for exemplary purposes only. In some embodiments, the geometry may be varied based on the forces required to hold the stabilization mechanism 102, to hold and release the deactivation wire 210, and/or to bend or to resist bending the docking post as it relates to the annuloplasty ring 101.

Figure 94:
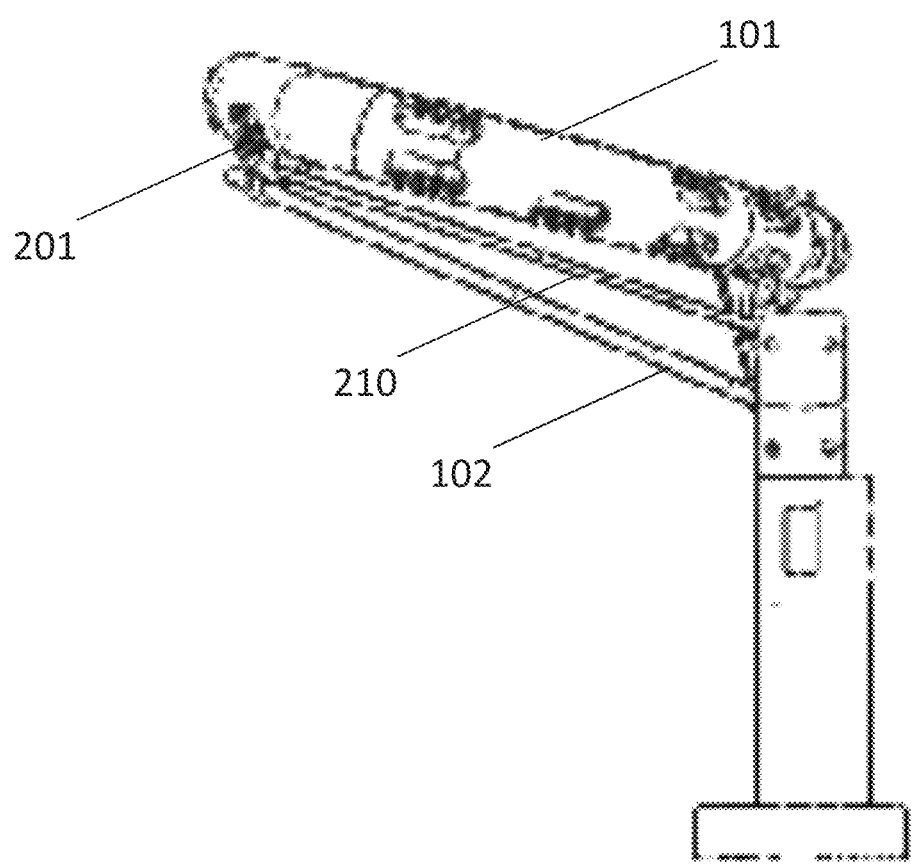
Figure 95:
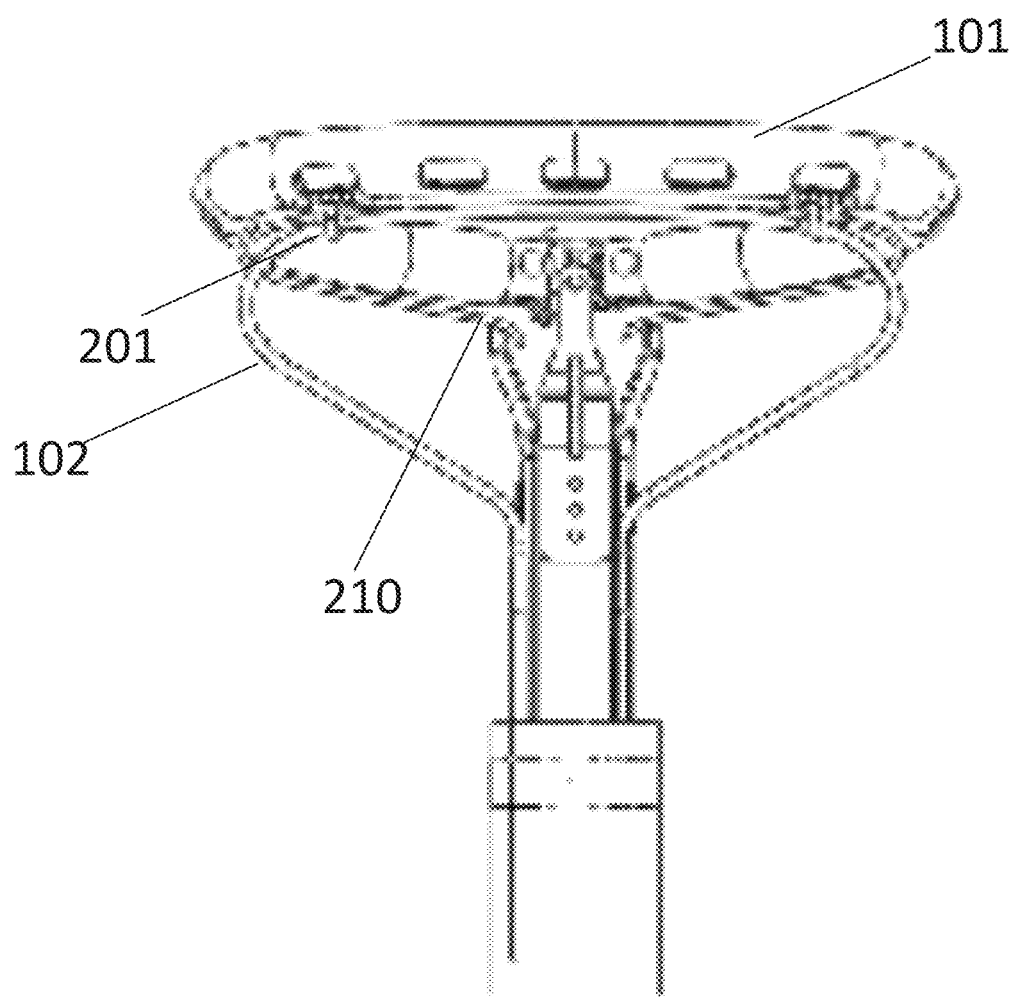
Figure 96:
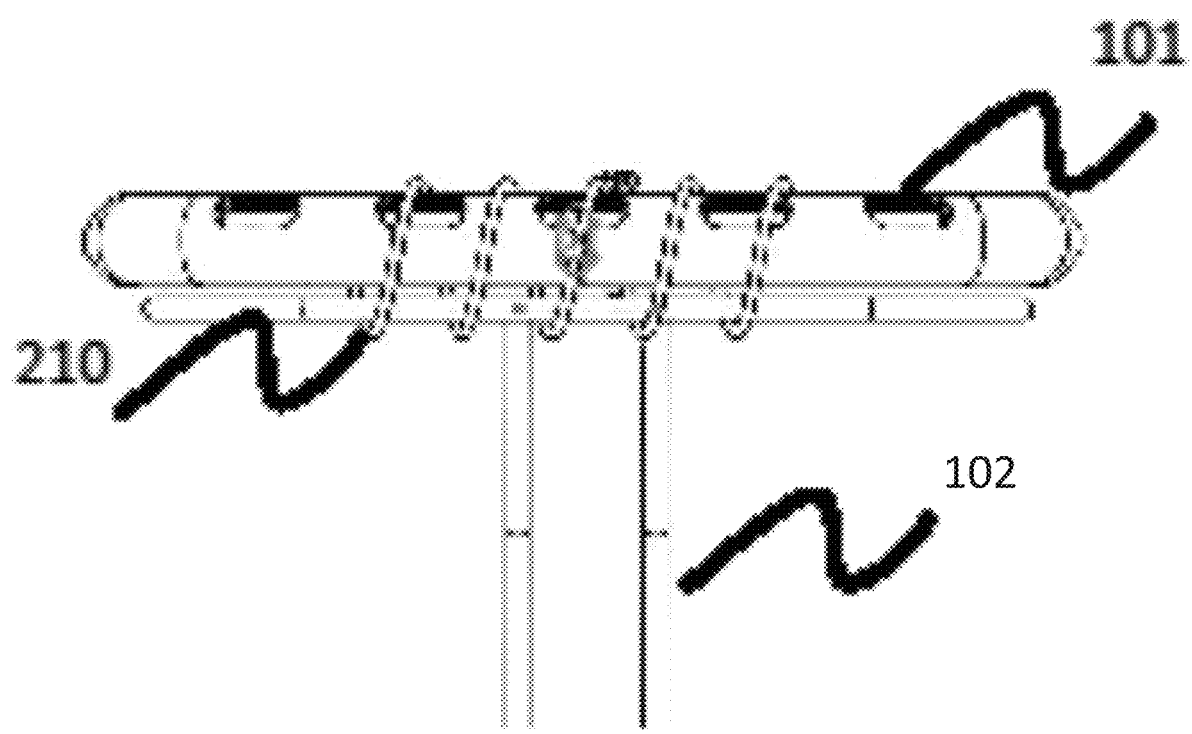
Figure 97:
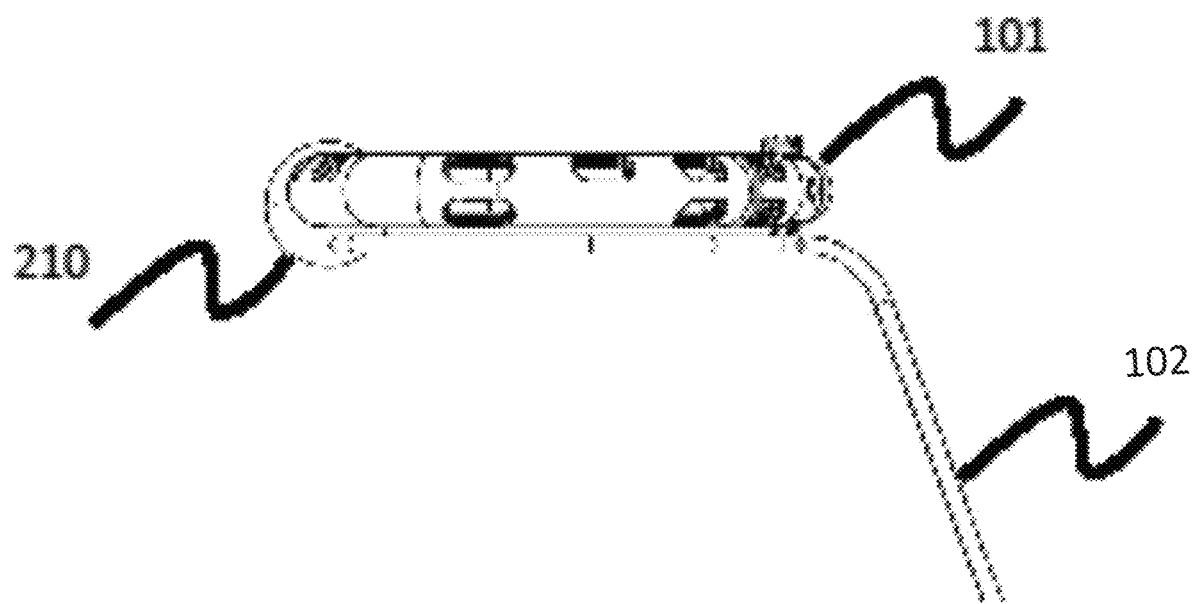
Figure 98:
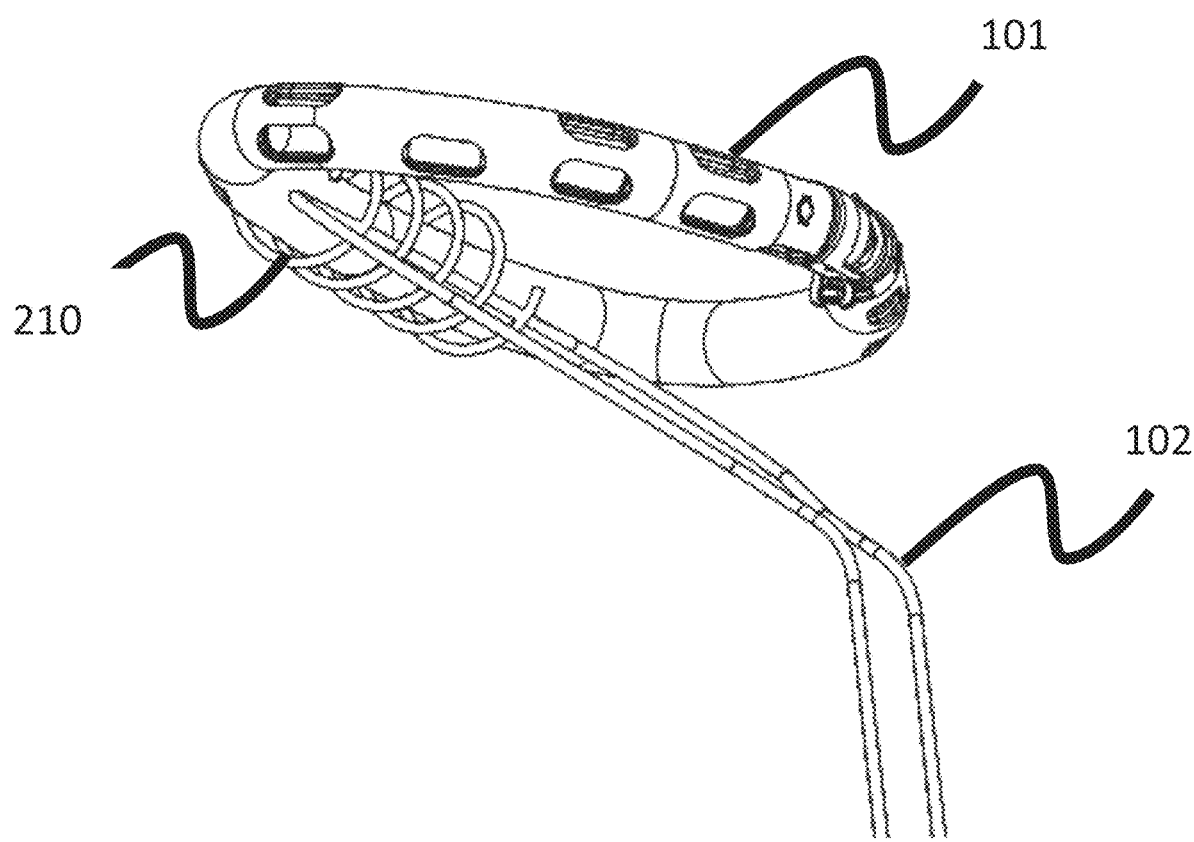
Figure 99:
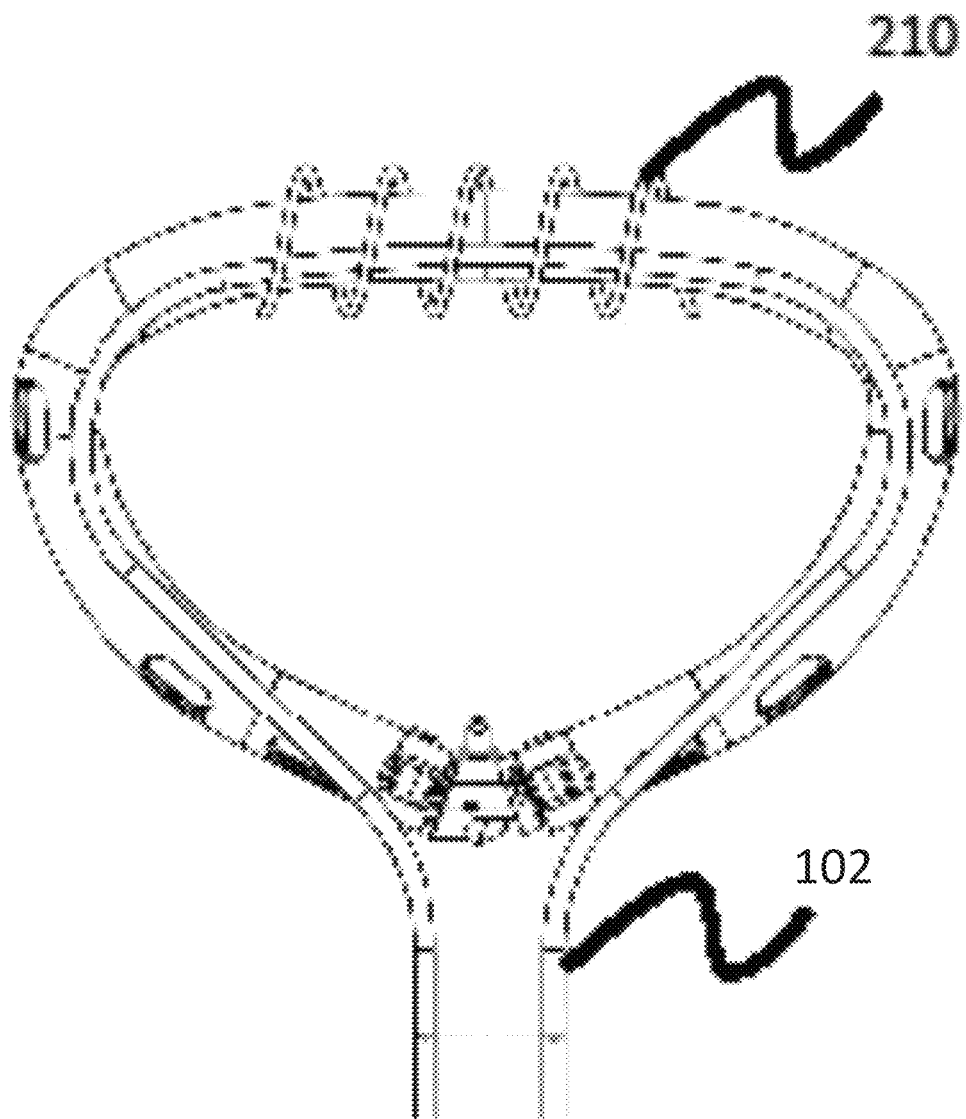

FIGS. 94 and 95 show an annuloplasty ring 101 with the stabilizing mechanism 102 attached through one or more docking posts 201, as well as the deactivation wire 210. As shown in FIG. 94, the stabilization mechanism 102 is a single unit.

In an alternative embodiment, such as that shown in FIGS. 96-99, the system may not require a docking post 201. FIGS. 96-99 depict illustrative embodiments in which the stabilization mechanism 102 is attached to the annuloplasty ring 101 via one or more sutures. In some embodiments, the sutures may wrap around the stabilization mechanism 102. The suture-based attachment may be wrapped around the annuloplasty ring 101 and the stabilizing mechanism 102. In an embodiment, the total number of wraps may vary from 1 wrap to about 20 wraps based on a required force. Alternatively, the suture-based attachment may pass through dedicated holes in the annuloplasty ring 101 or through fabric surrounding the annuloplasty ring.

In a further embodiment, an end of the sutures may be threaded along the annuloplasty ring 101. For example, the end of the sutures may be threaded inside the ring tube, between the ring tube and the outer fabric layer, or outside the fabric (e.g., through the delivery system interface 103 and through the delivery system lumens to the proximal end). One end of the sutures may be pulled to release the annuloplasty ring 101. The stabilization mechanism 102 may then be disconnected from the annuloplasty ring 101. The stabilization mechanism (e.g., wire) may further be retrieved completely or partially via the delivery system and, if required, removed fully from the delivery system.

Figure 100:
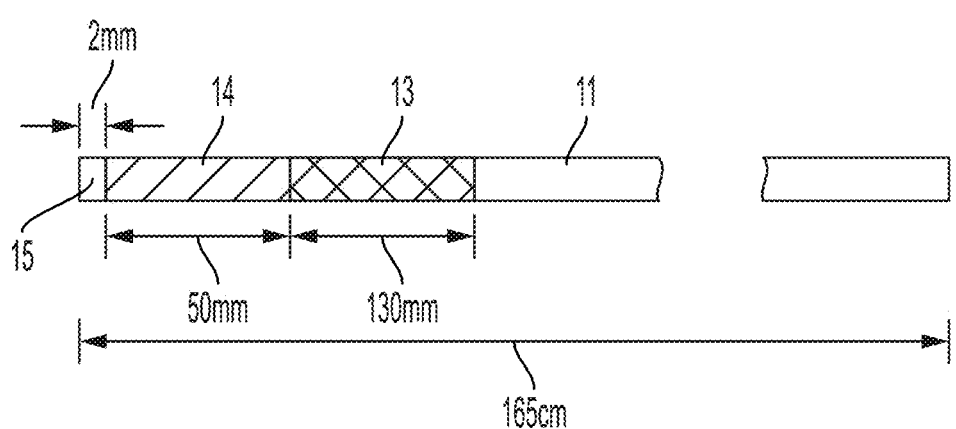

Referring now to FIG. 100, an illustrative schematic of at least one of the hypotubes 11 is shown. As illustrated in FIG. 100, the hypotube 11 may comprise various sections having varied characteristics. For example, a portion of the hypotube (e.g., 11) may be a solid and thus more structurally rigid and resilient. In another embodiment, a portion of the tube (e.g., 13) may be a flexible section. In a further embodiment, the flexible section 13 may reside within both the inner catheter 2 and one or more portions of the hypotube 11. For example the flexible section 13 may be inserted into the one or more solid portions of the hypotube (e.g., 11 and/or 14).

FIG. 100 further shows section 14 which may represent a solid portion of the hypotube 11. In some embodiments, section 14 may provide increased strength to allow for optimal push-ability without flexing or altering position. In one embodiment, the hypotube 11 may have a distal segment 15 that may be solid. It should be understood, that the embodiment shown in FIG. 100 is for illustrative purposes only, and that various additional embodiments may exist or be used. For example, there could be additional sections (e.g., 5, 6, 7 . . . 20, etc.) combined to form the full hypotube 11. Moreover, each section may be constructed independently (e.g., the sections could be of a different material, as disclosed herein), and could comprise different properties (e.g., more or less flexible).

Figure 101:
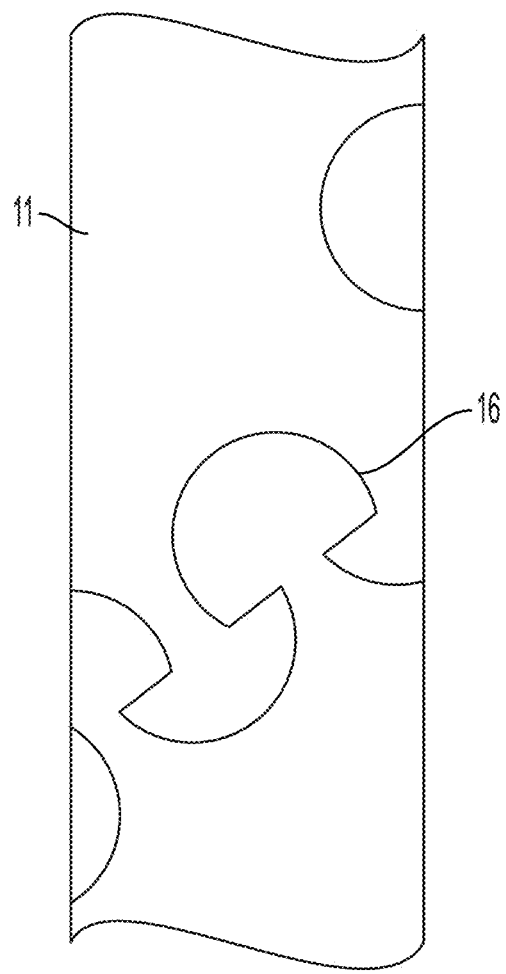

In a further embodiment, and as shown in FIG. 101, the distal end 13 of the hypotube 11 may have a pattern 16 cut into the construction material (e.g., a laser cut pattern). In an embodiment, the pattern 16 may be a spiral mushroom head pattern or any other pattern disclosed herein (e.g., FIGS. 2, 3, 4, 6, 7, 10, 11, 12, etc.) or capable of providing sufficient flexibility and rigidity to deliver the stabilizing mechanism 4 (i.e., allowing varying flexibility that may be required to negotiate sharp bends as the inner catheter 2 is navigated in a trans-septal manner).

Figure 102:
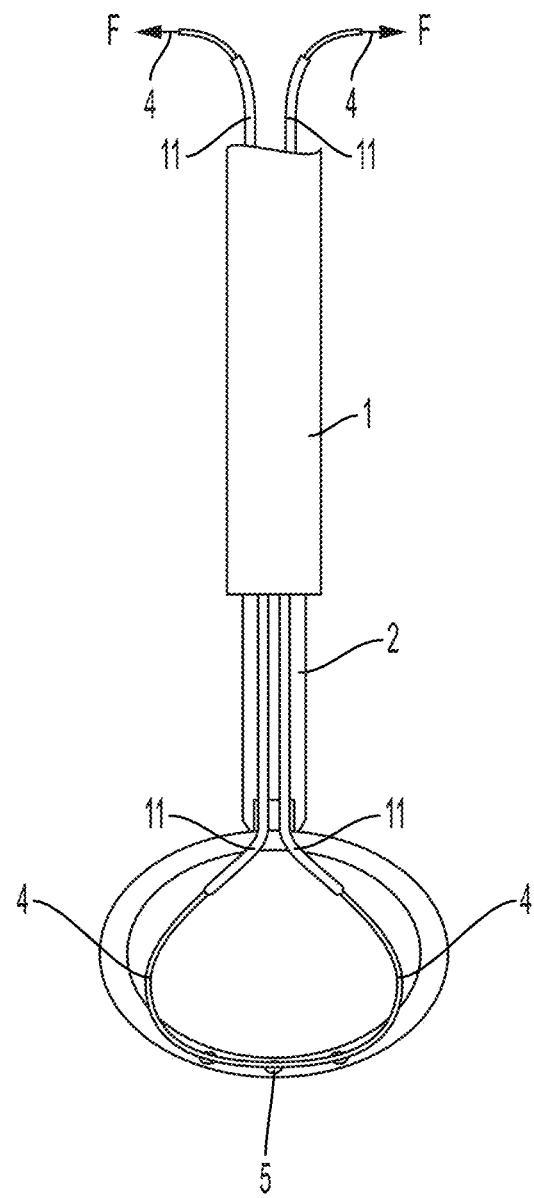

In some embodiments, the annuloplasty ring 3 may be controlled by applying tension and/or biasing force on proximal end of the stabilizing mechanism 4, which is attached to the annuloplasty ring and threaded through the one or more hypotubes 11. The applied tension may, in some embodiments, push the hypotubes 11 distally to engage the annuloplasty ring 3. Accordingly, as shown in FIG. 102, according to some embodiments, the stabilizing mechanism 4 attaches at the distal end to the annuloplasty ring 3 and exits at the proximal end into a handle or manipulation device. The stabilizing mechanism 4 may then be removed by pulling on one end of the stabilizing mechanism at one of the proximal ends whereby the opposite proximal end (e.g., the trailing end) is pulled away from annuloplasty ring 3 (e.g., through the connection points 5) and through the one or more hypotubes 11.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of delivering a tricuspid ring comprising:
delivering an annuloplasty ring in a linear shape using a delivery system;
positioning of the annuloplasty ring from a linear shape to an annular operable shaped geometry using a flexible stabilizing mechanism,
wherein the annuloplasty ring comprises one or more docking posts, wherein each docking post engages with a distal end of the flexible stabilizing mechanism, and wherein the distal end of the flexible stabilizing mechanism is secured to each docking post by a deactivation wire that slides through two apertures that are disposed on opposing sides of each docking post and the distal end of the flexible stabilizing mechanism to secure the distal end of the flexible stabilizing mechanism to the docking post; and
activating one or more anchors to extend outward from the annuloplasty ring.

2. The method of claim 1, wherein the one or more docking posts comprise one or more laser cut portions of the annuloplasty ring.

3. The method of claim 1, wherein the flexible stabilizing mechanism is a unitary body having the distal end, a first proximal end, and a second proximal end.

4. The method of claim 3, wherein the distal end is removably attached to the annuloplasty ring.

5. The method of claim 3, wherein positioning of the annuloplasty ring comprises applying a biasing force to at least one of the first proximal end and the second proximal end.

6. The method of claim 1, further comprising shaping the annuloplasty ring using the flexible stabilizing mechanism prior to delivery.

7. The method of claim 1, wherein a height is reduced by 15% to 20%.

8. The method of claim 1, wherein the activating the one or more anchors to extend outward is based on one or more predefined zones on the annuloplasty ring.

9. The method of claim 1, retracting the one or more docking posts into the annuloplasty ring.

10. The method of claim 1, wherein delivery of the annuloplasty ring utilizes a trans-septal approach.

11. The method of claim 1, wherein delivery of the annuloplasty ring utilizes a trans-femoral approach.

12. The method of claim 1, wherein delivery of the annuloplasty ring utilizes a trans-apical approach.

13. The method of claim 1, wherein delivery of the annuloplasty ring utilizes a trans-jugular approach.

* * * * *